United States Patent
Kamm et al.

(10) Patent No.: US 10,767,149 B2
(45) Date of Patent: Sep. 8, 2020

(54) MICROFLUIDIC DEVICE FOR THREE DIMENSIONAL AND COMPARTMENTALIZED COCULTURE OF NEURONAL AND MUSCLE CELLS, WITH FUNCTIONAL FORCE READOUT

(71) Applicant: Massachusetts Institute of Technology, Cambridge, MA (US)

(72) Inventors: Roger Dale Kamm, Cambridge, MA (US); Sebastien G M Uzel, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 279 days.

(21) Appl. No.: 15/621,893

(22) Filed: Jun. 13, 2017

(65) Prior Publication Data
US 2017/0355945 A1    Dec. 14, 2017

Related U.S. Application Data

(60) Provisional application No. 62/349,270, filed on Jun. 13, 2016.

(51) Int. Cl.
*C12M 1/32* (2006.01)
*C12M 3/06* (2006.01)
(Continued)

(52) U.S. Cl.
CPC .......... *C12M 23/16* (2013.01); *C12M 21/08* (2013.01); *C12M 23/34* (2013.01); *C12M 25/00* (2013.01); *C12M 33/06* (2013.01); *C12N 5/0697* (2013.01); *G01N 33/4833* (2013.01); *G01N 33/5058* (2013.01); *G01N 33/5061* (2013.01); *C12M 23/12* (2013.01); *C12N 2502/081* (2013.01);
(Continued)

(58) Field of Classification Search
CPC .. C12M 23/12; C12M 23/16; C12N 2502/081
See application file for complete search history.

(56) References Cited

U.S. PATENT DOCUMENTS

| 8,985,547 B2 | 3/2015 | Weibel et al. |
| 9,121,847 B2 | 9/2015 | Kamm et al. |

(Continued)

FOREIGN PATENT DOCUMENTS

| WO | 2013/056019 A1 | 4/2013 |
| WO | 2014/028940 A1 | 2/2014 |

(Continued)

OTHER PUBLICATIONS

Andrasfalvy et al. (Jun. 29, 2010) "Two-Photon Single-Cell Optogenetic Control of Neuronal Activity by Sculpted Light", Proceedings of the National Academy of Sciences, 107(26):11981-11986.

(Continued)

*Primary Examiner* — Jonathan M Hurst
(74) *Attorney, Agent, or Firm* — Mintz, Levin, Cohn, Ferris, Glovsky and Popeo, P.C.

(57) ABSTRACT

The present subject matter provides a microfluidic device that enables the precise and repeatable three dimensional and compartmentalized coculture of muscle cells and neuronal cells. Related apparatus, systems, techniques, and articles are also described.

20 Claims, 30 Drawing Sheets

Specification includes a Sequence Listing.

(51) Int. Cl.
    C12M 1/12      (2006.01)
    C12M 3/00      (2006.01)
    C12M 1/00      (2006.01)
    C12N 5/071     (2010.01)
    G01N 33/483    (2006.01)
    G01N 33/50     (2006.01)
(52) U.S. Cl.
    CPC .. *C12N 2502/1335* (2013.01); *C12N 2513/00* (2013.01); *C12N 2531/00* (2013.01)

(56) References Cited

U.S. PATENT DOCUMENTS

| | | | |
|---|---|---|---|
| 9,523,672 B2* | 12/2016 | Chung | C12M 23/16 |
| 10,233,415 B1* | 3/2019 | Mathur | C12M 23/16 |
| 2005/0003544 A1 | 1/2005 | Goldman et al. | |
| 2008/0257735 A1* | 10/2008 | Jeon | B01L 3/502707 204/453 |
| 2011/0159522 A1 | 6/2011 | Kamm et al. | |
| 2011/0306041 A1* | 12/2011 | Viovy | C12M 23/16 435/6.1 |
| 2014/0057311 A1 | 2/2014 | Kamm et al. | |
| 2014/0141514 A1* | 5/2014 | Yoon | C12M 23/16 435/383 |
| 2014/0220555 A1* | 8/2014 | Chen | C12N 5/0062 435/5 |
| 2014/0274796 A1 | 9/2014 | Hickman | |
| 2015/0030595 A1 | 1/2015 | Lee et al. | |
| 2015/0087006 A1* | 3/2015 | Pak | C12M 23/16 435/29 |
| 2016/0097027 A1* | 4/2016 | Nikkhah | C12M 23/16 435/32 |
| 2018/0267014 A1* | 9/2018 | Perlson | G01N 33/48728 |
| 2018/0298317 A1* | 10/2018 | Ingber | C12M 23/16 |
| 2019/0316068 A1* | 10/2019 | Chen | C12N 5/0606 |

FOREIGN PATENT DOCUMENTS

| | | |
|---|---|---|
| WO | 2015/013210 A1 | 1/2015 |
| WO | 2017/218581 A1 | 12/2017 |

OTHER PUBLICATIONS

Arnold et al. (Apr. 1, 2014) "Morphological and Functional Remodeling of the Neuromuscular Junction by Skeletal Muscle PGC-1α", Nature Communications, 5:26 pages.
Asano et al. (Jan. 2012) "Optically Controlled Contraction of Photosensitive Skeletal Muscle Cells", Biotechnology and Bioengineering, 109(1)199-204.
Bach et al. (Nov. 2003) "Expression of Trisk 51, Agrin and Nicotinic-Acetylcholine Receptor Epsilon-Subunit During Muscle Development in a Novel Three-Dimensional Muscle-Neuronal Co-Culture System", Cell and Tissue Research, 314(2):263-274.
Bonanomi et al. (Mar. 2010) "Motor Axon Pathfinding", Cold Spring Harbor Perspectives in Biology, 2(3):19 pages.
Boudou et al. (May 2012) "A Microfabricated Platform to Measure and Manipulate the Mechanics of Engineered Cardiac Microtissues", Tissue Engineering Part A, 18(9-10):910-919.
Boyden et al. (Sep. 2005) "Millisecond-Timescale, Genetically Targeted Optical Control of Neural Activity", Nature Neuroscience, 8(9):1263-1268.
Bryson et al. (Apr. 4, 2014) "Optical Control of Muscle Function by Transplantation of Stem Cell-Derived Motor Neurons in Mice", Science, 344(6179):10 pages.
Caggiano et al. (Jun. 25, 2014) "Rostro-Caudal Inhibition of Hindlimb Movements in the Spinal Cord of Mice", PLOS One, 9(6):11 pages.
Campenot et al. (2009) "Production of Compartmented Cultures of Rat Sympathetic Neurons", Nature Protocols, 4 (12):1869-1887.
Cao et al. (Jun. 20, 2007) "Schwann Cell-Derived Factors Modulate Synaptic Activities at Developing Neuromuscular Synapses", The Journal of Neuroscience, 27(25):6712-6722.

Chan et al. (Nov. 15, 2012) "Development of Miniaturized Walking Biological Machines", Scientific Reports, 2 (857):8 pages.
Chan et al. (May 21, 2015) "Fabrication and Characterization of Optogenetic, Multi-Strip Cardiac Muscles", Lab on a Chip, 15(10):2258-2268.
Chipman et al. (Mar. 2014) "A Stem-Cell Based Bioassay to Critically Assess the Pathology of Dysfunctional Neuromuscular Junctions", PLOS One, 9(3):13 pages.
Cohen et al. (Jan. 1978) "Motor Control of Buccal Muscles in Aplysia", Journal of Neurophysiology, 41 (1):157-180.
Cvetkovic et al. (Jul. 15, 2014) "Three-Dimensionally Printed Biological Machines Powered by Skeletal Muscle", Proceedings of the National Academy of Sciences, 111(28):10125-10130.
Dale et al. (May 4, 1936) "Release of Acetylcholine at Voluntary Motor Nerve Endings", The Journal of Physiology, 86(4):353-380.
Das et al. (May 11, 2007) "Embryonic Motoneuron-Skeletal Muscle Co-Culture in a Defined System", Neuroscience, 146(2):481-488.
Dimos et al. (Aug. 29, 2008) "Induced Pluripotent Stem Cells Generated from Patients with ALS Can Be Differentiated into Motor Neurons", Science, 321(5893):1218-1221.
Ebens et al. (Dec. 1996) "Hepatocyte Growth Factor/Scatter Factor is an Axonal Chemoattractant and a Neurotrophic Factor for Spinal Motor Neurons", Neuron, 17(6):1157-1172.
Ebert et al. (Jan. 15, 2009) "Induced Pluripotent Stem Cells From a Spinal Muscular Atrophy Patient", Nature, 457(7227):277-280.
Engler et al. (Sep. 13, 2004) "Myotubes Differentiate Optimally on Substrates with Tissue-Like Stiffness: Pathological Implications for Soft or Stiff Microenvironments", Journal of Cell Biology, 166(6):877-887.
Fatt et al. (May 1952) "Spontaneous Subthreshold Activity at Motor Nerve Endings", The Journal of Physiology, 117 (1):109-128.
Feinberg et al. (Sep. 7, 2007) "Muscular Thin Films for Building Actuators and Powering Devices", Science, 317(5843):1366-1370.
Fitzsimonds et al. (Jan. 1998) "Retrograde Signaling in the Development and Modification of Synapses", Physiological Reviews, 78(1):143-170.
Frank et al. (Oct. 1, 1979) "Early Events in Neuromuscular Junction Formation in Vitro: Induction of Acetylcholine Receptor Clusters in the Postsynaptic Membrane and Morphology of Newly Formed Synapses", Journal of Cell Biology, 83(1):143-158.
Gensler et al. (Apr. 2001) "Assembly and Clustering of Acetylcholine Receptors Containing GFP-Tagged Epsilon or Gamma Subunits: Selective Targeting to the Neuromuscular Junction in Vivo", European Journal of Biochemistry, 268 (8):2209-2217.
Gervasio et al. (Feb. 1, 2005) "Increased Ratio of Rapsyn to ACh Receptor Stabilizes Postsynaptic Receptors at the Mouse Neuromuscular Synapse", The Journal of Physiology, 562(Pt. 3):673-685.
Guo et al. (Dec. 2010) "Neuromuscular Junction Formation Between Human Stem-Cell-Derived Motoneurons and Rat Skeletal Muscle in a Defined System", Tissue Engineering Part C: Methods, 16(6):1347-1355.
Harper et al. (May 4, 2004) "Axonal Growth of Embryonic Stem Cell-Derived Motoneurons In Vitro and in Motoneuron-Injured Adult Rats", Proceedings of the National Academy of Sciences, 101(18):7123-7128.
Hester et al. (Oct. 2011) "Rapid and Efficient Generation of Functional Motor Neurons From Human Pluripotent Stem Cells Using Gene Delivered Transcription Factor Codes", Molecular Therapy, 19(10):1905-1912.
Hinds et al. (May 2011) "The Role of Extracellular Matrix Composition in Structure and Function of Bioengineered Skeletal Muscle", Biomaterials, 32(14):20 pages.
Hughes et al. (Nov. 5, 2005) "Guillain-Barré Syndrome", The Lancet, 366(9497):1653-1666.
Ilina et al. (2011) "Two-Photon Laser-Generated Microtracks in 3D Collagen Lattices: Principles of MMP-Dependent and -Independent Collective Cancer Cell Invasion", Physical Biology, 8(1):8 pages.
Ionescu et al. (Feb. 2016) "Compartmental Microfluidic System for Studying Muscle-Neuron Communication and Neuromuscular Junction Maintenance", European Journal of Cell Biology, 95(2): 69-88.
Jorgensen et al. (Jun. 1995) "Neuromuscular Junctions in the Nematode C. Elegans", Seminars in Developmental Biology, 6(3):207-220.

(56) References Cited

OTHER PUBLICATIONS

Juhas et al. (Apr. 15, 2014) "Biomimetic Engineered Muscle with Capacity for Vascular Integration and Functional Maturation In Vivio", Proceedings of the National Academy of Sciences, 111(15)5508-5513.
Keshishian et al. (Mar. 1996) "The Drosophila Neuromuscular Junction: A Model System for Studying Synaptic Development and Function", Annual Review of Neuroscience, 19:545-575.
Legant et al. (Jun. 23, 2009) "Microfabricated Tissue Gauges to Measure and Manipulate Forces from 3D Microtissures", Proceedings of the National Academy of Sciences, 106(25):10097-10102.
Li. et al. (Feb. 2005) "Specification of Motoneurons from Human Embryonic Stem Cells", Nature Biotechnology, 23(2):215-221.
Llewellyn et al. (Oct. 2010) "Orderly Recruitment of Motor Units Under Optical Control in Vivo", Nature Medicine, 16(10):1161-1165.
Luni et al. (Feb. 2014) "Human-On-Chip for Therapy Development and Fundamental Science", Current Opinion in Biotechnology, 25:45-50.
Mazzoni et al. (Sep. 2013) "Synergistic Binding of Transcription Factors to Cell-Specific Enhancers Programs Motor Neuron Identity", Nature Neuroscience, 16(9):1219-1227.
Miles et al. (Sep. 8, 2004) "Functional Properties of Motoneurons Derived from Mouse Embryonic Stem Cells", The Journal of Neuroscience, 24(36):7848-7858.
Morimoto et al. (Dec. 2013) "Three-Dimensional Neuron-Muscle Constructs with Neuromuscular Junctions", Biomaterials, 34(37)9413-9419.
Mosadegh et al. (Oct. 23, 2007) "Generation of Stable Complex Gradients Across Two-Dimensional Surfaces and Three-Dimensional Gels", Langmuir, 23(22):10910-10912.
Nagel et al. (Nov. 25, 2003) "Channelrhodopsin-2, a Directly Light-Gated Cation-Selective Membrane Channel", Proceedings of the National Academy of Sciences, 100(24):13940-13945.
Nawroth et al. (Aug. 2012) "A Tissue-Engineered Jellyfish with Biomimetic Propulsion", Nature Biotechnology, 30(8):792-797.
Neal et al. (Jun. 7, 2014) "Formation of Elongated Fascicle-Inspired 3D Tissues Consisting of High-Density, Aligned Cells Using Sacrificial Outer Molding", Lab on a Chip, 14(11):1907-1916.
Nédelec et al. (Jan. 25, 2012) "Concentration Dependent Requirement for Local Protein Synthesis in Motor Neuron Subtype Specific Response to Axon Guidance Cues", Journal of Neuroscience, 32(4):1496-1506.
Nelson et al. (Nov. 1993) "Synapse Elimination from the Mouse Neuromuscular Junction In Vitro: A Non-Hebbian Activity-Dependent Process", Developmental Neurobiology, 24(11):1517-1530.
Oheim et al. (Oct. 31, 2006) "Principles of Two-Photon Excitation Fluorescence Microscopy and Other Nonlinear Imaging Approaches", Advanced Drug Delivery Reviews, 58(7):788-808.
Olesen et al. (Jan. 2012) "The Economic Cost of Brain Disorders in Europe", European Journal of Neurology, 19(1):155-162.
Oron (2012) "Two-Photon Optogenetics", Progress in Brain Research, 196:119-143.
Park et al. (Sep. 20, 2010) "Increased Poly(Dimethylsiloxane) Stiffness Improves Viability and Morphology of Mouse Fibroblast Cells", Bio Chip Journal, 4(3):230-236.
Park et al. (2013) "Neuromuscular Junction in a Microfluidic Device", Conference Proceedings—IEEE Engineering in Medicine and Biology Society, 2013:2833-2835.
Pittier et al. (Apr. 2005) "Neurite Extension and In Vitro Myelination within Three-Dimensional Modified Fibrin Matrices", Journal of Neurobiology, 63(1):1-14.
Pulver et al. (Apr. 1, 2009) "Temporal Dynamics of Neuronal Activation by Channelrhodopsin-2 and TRPA1 Determine Behavioral Output in Drosophila Larvae", Journal of Neurophysiology, 101(6):3075-3088.
Rowlands et al. (Sep. 22, 2014) "3D-Resolved Targeting of Photodynamic Therapy Using Temporal Focusing", Laser Physics Letters, 11(11):7 pages.
Rubin et al. (Jan. 17, 1980) "Regulation of Acetylcholinesterase Appearance at Neuromuscular Junctions In Vitro", Nature, 283(5744)264-267.
Sakar et al. (2012) "Formation and Optogenetic Control of Engineered 3D Skeletal Muscle Bioactuatorst", Lab Chip, 12(23):4976-4985.
Sanes et al. (1999) "Development of the Vertebrate Neuromuscular Junction", Annual Review of Neuroscience, 22:389-442.
Sanes (1983) "Roles of Extracellular Matrix in Neural Development", Annual Review of Physiology, 45:581-600.
Saporta et al. (Jan. 2011) "Charcot Marie Tooth (CMT) Subtypes and Genetic Testing Strategies", Annals of Neurology, 69(1):22-33.
Schroll et al. (Sep. 5, 2006) "Light-Induced Activation of Distinct Modulatory Neurons Triggers Appetitive or Aversive Learning in Drosophila Larvae", Current Biology, 16:1741-1747.
Shin et al. (Jun. 2012) "Microfluidic Assay for Simultaneous Culture of Multiple Cell Types on Surfaces or within Hydrogels", Nature Protocols, 7(7):1247-1259.
Smith et al. (Sep. 2013) "A Functional System for High-Content Screening of Neuromuscular Junctions In Vitro", Technology, 1(1):37-48.
Son et al. (Jan. 1995) "Schwann Cell Processes Guide Regeneration of Peripheral Axons", Neuron, 14:125-132.
Southam et al. (Sep. 15, 2013) "Microfluidic Primary Culture Model of the Lower Motor Neuron—Neuromuscular Junction Circuit", Journal of Neuroscience Methods, 218(2):164-169.
Sundararaghavan et al. (Feb. 1, 2009) "Neurite Growth in 3D Collagen Gels with Gradients of Mechanical Properties", Biotechnology and Bioengineering, 102(2):632-643.
Takeuchi et al. (Jul. 7, 2011) "Device for Co-Culture of Sympathetic Neurons and Cardiomyocytes Using Microfabrication", Lab Chip, 11(13):8 pages.
Takeuchi et al. (Dec. 2012) "Sympathetic Neurons Modulate the Beat Rate of Pluripotent Cell-Derived Cardiomyocytes in Vitro", Integrative Biology (Camb), 4(12):1532-1539.
Tan et al., (Feb. 11, 2010) "Neural Bases for Addictive Properties of Benzodiazepines", Nature, 463(7282):16 pages.
Thomson et al. (Feb. 2012) "Using Induced Pluripotent Stem Cells (iPSC) to Model Human Neuromuscular Connectivity: Promise or Reality?", Journal of Anatomy, 220(2):122-130.
Tong et al. (Oct. 2014) "Engineering a Functional Neuro-Muscular Junction Model in a Chip", RSC Advances, 4 (97):54788-54797.
Tonge et al. (Jul. 1997) "Effects of Extracellular Matrix Components on Axonal Outgrowth from Peripheral Nerves of Adult Animals in Vitro", Experimental Neurology, 146(1):81-90.
Ullian et al. (Feb. 2004) "Schwann Cells and Astrocytes Induce Synapse Formation by Spinal Motor Neurons in Culture", Molecular and Cellular Neuroscience, 25(2):241-251.
Umbach et al. (May 2012) "Functional Neuromuscular Junctions Formed by Embryonic Stem Cell-Derived Motor Neurons", PLoS One, 7(5):6 pages.
Uzel et al. (2014) "Microfabrication and Microfluidics for Muscle Tissue Models", Progress in Biophysics and Molecular Biology, 115(2-3):279-293.
Vandenburgh et al. (Apr. 2008) "Drug-Screening Platform Based on the Contractility of Tissue-Engineered Muscle", Muscle & Nerve, 37(4):438-447.
Vandenburgh (Feb. 2010) "High-Content Drug Screening with Engineered Musculoskeletal Tissues", Tissue Engineering Part B: Reviews, 16(1):55-64.
Vandenburgh et al. (Nov. 10, 1996) "Tissue-Engineered Skeletal Muscle Organoids for Reversible Gene Therapy", Human Gene Therapy, 7(17):2195-2200.
Vickerman et al. (Sep. 2008) "Design, Fabrication and Implementation of a Novel Multi Parameter Control Microfluidic Platform for Three-Dimensional Cell Culture and Real-Time Imaging", Lab Chip, 8(9):17 pages.
Wada et al. (Aug. 24, 2009) "Highly Efficient Differentiation and Enrichment of Spinal Motor Neurons Derived from Human and Monkey Embryonic Stem Cells", PLoS One, 4(8):12 pages.
Weick et al. (Nov. 2010) "Functional Control of Transplantable Human ESC-Derived Neurons via Optogenetic Targeting", Stem Cells, 28(11):2008-2016.

(56) References Cited

OTHER PUBLICATIONS

Wichterle et al. (Jun. 2008) "Differentiation of Mouse Embryonic Stem Cells to Spinal Motor Neurons", Current Protocols in Stem Cell Biology, 5(1):1H.1.1-1H.1.9.

Wichterle et al. (Aug. 9, 2002) "Directed Differentiation of Embryonic Stem Cells into Motor Neurons", Cell, 110 (3):385-397.

Williams et al. (Jan. 17, 2014) "A Self-Propelled Biohybrid Swimmer at Low Reynolds Number", Nature Communications, 5(3081):8 pages.

Willits et al. (2004) "Effect of Collagen Gel Stiffness on Neurite Extension", Journal of Biomaterials Science-Polymer Edition, 15(12):19 pages.

Wilson et al. (Jun. 2010) "Measurement of Contractile Stress Generated by Cultured Rat Muscle on Silicon Cantilevers for Toxin Detection and Muscle Performance Enhancement", PLoS One, 5(6):11 pages.

Wyatt et al. (Jun. 2003) "Activity-Dependent Elimination of Neuromuscular Synapses", Journal of Neurocytology, 32(5-8):777-794.

Yaffe et al. (Dec. 22, 1977) "Serial Passaging and Differentiation of Myogenic Cells Isolated from Dystrophic Mouse Muscle", Nature, 270:725-727.

Yizhar et al. (Jul. 14, 2011) "Optogenetics in Neural Systems", Neuron, 71(1):9-34.

Zahavi et al. (Mar. 2015) "A Compartmentalized Microfluidic Neuromuscular Co-Culture System Reveals Spatial Aspects of GDNF Functions", Journal of Cell Science, 128(6):1241-1252.

\* cited by examiner

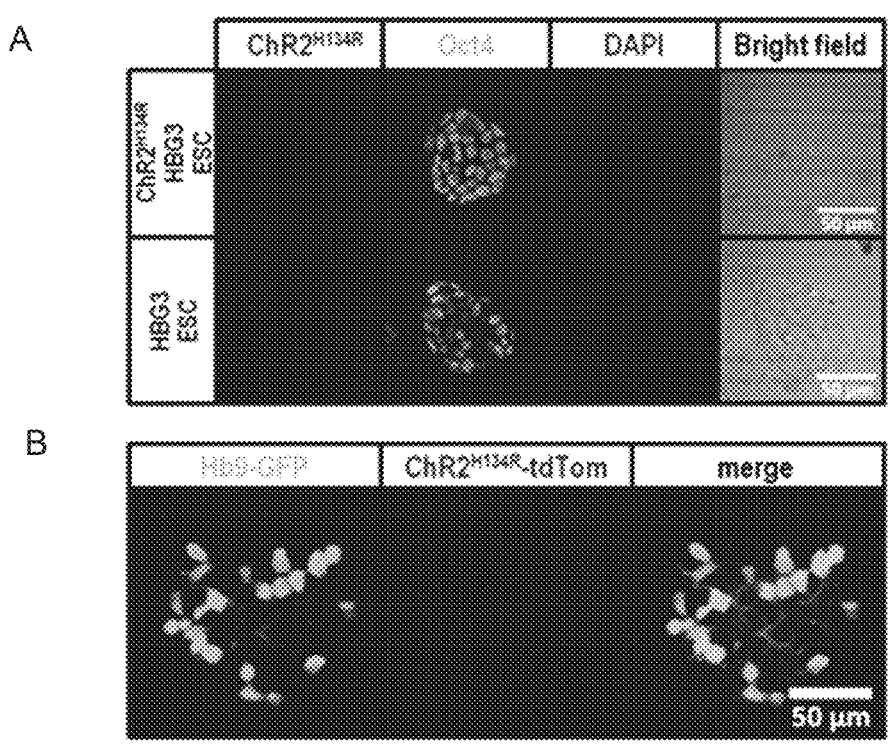
FIGS. 5A-B

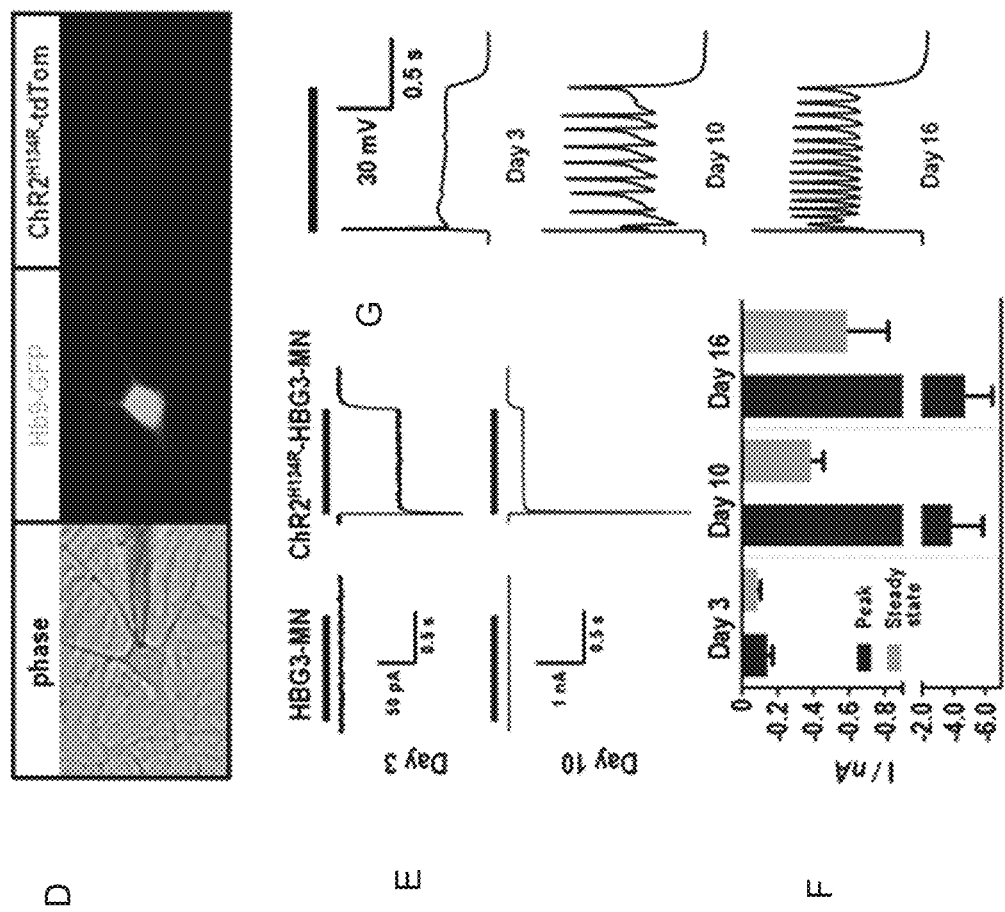
FIGS. 5D-G

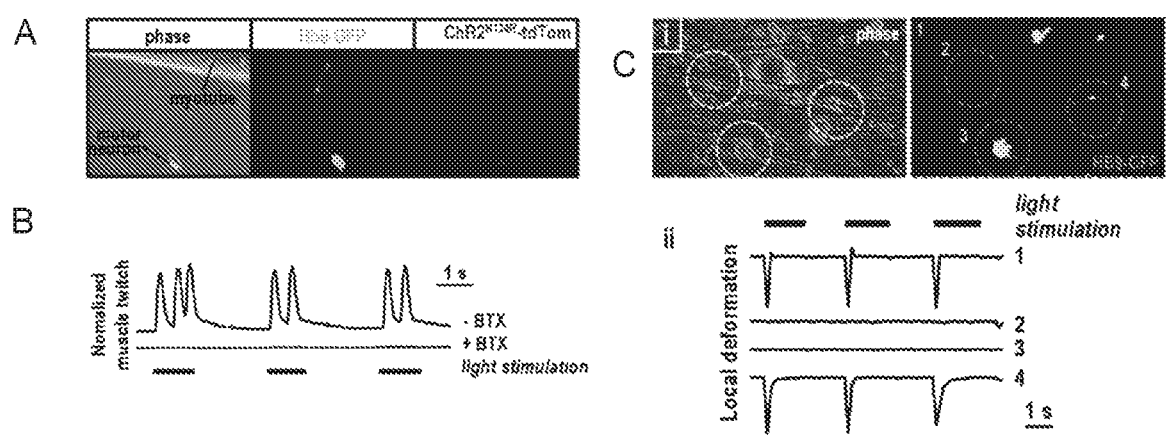
FIGS. 6A-C

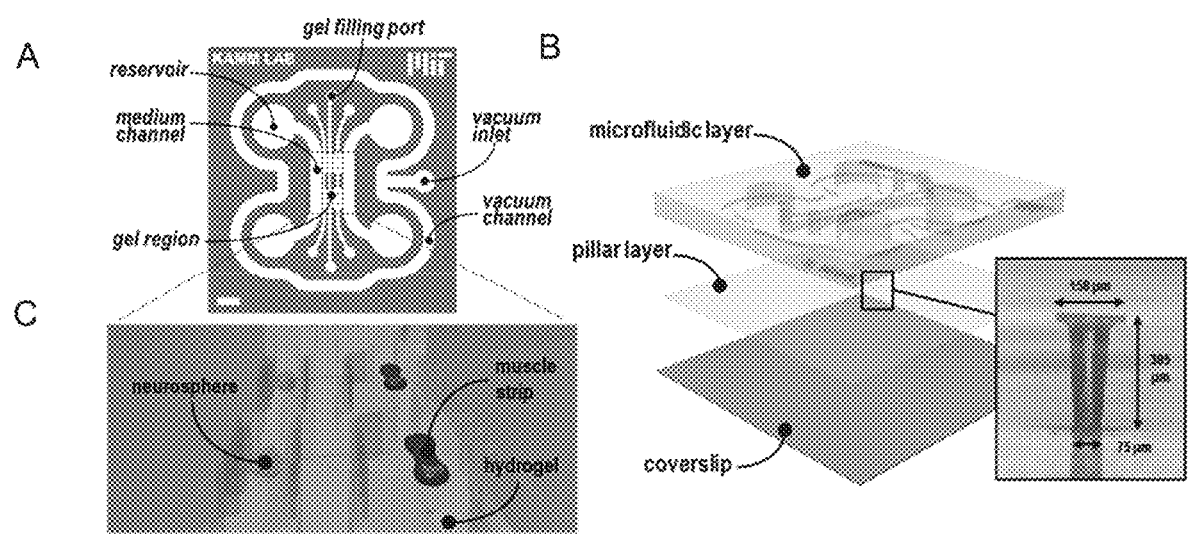
FIGS. 7A-C

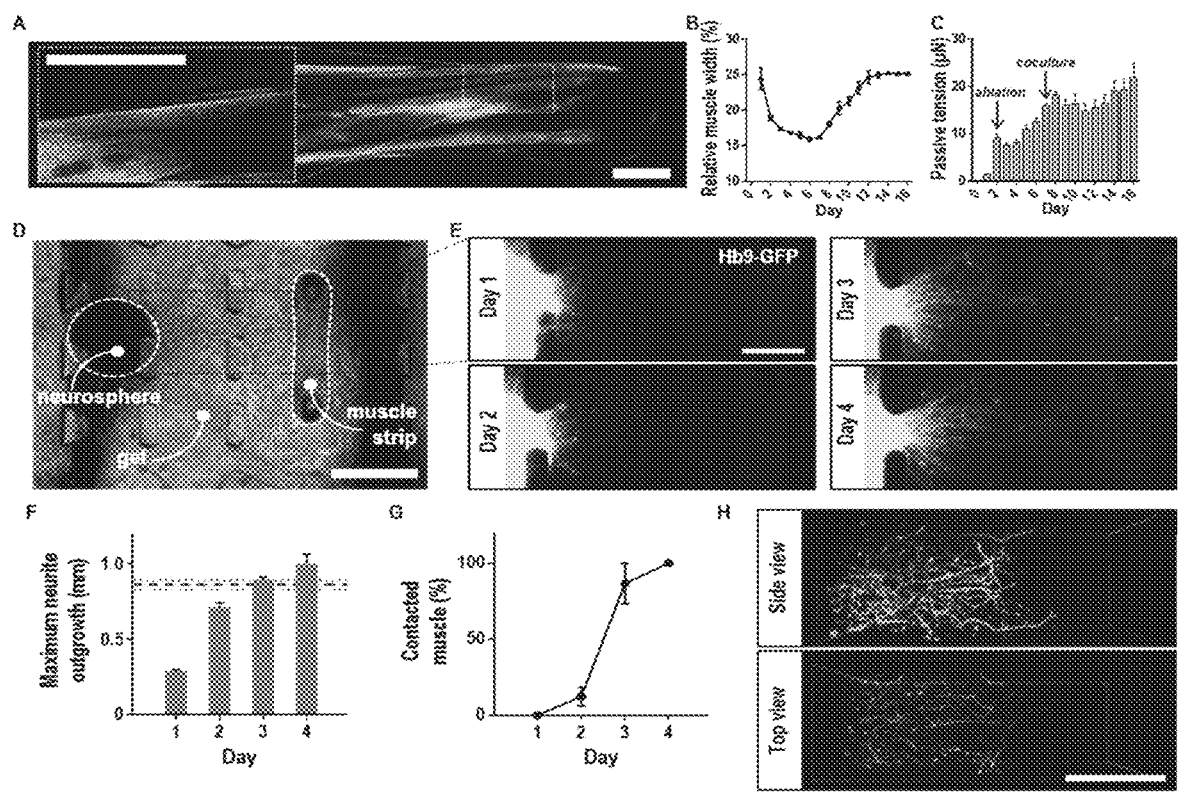
FIGS. 9A-H

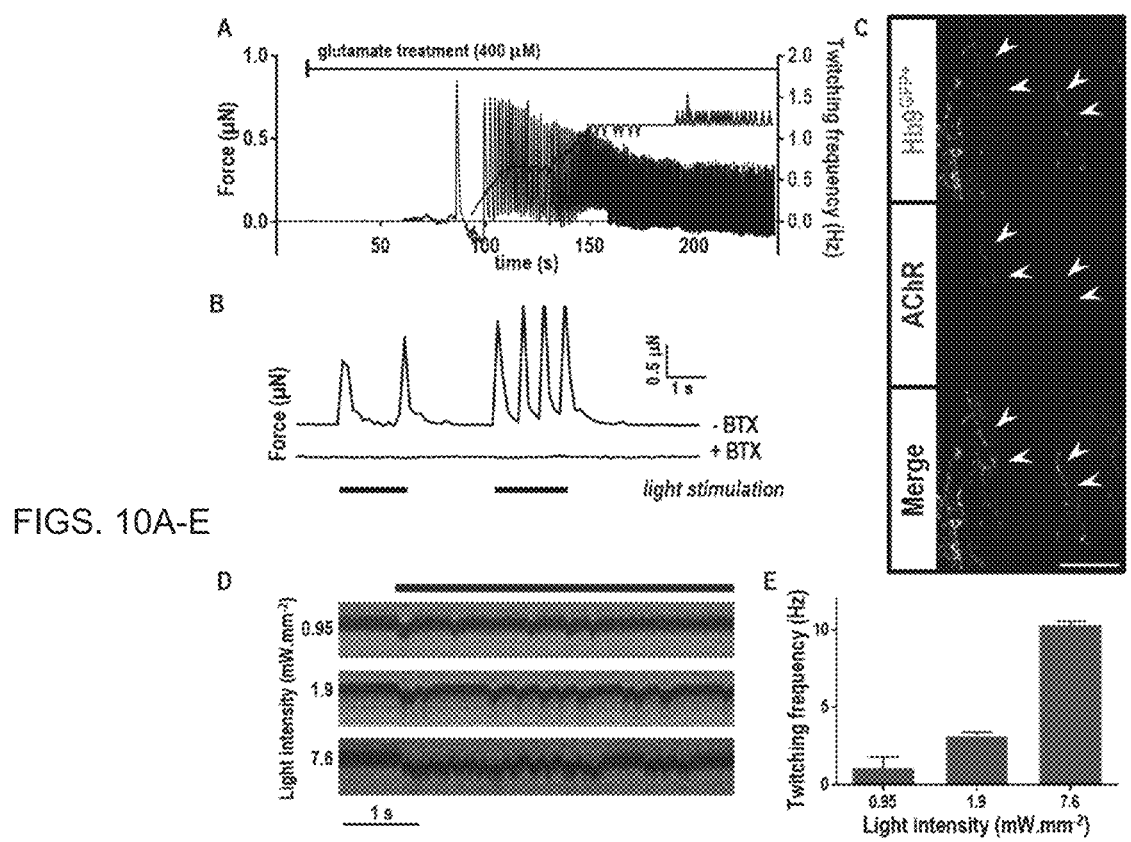
FIGS. 10A-E

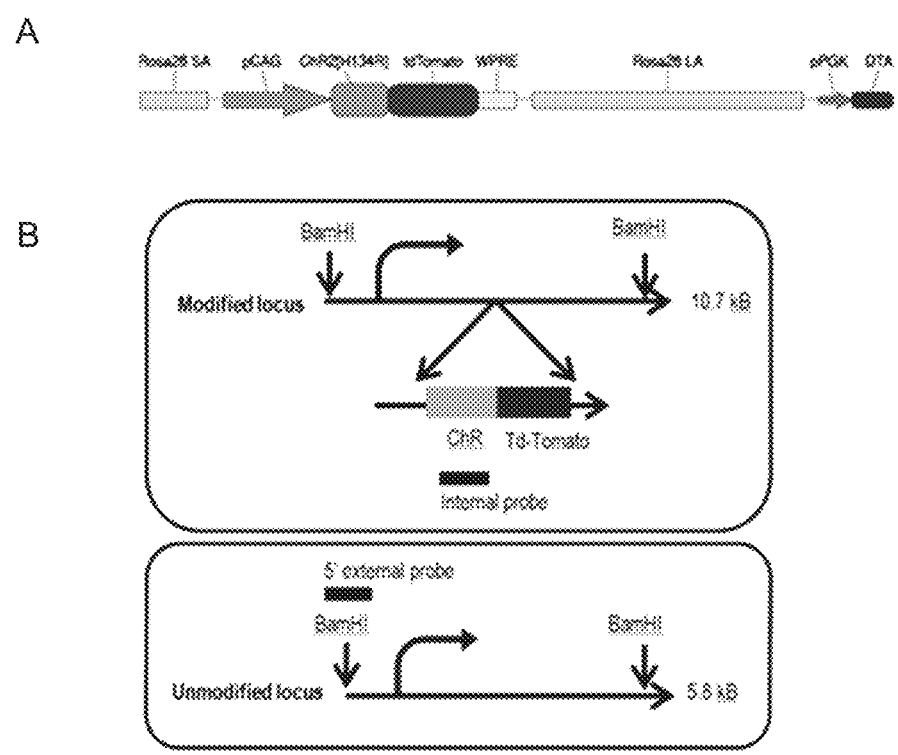
FIGS. 11A-B

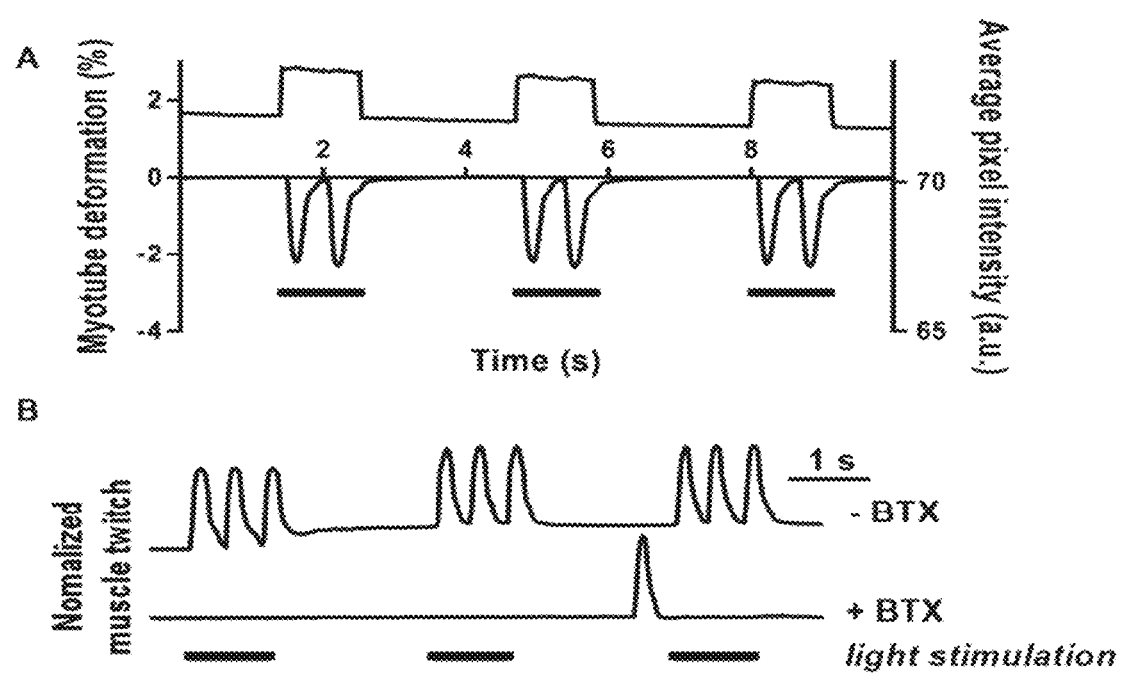
FIGS. 13A-B

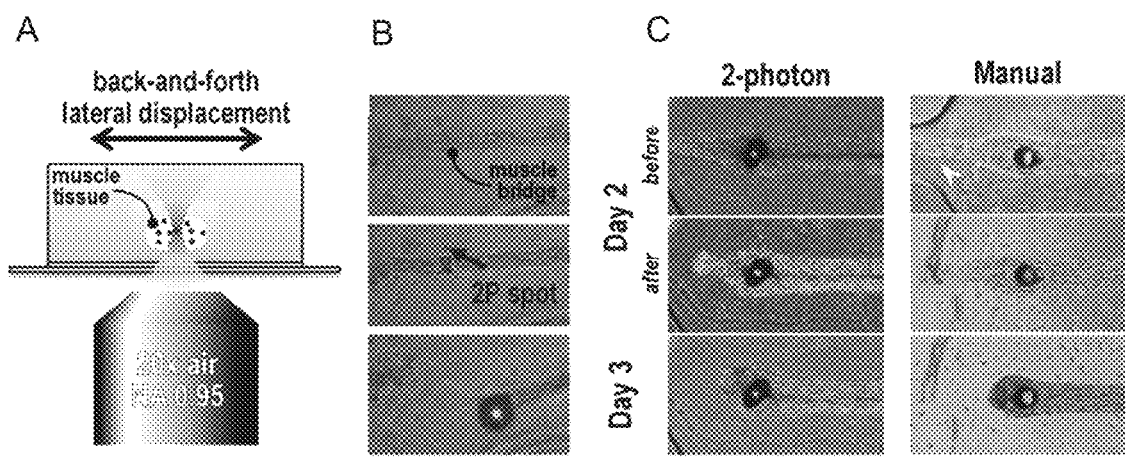
FIGS. 14A-C

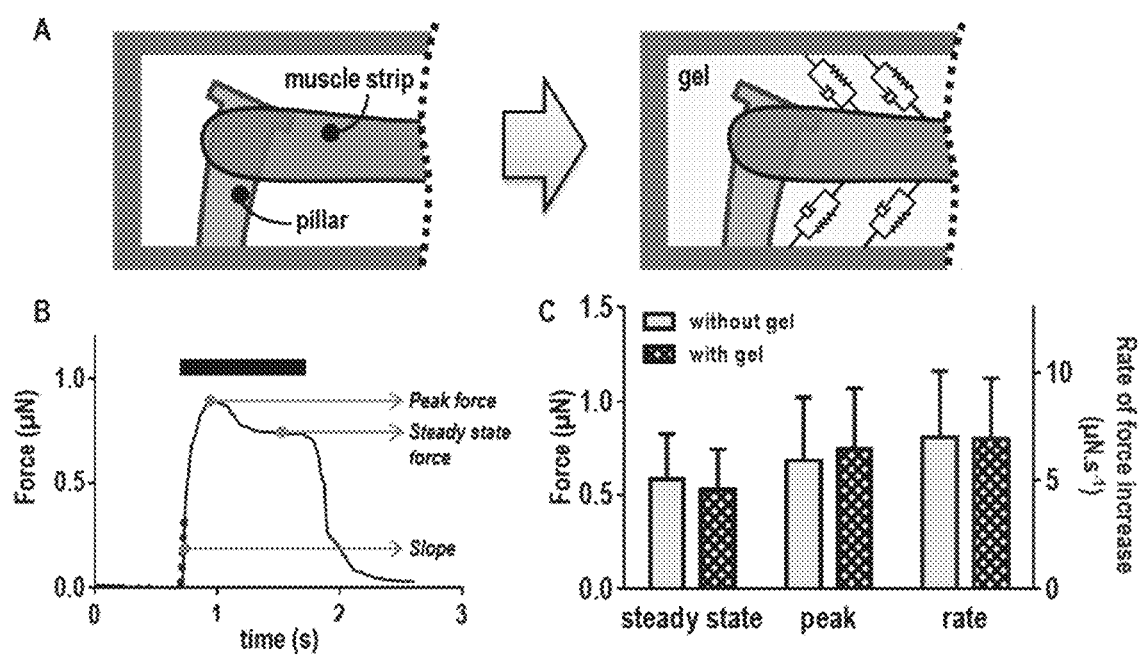
FIGS. 16A-C

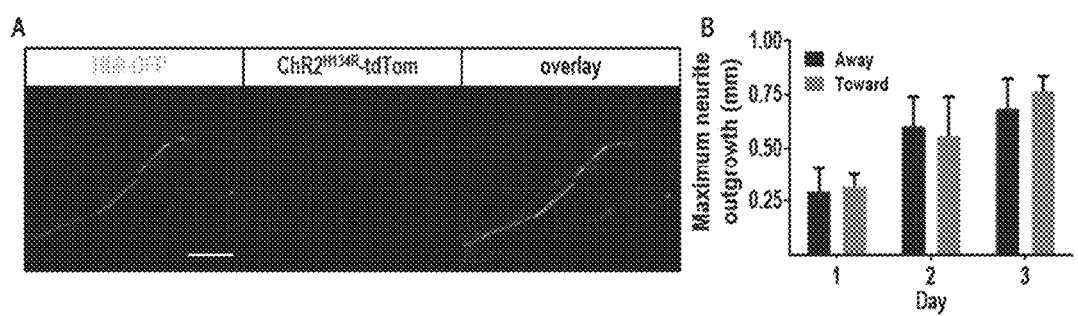
FIGS. 17A-B

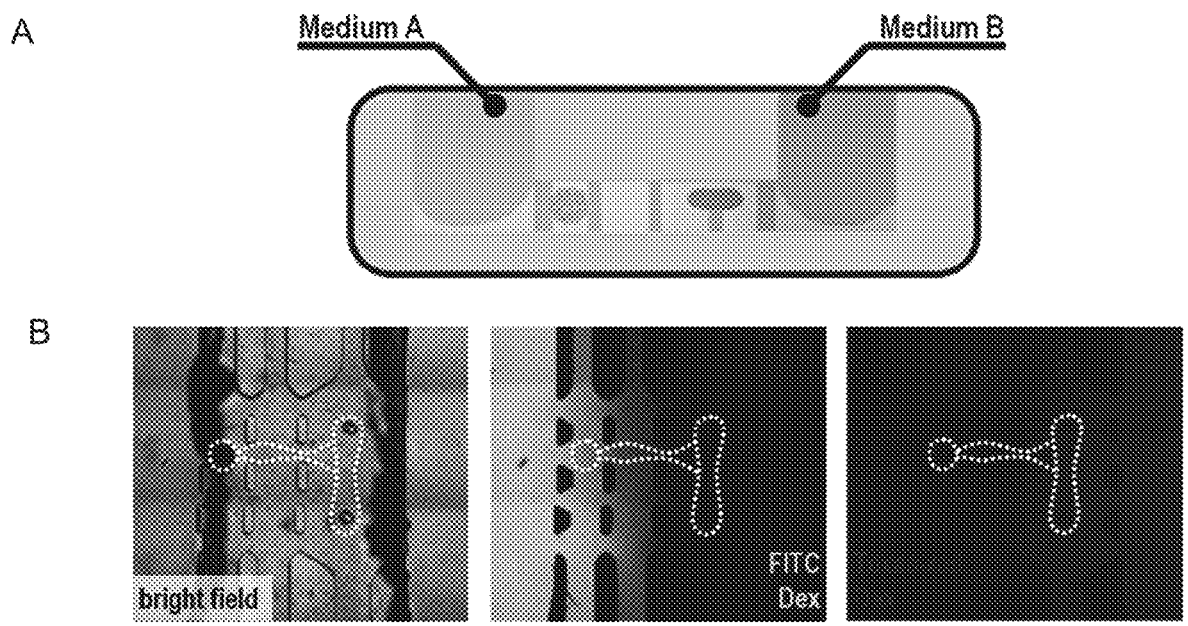
FIGS. 18A-B

SEQUENCE LISTING

```
<160> NUMBER OF SEQ ID NOS: 12

<210> SEQ ID NO 1
<211> LENGTH: 19
<212> TYPE: DNA
<213> ORGANISM: Artificial Sequence
<220> FEATURE:
<223> OTHER INFORMATION: Pou5f1 Forward

<400> SEQUENCE: 1
gctcaccctg ggcgttctc                                                  19

<210> SEQ ID NO 2
<211> LENGTH: 21
<212> TYPE: DNA
<213> ORGANISM: Artificial Sequence
<220> FEATURE:
<223> OTHER INFORMATION: Pou5f1Reverse

<400> SEQUENCE: 2
ggccgcagct tacacatgtt c                                               21

<210> SEQ ID NO 3
<211> LENGTH: 20
<212> TYPE: DNA
<213> ORGANISM: Artificial Sequence
<220> FEATURE:
<223> OTHER INFORMATION: Klf4 Forward

<400> SEQUENCE: 3
caggctgtgg caaaacctat                                                 20
```

```
<210> SEQ ID NO 4
<211> LENGTH: 20
<212> TYPE: DNA
<213> ORGANISM: Artificial Sequence
<220> FEATURE:
<223> OTHER INFORMATION: Klf4 Reverse

<400> SEQUENCE: 4
cgtcccagtc acagtggtaa                                        20

<210> SEQ ID NO 5
<211> LENGTH: 20
<212> TYPE: DNA
<213> ORGANISM: Artificial Sequence
<220> FEATURE:
<223> OTHER INFORMATION: Nanog Forward

<400> SEQUENCE: 5
aagtacctca gcctccagca                                        20

<210> SEQ ID NO 6
<211> LENGTH: 20
<212> TYPE: DNA
<213> ORGANISM: Artificial Sequence
<220> FEATURE:
<223> OTHER INFORMATION: Nanog Reverse

<400> SEQUENCE: 6
gtgctgagcc cttctgaatc                                        20

<210> SEQ ID NO 7
<211> LENGTH: 20
<212> TYPE: DNA
<213> ORGANISM: Artificial Sequence
<220> FEATURE:
<223> OTHER INFORMATION: Sox2 Forward

<400> SEQUENCE: 7
agggctggga gaaagaagag                                        20

<210> SEQ ID NO 8
<211> LENGTH: 20
<212> TYPE: DNA
<213> ORGANISM: Artificial Sequence
<220> FEATURE:
<223> OTHER INFORMATION: Sox2 Reverse

<400> SEQUENCE: 8
atctggcgga gaatagttgg                                        20

<210> SEQ ID NO 9
<211> LENGTH: 20
<212> TYPE: DNA
<213> ORGANISM: Artificial Sequence
<220> FEATURE:
<223> OTHER INFORMATION: Esrrb Forward

<400> SEQUENCE: 9
gaacactctc gcctggtagg                                        20

<210> SEQ ID NO 10
<211> LENGTH: 20
<212> TYPE: DNA
<213> ORGANISM: Artificial Sequence
<220> FEATURE:
<223> OTHER INFORMATION: Esrrb Reverse
```

```
<400> SEQUENCE: 10
cgcctccagg ttctcaatgt                                                  20

<210> SEQ ID NO 11
<211> LENGTH: 20
<212> TYPE: DNA
<213> ORGANISM: Artificial Sequence
<220> FEATURE:
<223> OTHER INFORMATION: PCR Forward Primer

<400> SEQUENCE: 11
tcctggtccc tgaggatcaa                                                  20

<210> SEQ ID NO 12
<211> LENGTH: 20
<212> TYPE: DNA
<213> ORGANISM: Artificial Sequence
<220> FEATURE:
<223> OTHER INFORMATION: PCR Reverse Primer

<400> SEQUENCE: 12
gcggaacgga gatcgaggtc                                                  20
```

MICROFLUIDIC DEVICE FOR THREE DIMENSIONAL AND COMPARTMENTALIZED COCULTURE OF NEURONAL AND MUSCLE CELLS, WITH FUNCTIONAL FORCE READOUT

CROSS REFERENCE TO RELATED APPLICATION

This application claims priority to, and the benefit of U.S. Provisional Application No. 62/349,270, filed Jun. 13, 2016, the entire content of which is incorporated herein by reference in its entirety.

STATEMENT REGARDING FEDERALLY SPONSORED RESEARCH OR DEVELOPMENT

This invention was made with government support under Grant No. CBET-0939511 awarded by the National Science Foundation. The government has certain rights in the invention.

INCORPORATED BY REFERENCE OF SEQUENCE LISTING

The contents of the text filed named 38172-515001US_ST25.TXT, which was created on Aug. 30, 2017, and is 2,630 bytes in size, are hereby incorporated by reference in their entireties.

TECHNICAL FIELD

The subject matter described herein relates to a microfluidic device for the coculture of neuronal and muscle cells.

BACKGROUND

A neurosphere is a culture system composed of free-floating clusters of neural stem cells. Since neural stem cells are not yet studied in vivo, neurospheres provide a method to investigate neural precursor cells in vitro. Putative neural stem cells are suspended in a medium lacking adherent substrates but containing necessary growth factors, such as epidermal growth factor and fibroblast growth factor. This allows the neural stem cells to form into the characteristic three-dimensional (3D) clusters.

When neurospheres are placed in a co-culture alongside muscle cells and under appropriate conditions, an axon may form between the neurospheres and the muscle cells. However, existing three-dimensional assay systems lack means for (i) precise positioning of the motor neuron containing neurospheres with respect to the muscle bundle, which results in significant sample-to-sample variation; and for (ii) compartmentalization, which limits the ability to visualize axon outgrowth or supply or stimulate each tissue type selectively.

SUMMARY

The present subject matter provides microfluidic devices that enable the precise and repeatable three-dimensional and compartmentalized coculture of muscle cells and neuronal cells. The muscle cells form muscle bundles in the device, and the muscle bundles are innervated with axons. The neuronal cells may be, e.g., within one or more neurospheres. When cultured on adherent substrates or in a three-dimensional extracellular matrix (ECM), and under appropriate conditions, neurites spontaneously extend out of the neurospheres. One neurite eventually becomes an axon, and when the motile tip of the axon, the growth cone, comes in contact with a muscle cell, a synapse, called neuromuscular junction, can form.

The microfluidic device can include a plurality, e.g., a series, of coculture chambers, each coculture chamber having a neuronal culture compartment including one or more retaining features that keep the neuronal cells (e.g., in a neurosphere) within the neuronal culture compartment. Non-limiting examples of retaining features include compartment walls with openings for an axon to pass through, pillars, a net (e.g., a rigid netting or mesh of plastic or other material), or plates. In some embodiments, the retaining features are arranged so as to form a concave portion or boundary of the neuronal culture compartment. In some embodiments, the retaining feature is a pillar cup. The coculture chamber may further include a muscle cell culture compartment including one or more compliant pillars.

In various embodiments, the coculture chamber also includes a buffer compartment separating the neuronal cell compartment and the muscle cell compartment. In some embodiments, the device includes a series of coculture chambers, which include a neuron chamber featuring retaining pillars acting as a cup for the neurospheres, a muscle cell culture compartment including one or more compliant anchor pillars for muscular tissue to wrap around, and a buffer compartment separating the neuronal cell compartment and the muscle cell compartment. In certain embodiments, two large reservoirs flank the tissue culture chambers (e.g., the neuronal cell compartment and the muscle cell compartment) and allow for the supply of medium and chemical cues.

When the device is seeded with muscle cells and appropriate conditions are applied, a muscle bundle may form in the muscle cell culture compartment and wrap around the compliant pillars. For example, the muscle bundle may wrap around two compliant pillars, and completely span the distance between the compliant pillars. The compliant pillars may, e.g., comprise a cap structure (e.g., in the shape of a square, sphere, or slab) or may be continuous from the floor to the ceiling of the chamber so as to prevent the muscle bundle from slipping off the compliant pillars. Likewise, when the device is seeded with neuronal cells, such as neuro spheres, and appropriate conditions applied, neurites may extend out of the neurospheres, navigate through the extracellular matrix across the buffer compartment and reach the muscle bundle, where they form three-dimensional neuromuscular junctions. Upon stimulation of the neuronal cells, the muscle bundle will contract, demonstrating the presence of functional neuromuscular junctions.

In various embodiments, a neurosphere can range between 100 μm to 2 mm in diameter. In some embodiments, a neurosphere contains about 1,000 to 1,000,000 or more cells. Neuronal cells and muscle cells may be cultured, e.g., in a hydrogel. The hydrogel material may be the same throughout each coculture chamber (e.g., in the first, second, and buffer compartments). In some embodiments, when the muscle chamber is seeded, the hydrogel contains between 2,000,000 to 10,000,000 cells/ml of hydrogel. In certain embodiments in which the muscle chamber has a volume of about one microliter, the chamber may initially contain, e.g., about 2,000 to 10,000 cells.

Non-limiting examples of neurons that may be used in various embodiments of the present subject matter include cells forming neuromuscular junctions with muscle cells in primary tissue; spinal cord explants; and autonomic ganglia.

In some embodiments, cells that have been differentiated from pluripotent cells (e.g., motor neurons derived from embryonic stem cells or induced pluripotent stem cells) may be used. Non-limiting examples of muscle cells that may be used in various embodiments include cells dissociated from organs constituting the muscular system, such as from the heart (cardiac cells), limb or body wall muscles (skeletal muscle cells), and visceral muscle (smooth muscle cells). In certain embodiments, the cells comprise a myoblast cell line such as C2C12 (ATCC).

Axons can grow to be several millimeters long in vitro, including in devices of the present subject matter (and up to about a meter in vivo). In non-limiting in vitro systems and devices exemplified herein, axons were observed extending at a maximum rate of ~10 micron/hour. In various embodiments, axons extend in all directions. In some embodiments, a device or chamber of a device of the present subject matter comprises one or more factors that attracts and/or repels axons. For example, Netrin and nerve growth factor (NGF) are examples of soluble chemoattractants, and Slit or semaphorins are known chemorepellant. Also, Glial cell-derived neurotrophic factor (GDNF) was found to increase the rate of axon outgrowth. In addition, one or more factors that attracts and/or repels axons can be applied in a gradient using the two medium reservoirs.

The compliant pillars are deflectable and when wrapped by the muscle bundle will deflect when the muscle bundle contracts. Deflection by the compliant pillars allows for measurement of the force generated by the muscle bundle when the muscle bundle contracts. These integrated compliant pillars are a means to non-invasively and passively measure the force generated by the muscle bundle.

The compliant pillars are deflectable/deformable. For example, the stiffness of exemplary posts was found to be approximately 0.36±0.08 µN·µm-1. Stiffness of the pillar(s) can vary. As a non-limiting example, the stiffness can vary between about 0.20 µN·µm-1 and about 0.50 µN·µm-1, and more preferably between about 0.28 µN·µm-1 and about 0.45 µN·µm-1. The Young's modulus of material(s) of the pillar(s) can also vary, as well. For example, the Young's modulus can vary between about 500 kPa to about 1.5 MPa, and more preferably about 580 kPa to about 1 MPa. Deflection(s) of the pillar(s) can be measured between a variety of values. As a non-limiting example, deflection can be measured between about 0.1 µm and about 200 µm, and more preferably between about 0.1 µm and about 50 µm.

In some embodiments, the first culture compartment can have a width of at least 100 µm. In some embodiments, the width of the first culture compartment is about 100 µm, 500 µm, 1.25 mm, 1.5 mm, 1.75 mm, 2 mm, 2.5 mm, 3 mm, 4 mm, or 5 mm. In some embodiments, the width of the first culture compartment is less than about 500 µm, 1.25 mm, 1.5 mm, 1.75 mm, 2 mm, 2.5 mm, 3 mm, 4 mm, or 5 mm.

In some embodiments, the second culture compartment can have a width of at least 100 µm. In some embodiments, the width of the second culture compartment can be about 100 µm, 500 µm, 1.25 mm, 1.5 mm, 1.75 mm, 2 mm, 2.5 mm, 3 mm, 4 mm, or 5 mm. In some embodiments, the width of the second culture compartment is less than about 500 µm, 1.25 mm, 1.5 mm, 1.75 mm, 2 mm, 2.5 mm, 3 mm, 4 mm, or 5 mm.

In some embodiments, the one or more compliant pillars have a height of at least 50 µm. In some embodiments, the height is about 50 µm, 100 µm, 150 µm, 250 µm, 260 µm, 270 µm, 280 µm, 290 µm, 300 µm, 310 µm, 320 µm, 330 µm, 340 µm, 350 µm, 1 mm, or 1.5 mm. In some embodiments, the height is less than 100 µm, 150 µm, 250 µm, 260 µm, 270 µm, 280 µm, 290 µm, 300 µm, 310 µm, 320 µm, 330 µm, 340 µm, 350 µm, 1 mm, or 1.5 mm.

In some embodiments, the first culture compartment, the second culture compartment, or the buffer compartment includes a volume of at least 650 µm$^3$. In some embodiments, the first culture compartment, the second culture compartment, or the buffer compartment includes a volume of about 650 µm$^3$, 700 µm$^3$, 750 µm$^3$, 800 µm$^3$, 850 µm$^3$, 900 µm$^3$, 950 µm$^3$, 1600 µm$^3$, or 2100 µm$^3$.

In some embodiments, an escape channel is included between an end of the second chamber and a reservoir, the escape channel allowing passage of gas during a hydrogel injection process.

The subject matter described herein provides many technical advantages. For example unlike conventional two-dimensional cell monolayer systems, the microfluidic device described herein enables coculture of neurospheres and muscle bundles and allows for the formation of three-dimensional neuromuscular junctions in a microenvironment that mimics that of an in vivo counterpart. The microfluidic device or platform provides three dimensional and compartmentalized coculture. Spatial segregation of the two cell types provides a unique opportunity to visualize the three-dimensional axon outgrowth towards the muscle. In various embodiments, the three dimensional coculture of cells comprises one or more hydrogels. In addition, the microfluidic device enables quantitative measurement of force generated by muscle tissues. The presence of several identical coculture chambers per microfluidic device and the geometrical configuration matching the dimensions of multichannel pipettors facilitates formation of multiple parallel cultures in order to increase throughput while maintaining a user friendly seeding procedure. Further, the microfluidic device allows for the generation of chemical cues in the form of concentration gradients, capable of emulating a distribution of factors as found in the body.

Further technical advantages include a microfluidic device for repeatable and precise positioning of the motor neuron containing neurospheres with respect to the muscle bundle, which reduces experimental sample-to-sample variation. The integrated compliant pillar technology can be a means to non-invasively and passively measure the force generated by the muscle bundle. The presence of the hydrogel all around the neurospheres and muscle bundles not only provides a physical bridge to allow for axon outgrowth towards their muscle target, but it recapitulates the compliant and extracellular matrix (ECM) rich microenvironment encountered in vivo.

In some embodiments, the device comprises a plurality of co-culture chambers that are separate from one another. Thus, each chamber can be manipulated (e.g., filled with different materials) independently. Moreover, the design and manufacture of the device is simplified. The separate nature of the muscle chamber along with an entry necking region results in individual untethered and freely moving muscle tissues.

In some embodiments, the device comprises a muscle chamber shaped so that hydrogel injected (in its liquid state) can be pushed to the limit of the muscle chamber, and not further. An escape channel, which may be formed as small L-shaped channel, evacuates any air bubble that might form during the hydrogel injection process. The dead-end nature of the muscle chamber along with a constriction feature or entry necking region results in individual untethered and freely moving muscle tissues.

The microfluidic device provides an ability to provide cell-specific media or generate gradients of growth factors, in order to mimic the chemical microenvironment found in vivo. Moreover, the composition of the hydrogel (mimicking an extracellular matrix) can be tuned to include some ligands of interest or to vary the mechanical properties, so long as axon formation is not prevented. Finally, the use of microfluidic devices of the present subject matter for such cell culture allows cell maintenance, treatment, and image acquisition to be automated.

Hydrogel compositions encompass a group of polymeric materials, the hydrophilic structure of which renders them capable of holding large amounts of water in their three-dimensional networks. Polymers from which hydrogels are made may be naturally-occurring, e.g., purified from a natural source, or synthetic, e.g., chemically-synthesized. The polymers may be water soluble or water insoluble. The ability of hydrogels to absorb water arises from hydrophilic functional groups attached to the polymeric backbone, while their resistance to dissolution arises from cross-links between network chains. The crosslinks may be chemical or physical; polymer crosslinks include covalent crosslinks, ionic crosslinks, hydrogen bonds, and/or hydrophobic interactions. Hydrogel-forming natural polymers include purified proteins such as collagen and gelatin and purified polysaccharides such as starch, alginate, and agarose. Synthetic polymers that form hydrogels are prepared using chemical polymerization/synthesis methods. Hydrogels may be one, two- or multi-component systems consisting of a three-dimensional network of polymer chains and water that fills the space between polymer macromolecules.

In some embodiments, hydrogel can include a network of polymer chains that are water-insoluble. Hydrogel can include a water-swollen and cross-linked polymeric network produced by a reaction of one or more monomers. Hydrogel can include polymeric material that exhibits the ability to swell and retain a significant fraction of water within its structure, but will not dissolve in water. Hydrogel can include a colloidal gel in which water is the dispersion medium. Their hydrophilic structure renders them capable of holding large amounts of water in their three-dimensional networks (e.g., hydrogels can be super absorbent and can contain 50%, 75%, 90%, 95% and over 99% water). Hydrogels can include natural and/or synthetic polymers. Hydrogels can possess a degree of flexibility very similar to natural tissue, due to their significant water content.

In a non-limiting example, a hydrogel comprises collagen. Various concentrations of collagen may be used. For example, a concentration of about 1, 2, 3, 4, 5, 6, 7, 8, 9, 10, or 1-10 mg/ml or more of collagen in an aqueous solution (such as cell culture medium, saline, or water) may be used. The collagen-containing hydrogel optionally also includes one or more of the following proteins: laminin, entactin, heparan sulfate proteoglycans, which are characterized by adhesive properties, as well as growth factors such as TGF-beta and EGF. An example of such a collagen-containing hydrogel includes Matrigel. Thus in some embodiments, the hydrogel comprises Matrigel (gelatinous protein mixture derived from mouse tumor cells) or an equivalent thereof. Matrigel is the trade name for a gelatinous protein mixture secreted by Engelbreth-Holm-Swarm (EHS) mouse sarcoma cells that is produced and marketed by Corning Life Sciences. Thus "Matrigel" may be substituted with a gelatinous protein mixture from another natural, synthetic, or commercial source. Matrigel or a substitute of Matrigel may be used, e.g., in a 1:1, 1:2, 1:3, 1:4, 1:5, 1:6, 1:7, 1:8, 1:9, 1:10 Matrigel:collagen or collagen:Matrigel ratio.

In some embodiments, the hydrogel comprises an alginate or a derivative thereof, gelatin, collagen, agarose, a natural or synthetic polysaccharide, polylactic acid, polyglycolic acid, poly(lysine), a polyanhydride; a poly(lactide-co-glycolide) (PLGA) polymer, a polyamino acid, a poly(alkylene oxide), a poly(ethylene oxide), a poly(allylamine)(PAM), a poly(acrylate), a polyester, polyhydroxybutyrate and poly-epsilon-caprolactone, a polyphosphazine, a poly(vinyl alcohol), a modified styrene polymer, poly(4-aminomethylstyrene), a pluronic polyol, a polyoxamer, a poly(uronic acid), a poly(vinylpyrrolidone), and/or a copolymer comprising one or more of an alginate or a derivative thereof, gelatin, collagen, agarose, a natural or synthetic polysaccharide, polylactic acid, polyglycolic acid, poly(lysine), a polyanhydride; a poly(lactide-co-glycolide) (PLGA) polymer, a polyamino acid, a poly(alkylene oxide), a poly(ethylene oxide), a poly(allylamine)(PAM), a poly(acrylate), a polyester, polyhydroxybutyrate and poly-epsilon-caprolactone, a polyphosphazine, a poly(vinyl alcohol), a modified styrene polymer, poly(4-aminomethylstyrene), a pluronic polyol, a polyoxamer, a poly(uronic acid), and a poly(vinylpyrrolidone).

In an aspect, a microfluidic device is for coculture of muscle cells and neuronal cells for innervating a muscle bundle with an axon. The microfluidic device includes a coculture chamber including a first culture compartment, a second culture compartment, and a buffer compartment. The first culture compartment includes one or more retaining features. The second culture compartment includes one or more compliant pillars. The buffer compartment separates the first compartment and the second compartment. The compliant pillars are deflectable to measure force generated by the muscle bundle. In various embodiments, a "buffer compartment" refers to a compartment between a compartment that contains neuronal cells and a compartment that contains muscle cells. The buffer compartment need not contain a different hydrogel or buffer (pH-balanced solution) than any other compartment. For example, the buffer compartment may be a region that is filled with the same hydrogel that is used to culture/surround the neurons and the muscle cells. Thus, in various embodiments, the purpose of the "buffer compartment" is to physically segregate the neurons from the muscle and offer a window/region for visualizing axonal outgrowth. Without the buffer compartment, the muscle chamber would be directly adjacent to the neuron chamber, and natural tissue spreading could result in direct contact between the neuronal cells and muscle cells.

One or more of the features disclosed herein can be included in a device in any feasible combination. For example, in some embodiments, retaining features can include rigid pillars positioned in a substantially concave arrangement, the first culture compartment can contain a neuronal cell culture, the second culture compartment can contain a muscle cell culture, and the buffer compartment can contain a hydrogel but no cells, or cells other than the muscle and neuronal cells. In some embodiments, an axon can extend from the first culture compartment through the buffer compartment to the second culture compartment and form a neuromuscular junction with the muscle cells. In various embodiments, the first culture compartment, the second culture compartment, and/or the buffer compartment can contain a hydrogel.

In some embodiments, hydrogel can include a network of polymer chains that are water-insoluble. Hydrogel can include a water-swollen and cross-linked polymeric network produced by a reaction of one or more monomers. Hydrogel can include polymeric material that exhibits the ability to swell and retain a significant fraction of water within its structure, but will not dissolve in water. Hydrogel can include a colloidal gel in which water is the dispersion medium. Their hydrophilic structure renders them capable of holding large amounts of water in their three-dimensional networks (e.g., hydrogels can be super absorbent and can contain over 99% water). Hydrogels can include natural and/or synthetic polymers. Hydrogels can possess a degree of flexibility very similar to natural tissue, due to their significant water content.

In a non-limiting example, a hydrogel comprises collagen. Various concentrations of collagen may be used. For example, a concentration of about 1, 2, 3, 4, 5, 6, 7, 8, 9, 10, or 1-10 mg/ml or more of collagen in an aqueous solution (such as cell culture medium, saline, or water) may be used. In some embodiments, the hydrogel comprises Matrigel or an equivalent thereof. Matrigel is the trade name for a gelatinous protein mixture secreted by Engelbreth-Holm-Swarm (EHS) mouse sarcoma cells that is produced and marketed by Corning Life Sciences. Thus "Matrigel" may be substituted with a gelatinous protein mixture secreted by Engelbreth-Holm-Swarm (EHS) mouse sarcoma cells from another commercial source. Matrigel or a substitute of Matrigel may be used, e.g., in a 1:1, 1:2, 1:3, 1:4, 1:5, 1:6, 1:7, 1:8, 1:9, 1:10 Matrigel:collagen or collagen:Matrigel ratio.

In various implementations of the present subject matter, the microfluidic device comprises one or more neuronal inlet injection ports for seeding the first culture compartment with neuronal cells. One or more muscle inlet injection ports can be included for seeding the second culture compartment with muscle cells. In various embodiments, a microfluidic device can include a plurality of coculture chambers, the coculture chambers being separated from each other by the minimal tip distance between the individual pipettes of a multichannel pipettor. The use of a multichannel pipettor facilitates multiplexing cell culture maintenance and treatment administration. In some embodiments, the plurality of coculture chambers includes six or more coculture chambers.

In certain embodiments, the microfluidic device includes a first medium reservoir adjacent the first culture compartment, and a second medium reservoir adjacent the second culture compartment. When filled with culture medium, these reservoirs allow for, e.g., the supply of nutrients, the removal of waste and the administration of chemical cues. If two distinct conditions are supplied to the first and second reservoirs, chemical concentration gradients will form by diffusion within the hydrogel and expose each compartment to a specific condition.

The second culture compartment can be seeded with muscle cells to enable growth of the muscle bundle. The muscle bundle can wrap around the compliant pillars. The first culture compartment can be seeded with neuronal cells to enable growth of the neurites from the first culture compartment through the buffer compartment to the second culture compartment and form neuromuscular junctions with the muscle bundle. The neuronal cells can be stimulated. When functional neuromuscular junctions are present, the stimulation of the neuronal cells can elicit the contraction of the muscle bundle. The contraction of the muscle bundle causes deflection of the compliant pillars around which it is wrapped. The amount of deflection can be converted into a level of force generated by the muscle bundle, providing that the mechanical stiffness of the pillars is known. Aspects of the present subject matter provide a microfluidic device for coculture of a muscle cell and a neuronal cell, the microfluidic device comprising a coculture chamber comprising a first culture compartment including one or more retaining features; a second culture compartment including one or more compliant pillars; and a buffer compartment separating the first compartment and the second compartment; wherein the compliant pillars are deflectable to measure force. In various embodiments, the device is for innervating a muscle bundle formed by muscle cells and measuring force generated by the muscle bundle.

In some embodiments, innervating a muscle bundle comprises one or more of (a) growth of neurites into contact with the external surface of the muscle bundle; (b) growth of neurites past the external surface and into the muscle bundle; and (c) formation of a neuromuscular junction between an axon and a muscle cell of the muscle bundle. In some embodiments, the one or more retaining features comprise a rigid substantially concave barrier.

In some embodiments, the barrier comprises (a) about 1, 2, 3, 4, 5, 6, 7, 8, 9, 10 or more are pillars or plates positioned in a substantially concave arrangement; or (b) a substantially concave wall with slits, holes, or openings too small for a neuron or neurosphere to pass through but large enough for an axon to pass through.

In some embodiments, the first culture compartment contains a neuronal cell, the second culture compartment contains a muscle cell, and the buffer compartment contains a hydrogel.

In some embodiments, the first culture compartment, the second culture compartment, and the buffer compartment contain a hydrogel.

In some embodiments, the first culture compartment, the second culture compartment, and the buffer compartment contain the same hydrogel.

In some embodiments, the hydrogel in the first culture compartment, the second culture compartment, and/or the buffer compartment contains a cell other than the neuronal cell or the muscle cell.

In some embodiments, the cell comprises a Schwann cell, a satellite cell, an endothelial cell, or a glial cell.

In some embodiments, the neuronal cell comprises a photosensitized cell.

In some embodiments, the neuronal cell comprises a patient-derived neuronal cell.

In some embodiments, the patient-derived neuronal cell is from a patient who has been diagnosed with amyotrophic lateral sclerosis (ALS) or spinal muscular atrophy (SMA).

In some embodiments, the neuronal cell (a) is within a neurosphere; (b) comprises a neural stem cell; (c) comprises a neuron; (d) comprises an interneuron; (e) comprises a sensory neuron; and/or (f) comprises a motor neuron.

In some embodiments, the neurosphere (a) comprises about 1 to 1000, 100,000 to 10,000,000, 1000 to 1,000,000, or more than 1,000,000 neurons; (b) comprises a dimension of about 50-2000 microns at its widest diameter; (c) comprises embryonic neural stem cells; (d) comprises induced pluripotent neural stem cells; and/or (e) comprises a neuron, an astrocyte, and/or an oligodendrocyte.

In some embodiments, the muscle cell (a) is within a muscle bundle; (b) comprises a myoblast; and/or (c) comprises a cardiac, skeletal, or smooth muscle cell.

In some embodiments, the muscle bundle (a) comprises about 1 to 1000, 1000 to 10,000, 1 to 20,000, or at least about 1000, 5000, or 10,000 muscle cells; (b) is about 0.5, 1, 2, 3, 4, 5, 2 to 3 or 0.05-5 mm long; and/or (c) comprises a cardiac, skeletal, and/or smooth muscle cell.

In some embodiments, the axon extends from the first culture compartment through the buffer compartment to the second culture compartment and forms a three-dimensional neuromuscular junction with the muscle cells.

In some embodiments, the device comprises one or more neuronal inlet injection ports for seeding the first culture compartment with neuronal cells.

In some embodiments, the device comprises one or more muscle inlet injection ports for seeding the second culture compartment with muscle cells.

In some embodiments, the device comprises a plurality of coculture chambers.

In some embodiments, the plurality of coculture chambers comprises about 5, 6, 7, 8, 9, 10, 15, 20, 25 or more coculture chambers.

In some embodiments, each coculture chamber comprises a neuronal inlet injection port for seeding the first culture compartment with neuronal cells, and the distance between each neuronal inlet injection port is the distance between the pipettes of a multichannel pipettor.

In some embodiments, each coculture chamber comprises a muscle inlet injection port for seeding the second culture compartment with muscle cells, and the distance between each muscle inlet injection port is the distance between the pipettes of a multichannel pipettor.

In some embodiments, the device comprises a first medium reservoir adjacent the first culture compartment; and a second medium reservoir adjacent the second culture compartment, the first and second medium reservoirs enabling generation of gradients of growth factors.

In some embodiments, the first culture compartment, the second culture compartment, and/or the buffer compartment comprises a hydrogel.

In some embodiments, the hydrogel comprises an alginate or a derivative thereof, gelatin, collagen, agarose, a natural or synthetic polysaccharide, polylactic acid, polyglycolic acid, poly(lysine), a polyanhydride; a poly(lactide-co-glycolide) (PLGA) polymer, a polyamino acid, a poly(alkylene oxide), a poly(ethylene oxide), a poly(allylamine)(PAM), a poly(acrylate), a polyester, polyhydroxybutyrate and poly-epsilon-caprolactone, a polyphosphazine, a poly(vinyl alcohol), a modified styrene polymer, poly(4-aminomethylstyrene), a pluronic polyol, a polyoxamer, a poly(uronic acid), a poly(vinylpyrrolidone), and/or a copolymer comprising one or more of an alginate or a derivative thereof, gelatin, collagen, agarose, a natural or synthetic polysaccharide, polylactic acid, polyglycolic acid, poly(lysine), a polyanhydride; a poly(lactide-co-glycolide) (PLGA) polymer, a polyamino acid, a poly(alkylene oxide), a poly(ethylene oxide), a poly(allylamine)(PAM), a poly(acrylate), a polyester, polyhydroxybutyrate and poly-epsilon-caprolactone, a polyphosphazine, a poly(vinyl alcohol), a modified styrene polymer, poly(4-aminomethylstyrene), a pluronic polyol, a polyoxamer, a poly(uronic acid), and a poly(vinylpyrrolidone).

In some embodiments, the hydrogel is crosslinked.

In some embodiments, the hydrogel has been crosslinked or may be crosslinked by temperature-induced crosslinking, photocrosslinking, or enzymatic crosslinking.

In some embodiments, the muscle bundle is attached to each of the one or more compliant pillars.

In some embodiments, a portion of the muscle bundle is wrapped around each of the one or more compliant pillars.

In some embodiments, the device comprises about 1, 2, 3, 4, 5, 6, 7, 8, 9, or 10 compliant pillars.

Aspects of the present subject matter provide method of using a microfluidic device, the method comprising: seeding the second culture compartment with muscle cells to enable growth of the muscle bundle, the muscle bundle wrapping around the compliant pillars; and seeding the first culture compartment with neuronal cells to enable growth of the axon to extend from the first culture compartment through the buffer compartment to the second culture compartment and form a neuromuscular junction with the muscle bundle.

In some embodiments, the method comprises stimulating the neuronal cells; and measuring deflection of the compliant pillars that result from contraction of the muscle bundle, the contraction caused by the stimulation of the neuronal cells.

In some embodiments, the muscle cells comprise myoblasts, and the myoblasts are stimulated with media comprising about 1, 1.5, 2, 2.5, 3, 3.5, 4, 4.5, or 5% horse serum to induce myoblast fusion and skeletal muscle differentiation.

Aspects of the present subject matter provide a method of assessing muscle or motor neuron function, comprising providing a microfluidic device, and stimulating the neuronal cells.

In some embodiments, the neuronal cells and/or the muscle cells comprises at least one mutation or transgene.

In some embodiments, microfluidic device further comprises a test compound.

In some embodiments, the test compound comprises a drug candidate.

In some embodiments, the test compound is an organic compound having a molecular weight less than 1000 or 2000 daltons, an RNA interference molecule, a protein, a peptide, an antibody, an antibody fragment, or an aptamer.

In some embodiments, a medium having a first concentration is added to a first medium reservoir adjacent the first culture compartment to generate a gradient medium within the coculture chamber.

In some embodiments, a second medium having a second concentration is added to a second medium reservoir adjacent the second culture compartment.

Aspects of the present invention also provide, systems, techniques and articles as described or illustrated herein.

In certain embodiments, the device comprises a system of valves. The valves may, e.g., allow for a desired coculture chamber or chamber compartment (or a plurality thereof) to be modified individually. The system of valves allows for the formation of several (for example, six, seven, eight, nine, ten, or more) mechanically decoupled individual muscle bundles. In various embodiments, the microfluidic device can include a first layer including the coculture chamber and a control layer including a valve system. In some embodiments, a microfluidic device can include a plurality of coculture chambers, a channel connecting the plurality of coculture chambers, and a valve system separating the plurality of coculture chambers. An evacuation channel can be included that, when a vacuum is applied to the evacuation channel, aspirates tissue remaining in the channel connecting the plurality of cocultures.

In some embodiments, a channel on the first layer may connect multiple coculture chambers and enable simultaneous seeding of muscle cell culture compartments. In certain embodiments, the valve system serves to selectively separate the coculture chambers. The first layer may include an evacuation channel for aspirating tissue (e.g., by applying a vacuum) remaining in the channel after seeding the muscle cell culture compartments.

In various embodiments, in order to seed a muscle cell and hydrogel mix into the muscle cell compartments of the microfluidic device in one single procedure, while allowing for mechanical isolation of each to-be-formed muscle bundle, the system of closed-at-rest valves can lift ceiling membranes above each muscle compartment wall. When a vacuum is applied to the microfluidic device, the ceiling raises above the walls, letting a liquid mix of hydrogel and muscle cells to flow along channel, filling all 6 muscle cell culture compartments at once. When vacuum is released, the ceilings come down and isolate each coculture chamber from its neighbors before the hydrogel is allowed to polymerize. The evacuation channel enables for the aspiration of the tissue remaining in any intermediate chambers in between muscle culture chambers.

In some embodiments, the second compartment includes hydrogel, and the three-dimensional neuromuscular junction forms in the hydrogel.

Cells are optionally enriched for a particular cell type, e.g., a neuronal cell or a muscle cell, or a complex of neuronal cell and a muscle cell together. In some embodiments, a cell or population of cells are purified or isolated. An isolated cell, population of cells, other entity or substance is produced, prepared, purified, and/or manufactured by intervention by a human being (the hand of man). For example, isolated cell is separated from at least about 10%, about 20%, about 30%, about 40%, about 50%, about 60%, about 70%, about 80%, about 90%, about 95%, about 96%, about 97%, about 98%, about 99% or more of the other components with which they were initially associated in a natural state (e.g., by weight, such as dry weight). In some embodiments, an isolated cell or a population of isolated cells are more than about 80%, about 85%, about 90%, about 91%, about 92%, about 93%, about 94%, about 95%, about 96%, about 97%, about 98%, about 99%, or more than about 99% pure (e.g., by weight, such as dry weight). As used herein, a substance is "pure" if it is substantially free of other components. In the case of a purified cell or population of purified cells of a particular type (e.g., phenotype or genotype), the cell or population is substantially pure of cells of another type (e.g., phenotype or genotype). A co-culture comprises at least 2 different cell types, e.g., a co-culture may comprise both a neuronal cell and a muscle cell, e.g. a neuromuscular junction formed in the hydrogel of the device described herein.

As used herein, an "isolated" or "purified" compound (such as a protein, polypeptide, polysaccharide, nucleic acid molecule, polynucleotide,), is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity may be measured by any appropriate standard method, for example, by column chromatography, thin layer chromatography, or high-performance liquid chromatography (HPLC) analysis. For example, a purified or isolated polynucleotide (ribonucleic acid (RNA) or deoxyribonucleic acid (DNA)) is free of the genes or sequences that flank it in its naturally-occurring state. In various embodiments, purified also defines a degree of sterility that is safe for administration to a human subject, e.g., lacking infectious or toxic agents.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

FIGS. 5A-G are a series of images and graphs showing that ChR integration via homologous recombination results in stable expression in ESC and ES-derived motor neurons and proper light-driven neuronal stimulation. (a) Membrane-bound expression of tdTomato-tagged Channelrhodopsin-2 is observed in transfected ES colonies. Immunostaining for Oct4 expression confirms the pluripotent nature of the transformed cells. (b) Confocal image of a ChR-HBG3-derived neurosphere on day 7 after RA and SAG treatment, showing persistent expression of ChR. (c) FACS data comparing tdTomato::ChR expression of parental (HBG3-MN) and ChR-expressing (ChR-HBG3-MN) cells dissociated from day 7 neurospheres, demonstrating robust expression and minimum silencing after reaching the motor neuron lineage. (d) A dissociated Hb9$^{GFP+}$/ChR$^{tdTom+}$ motor neuron plated on a monolayer of cortical glial feeder cells assuming proper neuronal morphology on day 3. (e) Representative trace displaying inward current upon optical stimulation (blue bar) on day 3 and day 10 on HBG3-MN and ChR$^{H134R}$-HBG3-MN. (f) Peak ($I_P$) and steady state ($I_{SS}$) inward currents on day 3, 10 and 16 in ChR-HBG3-MN (n=10). Error bars: STD. (g) Representative current-clamp recordings upon prolonged 1-sec optical stimulation displaying action potential (AP) elicitation on day 3, 10 and 16.

FIGS. 6A-C are series of images and graphs showing that ChR-HBG3-MN form functional neuromuscular junctions in vitro in adherent cultures. (a) A dissociated Hb9$^{GFP+}$/ChR$^{tdTom+}$ motor neuron forming initial contact with a C2C12-derived myotube after 1 day of coculture. (b) Muscle contraction observed upon optical stimulation (blue bar) of the ChR-HBG3-MN. The contractions were inhibited after incubation with bungarotoxin. (c) Local optogenetic excitation of neuron-muscle coculture: i) phase contract and epifluorescence images of ChR-HBG3-MN and muscle cells. ii) Muscle twitch (red box) as light stimulation (blue bars) is applied to: full field of view (1), muscle only (2), non-innervating motor neuron cluster (3), innervating cluster (4).

FIGS. 7A-C are cartoons showing microfluidic design and assembly. (a) The microfluidic design features 3 parallel gel regions accessible by 6 gel filling ports and flanked by 2 medium channels connected to 4 medium reservoirs. A surrounding vacuum channel allows for temporary bonding. Scale bar: 2 mm. (b) The platform is comprised of a top microfluidic layer assembled on top of a polydimethylsiloxane (PDMS) membrane featuring 2 sets of 2 capped pillars (inset), itself bonded to a coverslip. (c) Schematic displaying the final coculture arrangement: embedded in a hydrogel, muscle bundles wrapped around and exerted force to the pillars are innervated by neurospheres located in the opposite gel chamber separated by a 1-mm gel region.

Figure 1A:
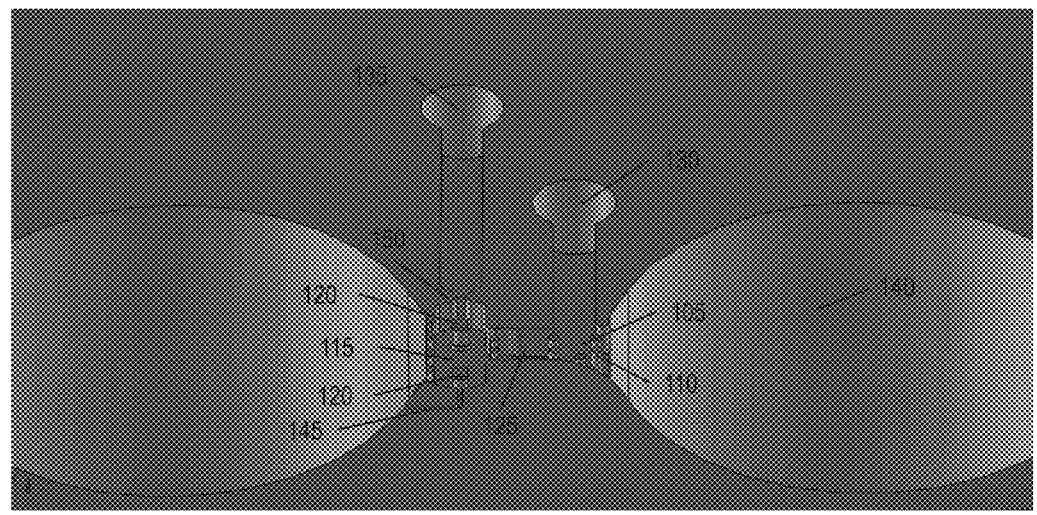
FIG. 1A is a bottom perspective view of a three-dimensional compartmentalized coculture chamber for coculture of muscle cells and neuronal cells for innervating a muscle bundle with an axon.

Embryonic stem cells are suspended in differentiation medium at $2 \times 10^4$ cells/ml. C2C12 myoblasts are suspended at $2 \times 10^4$ cells/ml in a mix of 2 mg/ml type I collagen and 20% Matrigel. The hydrogel is injected in the right channel.

The early embryoid bodies (EBs) are transferred into a low-adhesion dish and fresh medium is added. By day 1, the C2C12 have compacted the gel. Retinoic acid (RA) is supplemented to the motor neuron (MN) differentiation medium. The reversibly bonded top microfluidic part is removed, and the thin regions of gel are manually ablated. Medium is switched to 2% horse serum. Smoothened agonist (SAG) is added to the MN differentiation medium. Medium is replaced by fresh differentiation medium supplemented with glia-derived neurotrophic factor (GDNF) and ciliary neurotrophic factor (CNTF). Muscle strip are switched to 10% horse serum (HS).

Large reservoir devices are reassembled on top of the muscle strip and bonded by vacuum. Medium is purged by a mix of collagen and Matrigel. EBs are then individually seeded in the left most channel and positioned to face the muscle strip.

Over the course of 4 days, the motor neurites will navigate in three-dimensional in the hydrogel until they reach their muscle target. As early as 5 days of coculture, the first light induced muscle contraction could be seen and force could be measured.

FIGS. 9A-H are images and graphs showing muscle differentiation and neuromuscular tissue formation. (a) Immunostaining of the myogenic marker α-actinin (green) and DAPI (blue) demonstrating proper muscle differentiation and formation of sarcomeric striations (insert). Scale bars: 100 µm. (b) Muscle bundle with w normalized by the width a day 0, $w_0$·(c) Passive ($F_P$) and active ($F_A$) force generation over the course of 16 days. (d) Representative image of a neuron-muscle coculture in the microfluidic device on day 1 of coculture. Scale bar: 500 µm (e) Neurite extension over 4 days of coculture. Scale bar: 250 µm. (f) Left y-axis: Maximum neurite outgrowth $L_{max}$ over the first 4 days of culture compared to the average distance between neurospheres and muscle bundles (red dashed line). Right y-axis: Percentage of muscle bundles contacted by at least one neurite $\Delta_{CM}$ over the course of 4 days. (g) Confocal three-dimensional reconstruction of neurites in the bridge gel region after 1 day of coculture. Scale bar: 200 µm. All error bars: SEM.

FIGS. 10A-E are images, graphs, and kymographs showing activation of NMJs within the microfluidic device. (a) Application of glutamate to the medium results in a delayed stimulation of the muscle, leading to the initiation of muscle twitching with force F (left y-axis) at an increasing frequency ($f_T$) (right y-axis) as glutamate diffuses within the neurospheres. (b) Force (F) generated by the muscle bundle upon illumination of the ChR2$^{H134R}$-HBG3-MN neurospheres on day 15. Application of BTX inhibited the contractions. (c) Colocalization of incoming motor axons and clusters of AChR indicative of the presence of NMJ. (d) Kymographs of the pillar displacement on day 16 for 3 stimulation light intensities ($I_L$). (e) Muscle twitching frequencies ($f_T$) as a function of light intensity ($I_L$).

FIGS. 11A-D are cartoons, Southern blots, and graphs showing DNA construct design, integration validation and pluripotency characterization. (a) Design of the DNA construct. (b) Schematic illustrating the southern blot strategies. (c) Southern blots. (d) Gene expression assay for 5 pluripotency markers.

FIGS. 12A-F are graphs showing electrophysiological characterization of the ChR-HBG3-MN. (a) Membrane capacitance ($C_m$), membrane resistance ($R_m$) and membrane potential ($V_m$) in motor neurons were not altered by the presence of ChR. (b) Peak ($I_P$) and steady state ($I_{SS}$) inward current as a function of light intensity ($I_L$) for blue and green illumination. (c) Representative action potential elicitation over 20 pulses of light of width 10 ms at frequencies ($f_S$) ranging from 5 to 40 Hz, at days 3, 10 and 16. (d) Number of action potentials elicited over 20 pulses of light of increasing frequency. (e) Representative action potential elicitation over 5 pulses of light of width ($\delta_P$) ranging from 0.5 to 10 ms, at days 3, 10 and 16. (f) Number of action potentials elicited over 20 pulses of light of increasing width ($\delta_P$). All errors bars: STD.

FIGS. 13A-B are graphs showing optogenetic activation of NMJs in adherent cocultures. Examples of an optogenetic neuronal stimulation of a muscle cell before and after BTX treatment. The presence of a spontaneous twitch indicate that the myofiber was still contractile after BTX application and that the absence of contraction upon illumination is only due to NMJ inhibition.

FIG. 14A-C are a cartoon and images showing modes of tissue ablation. (a) Schematic depicting the 2P ablation set-up. (b) Thin muscle/hydrogel tissue being dissected by 2P ablation. (c) Comparison of tissue resorption following ablation by 2-photon stimulation or manual dissection.

FIGS. 15A-D are a cartoon, images, and a graph showing photosensitization of the C2C12 myoblasts. (a) ChR2$^{H134R}$ plasmid design for C2C12 viral infection. (b) Comparison of cell morphology and ChR::tdTomato expression between parental C2C12 and ChR2$^{H134R}$-C2C12. (c) Contraction pattern upon light stimulation of muscle bundles derived from ChR2$^{H134R}$-C2C12.

FIGS. 16A-C are cartoons and graphs showing the influence of the hydrogel on the force measured by the pillar. (a) Schematic modeling the potential mechanical contributions of a gel surrounding a contractile muscle bundle. (b) Time course of the force (F) generated by the muscle strip upon excitation and measured by the pillar deflection. (c) Comparison of the steady state and peak forces along with the initial force rate (R) before and after the surrounding medium was replaced by the matrix. Error bars: STD.

FIGS. 17A-B are images and a graph showing motor neurite outgrowth in the microfluidic device: (a) Epifluorescence images of neurites extending into the extracellular matrix. (b) Time course of the maximum neurite outgrowth ($L_{max}$) toward and away from the muscle bundle over the first 3 days of coculture.

FIGS. 18A-B: Opposite gradients as a mean to provide cell specific media. (a) Schematic illustrating the formation of opposite concentration gradient by supplying each channel with a different medium, a neuron-specific medium A, and a myogenic medium B. (b) Fluorescent dextran characterization of the formation of opposite gradients. The white dashed lines materialize the position of the neuro-

DETAILED DESCRIPTION

The present disclosure provides novel devices and methods for the three dimensional coculture of muscle and neuronal cells. Microfluidic devices that enable the coculture of neurospheres and muscle bundles are described. The devices may be used to promote the formation of neuromuscular junctions (NMJs) in a microenvironment that mimics that of an in vivo counterpart. Additionally, the devices allow for the visualization and study of axon formation and NMJ function, as well as (i) the precise positioning of the motor neuron containing neurospheres with respect to a muscle bundle; and (ii) compartmentalization, which provides the ability to visualize axon outgrowth and supply, as well as the stimulation of each tissue type (e.g. muscle and neuronal) selectively.

Motor units are the fundamental element responsible for muscle movement. They are formed by lower motor neurons and their muscle targets, synapsed via NMJ. The loss of NMJs in neurodegenerative disorders (such as amyotrophic lateral sclerosis (ALS) or spinal muscle atrophy (SMA)) or as a result of traumatic injuries affects millions of lives each year. Developing in vitro assays that closely recapitulate the physiology of neuromuscular tissues is crucial to understand the formation and maturation of NMJs, as well as help unravel the mechanisms leading to their degeneration and repair.

Motor units, consisting of lower motor neurons (MN) and the muscle fibers they innervate via NMJs, are the fundamental elements responsible for producing virtually all motor functions, from locomotion to respiration or speech. Their failure is associated with highly incapacitating or lethal genetic disorders such as ALS (amyotrophic lateral sclerosis), SMA (spinal muscular atrophy) or DMD (Duchenne muscular dystrophy) (J. Olesen, a Gustaysson, M. Svensson, H.-U. Wittchen, B. Jonsson, Eur. J. Neurol. 2012, 19, 155), or can be caused by traumatic injuries. Serving as a model for synaptic function, motor units have been the object of prior pioneering work that led to identification of the existence of neurotransmitters and their quantal release (H. H. Dale, W. Feldberg, M. Vogt, J. Physiol. 1936, 86, 353; P. Fatt, B. Katz, J. Physiol. 1952, 117, 109). In vertebrates, NMJ function involves numerous specialized cell types, from astrocytes secreting supporting factors to Schwann cells providing electrical and chemical isolation (J. R. Sanes, J. W. Lichtman, Annu. Rev. Neurosci. 1999, 22, 389; E. M. Ullian, B. T. Harris, A. Wu, J. R. Chan, B. a Barres, Mol. Cell. Neurosci. 2004, 25, 241).

Commonly used primitive animal models like aplysia, *C. elegans* or *Drosophila* larva, provide important but limited insight into the physiology of vertebrate and mammalian NMJs due to fundamental differences, such as the absence, in these models, of synapse elimination and remodeling, the presence of glutamatergic motor neurons or inhibitory NMJs and the absence of myelin sheath (H. Keshishian, K. Broadie, a Chiba, M. Bate, Annu. Rev. Neurosci. 1996, 19, 545; E. M. Jorgensen, M. L. Nonet, Dev. Biol. 1995, 6, 207; J. L. Cohen, K. R. Weiss, I. Kupfermann, J. Neurophysiol. 1978, 41, 157). On the other hand, mammalian in vivo models are complex and not amenable to systematic parameter tuning. Development of in vitro systems that mimic their in vivo counterparts and allow for de novo NMJ formation therefore remain a high priority. Traditional 2D culture platforms, advantageous for their simplicity, typically consist of a layer of myotubes differentiated from myoblasts onto which motor neurons are uniformly plated. These 2D mixed culture systems using various combinations of human, rodent or chick cells have been utilized for decades and have contributed greatly to our understanding of the fundamental physiology of neuromuscular junctions; examples include acetylcholine receptor clustering (E. Frank, G. D. Fischbach, Early events in neuromuscular junction formation in vitro. Induction of acetylcholine receptor clusters in the postsynaptic membrane and morphology of newly formed synapses. J. Cell Biol. 83, 143-158 (1979)), the role of Schwann cells on NMJ formation (E. M. Ullian, B. T. Harris, A. Wu, J. R. Chan, B. a Barres, Schwann cells and astrocytes induce synapse formation by spinal motor neurons in culture. Mol. Cell. Neurosci. 25, 241-51 (2004)) or the regulation of acetylcholinesterase activity (L. L. Rubin, S. M. Schuetze, C. L. Weill, G. D. Fischbach, Regulation of acetylcholineesterase appearance at neuromuscular junctions in vitro. Nature. 283, 264-267 (1980)). They have also proven to be efficient tools to investigate the functionality of healthy (X.-J. Li et al., Specification of motoneurons from human embryonic stem cells. *Nat. Biotechnol.* 23, 215-21 (2005), G. B. Miles et al., Functional Properties of Motoneurons Derived from Mouse Embryonic Stem Cells. J. Neurosci. 24, 7848-7858 (2004)) and dysfunctional (P. H. Chipman, Y. Zhang, V. F. Rafuse, A stem-cell based bioassay to critically assess the pathology of dysfunctional neuromuscular junctions. PLoS One. 9, e91643 (2014)) stem cell-derived motor neurons, and have served to optimize in vitro neuron/muscle culture conditions (M. Das et al., Embryonic motoneuron-skeletal muscle co-culture in a defined system. Neuroscience. 146, 481-8 (2007), X. Guo et al., Neuromuscular Junction Formation Between Human Stem-Cell-Derived Motoneurons and Rat Skeletal Muscle in a Defined System. Tissue Eng. 16 (2010), doi:10.1089/ten.tec.2010.0040, J. A. Umbach, K. L. Adams, C. B. Gundersen, B. G. Novitch, Functional neuromuscular junctions formed by embryonic stem cell-derived motor neurons. PLoS One. 7, e36049 (2012)).

However, their simplicity can at times be outweighed by their limitations. The 2D nature of the system leads to a mismatch between the mechanical properties of the cells and the substrate, that can impede muscle differentiation (A. J. Engler et al., Myotubes differentiate optimally on substrates with tissue-like stiffness: pathological implications for soft or stiff microenvironments. J. Cell Biol. 166, 877-87 (2004)) or affect neurite outgrowth (R. K. Willits, S. L. Skornia, Effect of collagen gel stiffness on neurite extension. J. Biomater. Sci. Polym. Ed. 15, 1521-31 (2004), H. G. Sundararaghavan, G. a Monteiro, B. L. Firestein, D. I. Shreiber, Neurite growth in three-dimensional collagen gels with gradients of mechanical properties. Biotechnol. Bioeng. 102, 632-43 (2009)), and preclude direct interaction between the ECM and the resident neurons and muscle cells (J. R. Sanes, Roles of extracellular matrix in neural development. Annu. Rev. Physiol. 45, 581-600 (1983), D. a Tonge et al., Effects of extracellular matrix components on axonal outgrowth from peripheral nerves of adult animals in vitro. Exp. Neurol. 146, 81-90 (1997)). The mixed nature of the cultures make it difficult to monitor individual cell types or axonal outgrowth and hinder the proper supply of tissue-specific factors or drugs. Moreover, the contraction generated by the muscle tissue can only be qualitatively assessed. Finally these traditional platforms do not favor high throughput and limit the ability to automate cell handling and data acquisition.

Over the years, progress has been made towards addressing some of these limitations associated with the traditional assays. Campenot chambers (R. B. Campenot, K. Lund, S.-A. Mok, Production of compartmented cultures of rat sympathetic neurons. Nat. Protoc. 4, 1869-87 (2009)) have been used for compartmentalized 2D co-cultures to study synapse elimination (P. G. Nelson, R. D. Fields, C. Yu, Y. Liu, Synapse elimination from the mouse neuromuscular junction in vitro: a non-Hebbian activity-dependent process. J. Neurobiol. 24, 1517-30 (1993)) or allow for enhanced visualization of axonal outgrowth (J. M. Harper et al., Axonal growth of embryonic stem cell-derived motoneurons in vitro and in motoneuron-injured adult rats. Proc. Natl. Acad. Sci. 101 (2004)). Microfluidic devices confer a higher throughput while increasing manipulability and control over culture conditions, and have been proposed and applied to remotely innervate cardiac cells with autonomic neurons (A. Takeuchi et al., Device for co-culture of sympathetic neurons and cardiomyocytes using microfabrication. Lab Chip. 11, 2268-75 (2011), A. Takeuchi et al., Sympathetic neurons modulate the beat rate of pluripotent cell-derived cardiomyocytes in vitro. Integr. Biol. 4, 1532-1539 (2012)) or skeletal muscle cells with motor neurons (Z. Tong et al., Engineering a functional neuro-muscular junction model in a chip. RSC Adv. 4, 54788-54797 (2014), K. A. Southam, A. E. King, C. A. Blizzard, G. H. McCormack, T. C. Dickson, Microfluidic primary culture model of the lower motor neuron-neuromuscular junction circuit. J. Neurosci. Methods. 218, 164-169 (2013), E. E. Zahavi et al., A compartmentalized microfluidic neuromuscular co-culture system reveals spatial aspects of GDNF functions. J. Cell Sci. 128, 1241-1252 (2015), A. Ionescu, E. E. Zahavi, T. Gradus, K. Ben-Yaakov, E. Perlson, Compartmental microfluidic system for studying muscle-neuron communication and neuromuscular junction maintenance. Eur. J. Cell Biol. 95, 69-88 (2015)). Other systems enable culture in a three-dimensional configuration, in an attempt to increase the physiological relevance. They take the form of organotypic spinal cord slices in contact with myoblast-laden fibrin gels (a D. Bach, J. P. Beier, G. B. Stark, Expression of Trisk 51, agrin and nicotinic-acetycholine receptor epsilon-subunit during muscle development in a novel three-dimensional muscle-neuronal co-culture system. Cell Tissue Res. 314, 263-74 (2003)) or microdevices, inspired by three-dimensional muscle culture systems (S. Hinds, W. Bian, R. G. Dennis, N. Bursac, The role of extracellular matrix composition in structure and function of bioengineered skeletal muscle. Biomaterials. 32, 3575-83 (2011), H. H. Vandenburgh et al., Tissue-Engineered Skeletal Muscle Organoids for Reversible Gene Therapy. Hum. Gene Ther. 7, 2195-2200 (1996)), allowing the formation of three-dimensional muscle bundles onto which motor neuron-containing neurospheres were seeded (Y. Morimoto, M. Kato-Negishi, H. Onoe, S. Takeuchi, Three-dimensional neuron-muscle constructs with neuromuscular junctions. Biomaterials. 34, 9413-9 (2013)). These configurations however lacked clear physical separation between cell types. Finally, some platforms have used compliant substrates to quantitatively infer muscle contraction, whether by plating the cells on arrays of microneedles (K. R. Tan et al., Neural bases for addictive properties of benzodiazepines. Nature. 463, 769-74 (2010)) or flexible membranes (A. W. Feinberg et al., Muscular thin films for building actuators and powering devices. Science. 317, 1366-70 (2007), K. Wilson, M. Das, K. J. Wahl, R. J. Colton, J. Hickman, Measurement of contractile stress generated by cultured rat muscle on silicon cantilevers for toxin detection and muscle performance enhancement. PLoS One. 5 (2010), doi:10.1371/journal.pone.0011042). This latter concept was the basis for a study that reported the formation of functional NMJ between motor neurons and muscle cells plated in 2D on cantilevers and the quantification of muscle contraction upon cantilever deflection.

However, despite years of efforts, there has remained a long-felt need for devices (such as those disclosed herein) that enable the precise positioning of motor neuron containing neurospheres with respect to muscle bundles, as well as the compartmentalization of different cell types.

The present disclosure provides an informative in vitro NMJ system that: (1) allows for a reductionist and modular yet physiologically relevant culture (presence of extra cellular matrix (ECM), three-dimensional (3D) culture, compartmentalized and functional tissues), (2) provides user defined and spatiotemporally resolved neuronal stimulation, and (3) allows for non-invasive and live output measurement relevant to tissue function (e.g. muscle force generation).

Aspects of the current subject matter relate to a microfluidic device enabling precise and repeatable three-dimensional compartmentalized coculture of muscle cells and neuronal cells for innervating muscle bundles with axons. In various embodiments, the microfluidic device includes a series of coculture chambers, each having a neuronal culture compartment including one or more retaining features such as a pillar cup. The coculture chamber includes a muscle cell culture compartment including one or more compliant pillars and a buffer compartment separating the neuronal cell compartment and the muscle cell compartment.

The compliant pillars are deflectable and when wrapped by a muscle bundle will deflect when the muscle bundle contracts. Deflection by the compliant pillars allows for measurement of the force generated by the muscle bundle when the muscle bundle contracts. These integrated compliant pillars are a means to non-invasively and passively measure the force generated by the muscle bundle.

Figure 1B:
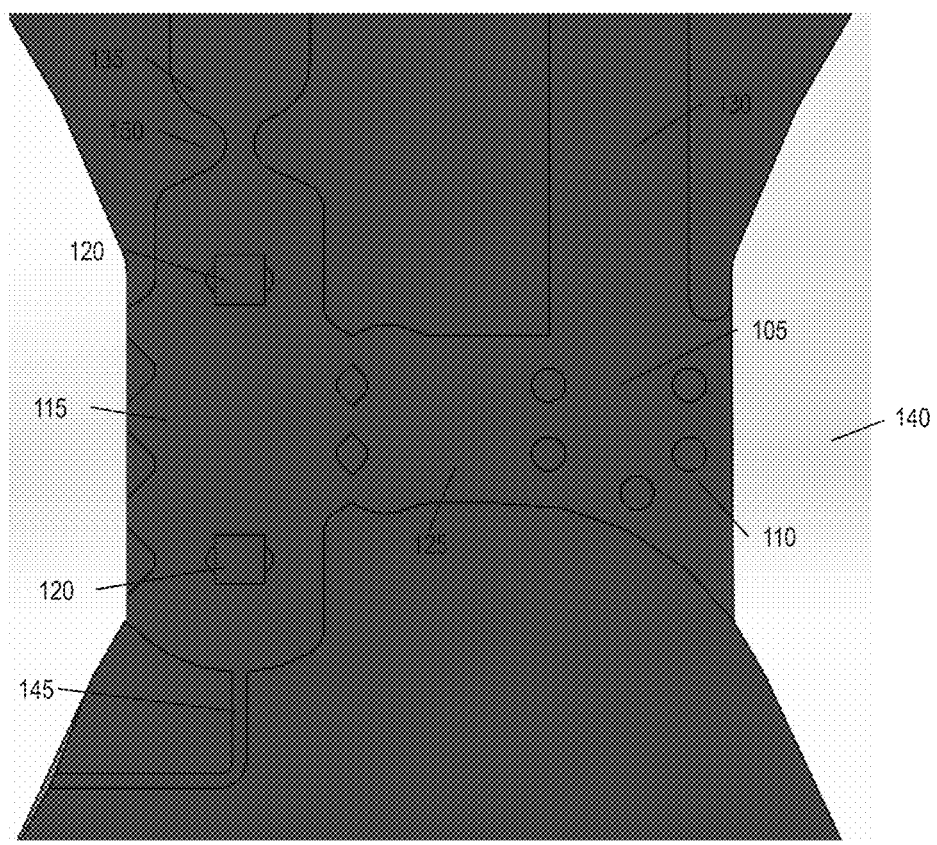
FIGS. 1B and 1C illustrate bottom and side perspective views, respectively, of the coculture chamber.
Figure 1C:
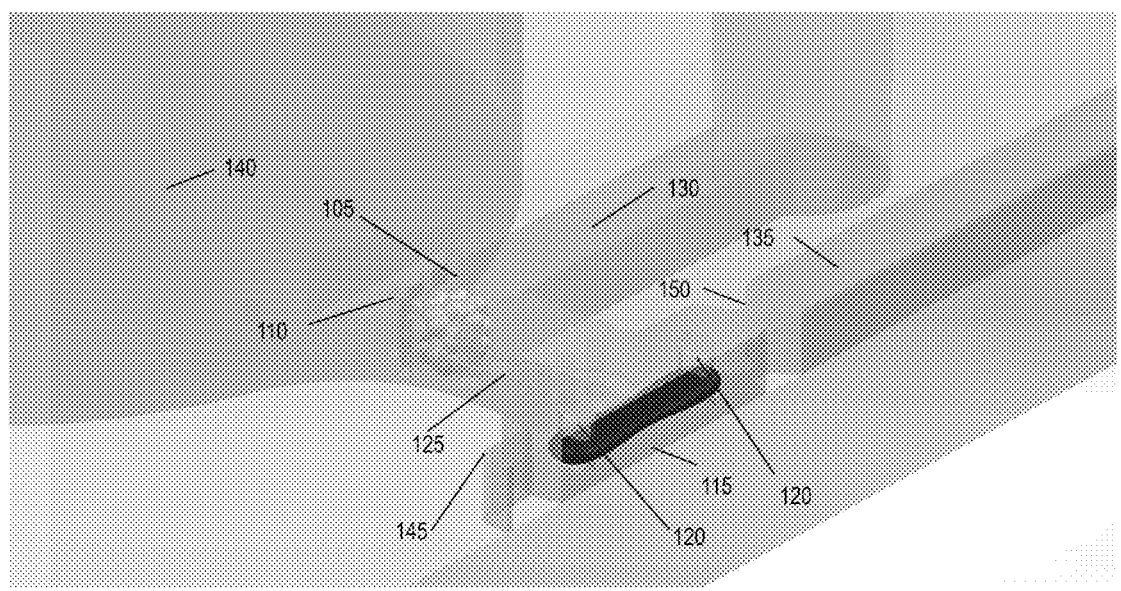
Figure 1D:
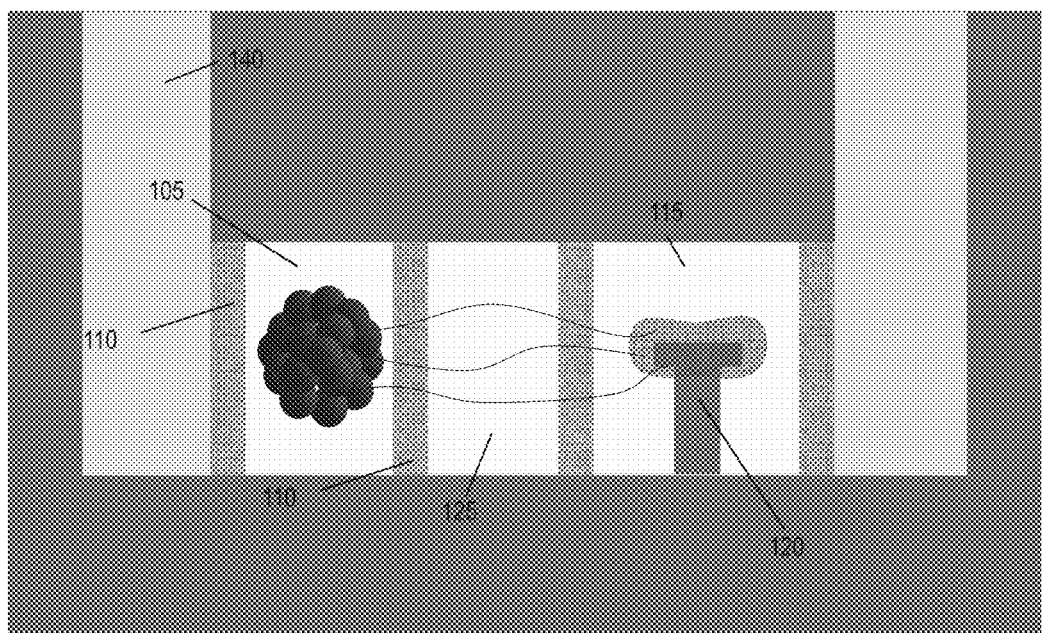
FIG. 1D illustrates a cross sectional view of the coculture chamber in which a neuronal cell, axons, and muscle bundle is shown.

FIG. 1A is a bottom perspective view of an example coculture chamber 100 for coculture of muscle cells and neuronal cells. FIGS. 1B and 1C illustrate bottom and side perspective views, respectively, of the coculture chamber 100. FIG. 1D illustrates a cross sectional view of the coculture chamber 100 in which a neuronal cell, axons, and muscle bundle is shown. The coculture chamber 100 allows for innervating a muscle bundle with one or more axons and for measurement of force exerted by the muscle bundle when the muscle bundle contracts. The coculture chamber 100 includes a neuronal culture compartment 105 having one or more retaining features 110 for retaining neurospheres within the neuronal culture compartment 105. In the illustrated implementation, the retaining features 110 are rigid pillars positioned in a cup formation (e.g., a concave formation).

The coculture chamber 100 includes a muscle cell culture compartment 115 having one or more compliant pillars 120. A buffer compartment 125 separates the neuronal cell compartment 105 and the muscle cell compartment 115. The muscle chamber is separated from its neighboring regions by a permeable barrier that allows fluid and cell media materials to pass through but constrains movement of a hydrogel. In some embodiments, the permeable barrier comprises a series of several vertical pillars which constrain the muscle cell-laden hydrogel to its chamber by surface tension. Other means (e.g., mesh, plates, and walls with openings) are disclosed herein and may be used to constrain the hydrogel.

In various embodiments, the space within the device into which a hydrogel (e.g., a muscle cell-laden hydrogel) will form may contain or be separated from neighboring regions/ chambers with a permeable barrier, e.g., one or more pillars. Pillars may be formed, e.g., with a lithography process. In some embodiments, the pillars improve the mechanical stability of a hydrogel. For example, the pillars may increase surface tension of the material used to form the hydrogel; thus, flow of the hydrogel material into other regions/chambers of the microfluidic device is reduced. The shape of the pillars may be modified. For example, the pillars may have a hexagonal, circular (e.g., the pillar is in the shape of a cylinder or cone), square, rectangular, or irregular shape. Pillar size may range (e.g., height or diameter), e.g., from a µm or less to several mm or greater (such as less than about 100 µm, or about 100 µm, 150 µm, 250 µm, 500 µm, 1 mm, 1.5 mm or more. In various embodiments, the diameter of a pillar varies along its height. In some embodiments, the pillars have a conical shape. In certain embodiments, the pillars comprise a diameter of about 50 to 125 or 75 to 100 µm or more. In various embodiments, the pillars comprise a height of about 250, 260, 270, 280, 290, 300, 310, 320, 330, 340, 350 or 250-350 µm or more. Non-limiting examples of pillars are described in U.S. Pat. No. 9,121,847, issued Sep. 1, 2015, the entire content of which is incorporated herein by reference.

In an implementation, the coculture chamber 100 has a cell culture region. In various embodiments, the cell culture region is about 0.5, 1.25, 1.5, 1.75, 2, 2.5, 3, 4, 5-wide or more.

In certain embodiments, the buffer compartment 125 can be filled with hydrogel. In some implementations, the buffer compartment 125 is plain hydrogel, i.e. a hydrogel containing no cells. In other implementations, the hydrogel can contain one or more cells. The neuronal cell culture compartment 105 and the neuronal cell culture compartment 115 can also be filled with hydrogel providing a three-dimensional, compliant, and extracellular matrix (ECM) rich microenvironment for the cultures.

The coculture chamber 100 may include a neuronal inlet injection port 130 and a muscle inlet injection port 135. The neuronal inlet injection port 130 allows for seeding the neuronal culture compartment 105 with neuronal cells, e.g., in the form of neuroshperes. The muscle inlet injection port 135 allows for seeding the muscle cell culture compartment 115 with muscle cells.

Medium reservoirs 140 may be adjacent the neuronal culture compartment 105 and the muscle cell culture compartment 115 allowing for application of medium to the respective compartments. Media contained in both reservoirs 140 provides nutrients and factors of interest while allowing for waste removal via a diffusive process. In the case where one of the reservoirs contains a medium whose formulation differs from that of the opposite reservoir, chemical gradients will occur by diffusion through the hydrogel contained in the culture chambers.

In some embodiments, a small channel 145 (e.g., an air escape channel) connects the end of the muscle chamber to an adjacent reservoir. This channel prevents the formation of a bubble during the seeding of the muscle cell-laden hydrogel by allowing air to escape to the side channel. The channel may be, e.g., less than 10, 5, or 1 microns in diameter. Hydrogel, when injected in its liquid state, can only be pushed to the limit of the muscle chamber, and not further, without applying substantial pressure to the hydrogel. The small channel 145 can be L-shaped and serves as an escape channel to evacuate any air bubble(s) that might form during the injection process.

In certain embodiments, a constriction feature 150 or necking in the muscle chamber injection channel serves to generate a constriction in the muscle tissue, acting as a weakening mechanism. The constriction feature 150 at the entrance weakens the muscle tissue so that when the muscle tissue becomes contractile, the tissue ruptures at the constriction feature 150 point because the tissue is thin at the constriction feature 150, which in turns results in an isolated muscle bundle. The constriction feature 150 enables formation of an individual, freely contractile muscle bundle. Further, the constriction feature 150 removes the necessity for manual ablation of the muscle bundle.

When the muscle cell culture compartment 115 is seeded with muscle progenitor cells or myoblasts under appropriate conditions, the myoblasts differentiate into myofibers and form muscle bundles that wrap around compliant pillars 120. When the neuronal cell culture compartment 105 is seeded with neuronal cells and under appropriate conditions, axons can grow and navigate (e.g., extend) from the neuronal cell culture compartment 105 through the buffer compartment 125 to the muscle cell culture component 115 and, upon contacting the muscle bundles, can form neuromuscular junctions with the myofibers.

Figure 2:
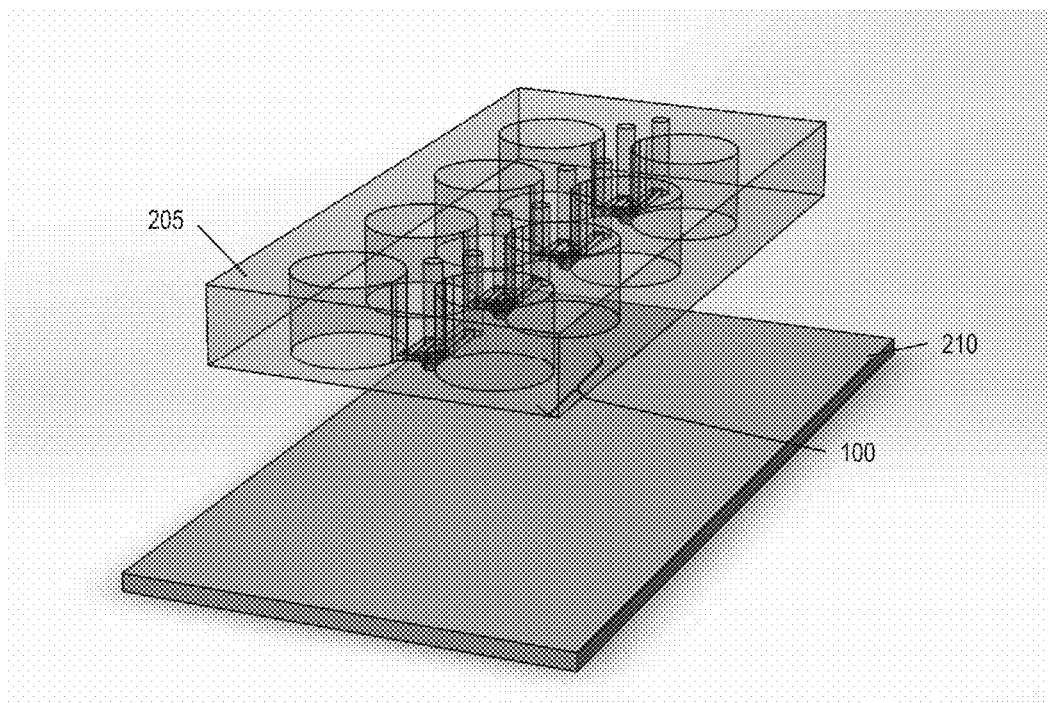
FIG. 2 is an exploded view of a microfluidic device including multiple coculture chambers.
Figure 3A:
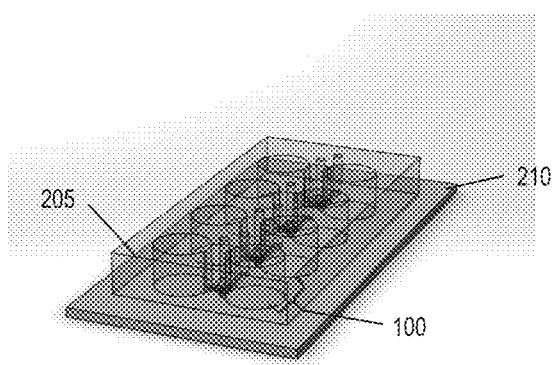
FIG. 3A-C illustrate several fully assembled views of the microfluidic device illustrated in FIG. 2.
Figure 3B:
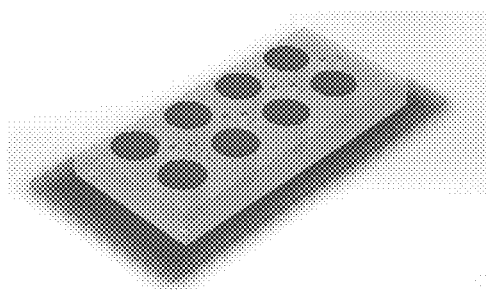
Figure 3C:
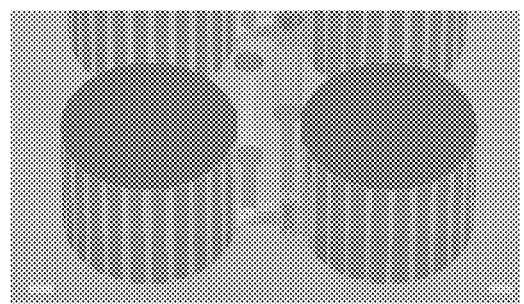

In some implementations, multiple coculture chambers 100 may be included in a microfluidic device 200. FIG. 2 is an exploded view of the microfluidic device 200 and FIG. 3A-C illustrate several fully assembled views of the microfluidic device illustrated in FIG. 2. The illustrated example microfluidic device 200 includes an elastomerlayer 205 with six independent cell culture chambers 100.

In an exemplary implementation, layer 205 is made with polydimethylsiloxane (PDMS) and casted from a negative mold, fabricated via photolithography using SU8 photoresist. The first layer 205 rests upon a substrate 210. In an implementation, the substrate is a microscopy glass slide. In some embodiments, the substrate comprises a glass coverslip or a slab of PDMS. PDMS is a ubiquitous polymer used in microfluidics and fast prototyping. It is biocompatible, transparent, gas permeable and can be flexible.

Figure 4:
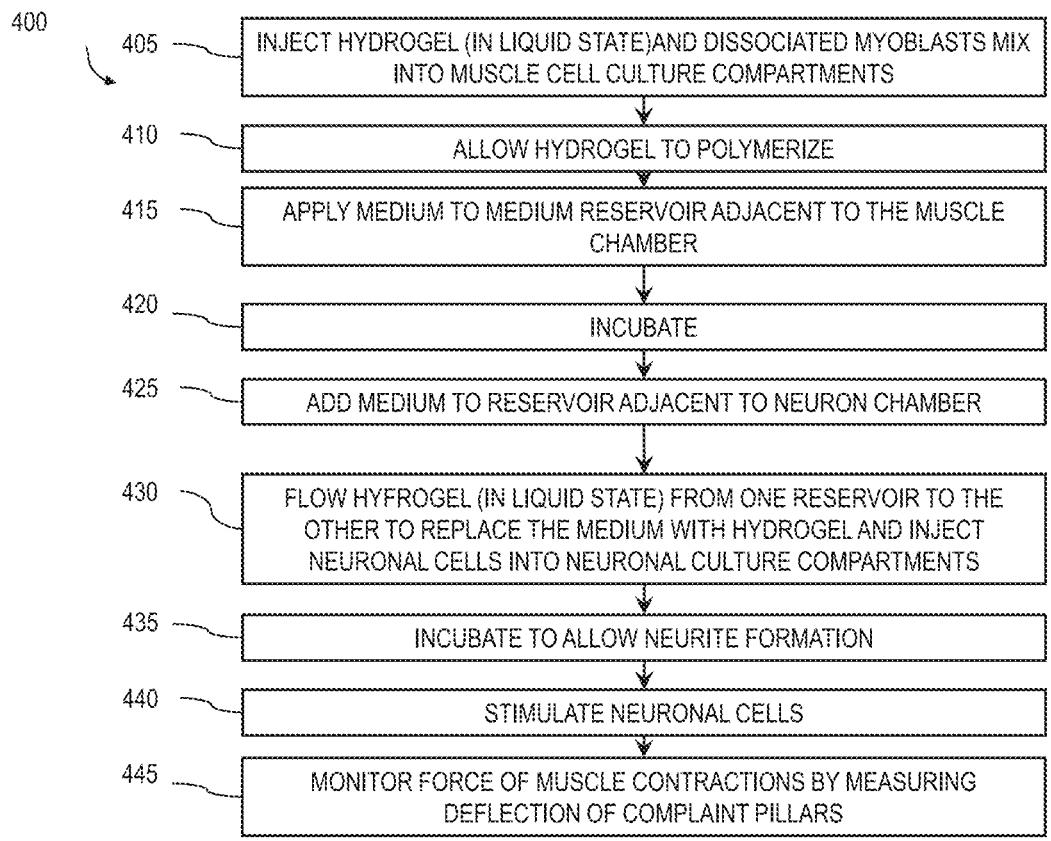
FIG. 4 is a process flow diagram illustrating an example method of using the microfluidic device for coculture of neuronal and muscle cells, as well as for measuring force exerted by muscle bundles when the muscle bundles contract.

FIG. 4 is a process flow diagram illustrating an example method 400 of using the example microfluidic device 200 for coculture of neuronal and muscle cells, as well as for measuring force exerted by muscle bundles when the muscle bundles contract.

In some embodiments, at 405, a mix of hydrogel (in liquid state) and dissociated myoblasts is injected into the muscle cell culture compartments 115. The gel remains in the muscle cell culture compartments due to surface tension and the presence of pillars extending throughout the thickness of the device and lining each muscle cell culture compartment 115. At 410, the hydrogel is then allowed to polymerize via temperature-induced crosslinking of collagen. Then, at 415, a medium is supplied to the medium reservoir 140 to the right of the muscle culture compartment 115.

Various time points and growth conditions may be used. In a non-limiting example, at 420, during the following 1, 2, 3, 4, 5, 6, 7, 8, 9, 10 or more days of incubation, myoblasts compact the gel and form muscle bundles, which wrap around the sets of, e.g., 1, 2, 3, 4, 5, 6, 7, 8, 9, 10 or more compliant pillars 120 (two are shown) located in each muscle cell culture compartments 115. On, e.g., day 1, 2, 3, 4, 5, 6, 7, 8, 9, or 10, medium is switched to a myogenic medium consisting of, e.g., about 1, 1.5, 2, 2.5, 3, 4, or 5% Horse serum, which triggers myoblast fusion and skeletal muscle differentiation. In the meantime, in some embodiments, embryonic stem cells are differentiated into motor neurons, using well-established protocol. In certain embodiments, motor neurons are derived from embryonic stem cells in the form of neurospheres before being seeded into a device. In certain embodiments, cells are suspended in differentiation medium, resulting, after, e.g., about 1, 1.5, 2, 2.5, 3, 4 or 5 days, in the formation of embryoid bodies. In some embodiments, the medium is supplemented with retinoic acid on about day 1, 2, 3, 4, 5, 6, 7, 8, 9, or 10 and then sonic hedgehog (or smoothened agonist) on, e.g., day 2, 3, 4, 5, 6, 7, 8, 9, or 10 (two morphogens that are responsible for the differentiation into motor neurons). In various embodiments, medium is replaced on about day 1, 2, 3, 4, 5, 6, or 7 and the differentiated neurospheres are ready to be used on, e.g., about day 2, 3, 4, 5, 6, 7, 8, 9, or 10. In certain embodiments, at 425, within about 3 or 4 days of incubation, the medium should have seeped through the buffer compartment and the neuronal compartment. At that moment or subsequently, medium can be supplied to the reservoir adjacent to the neuronal chamber.

In some embodiments, at 430, on about day 5, 6, 7, 8, 9, or 10 (or later), hydrogel (in liquid state) flows from one reservoir to the other such that the medium surrounding the muscle bundles is replaced by plain hydrogel (in liquid state), and individual neurospheres, suspended in the same hydrogel, are injected into the neurosphere seeding port 130. Replacement of the medium by liquid hydrogel is possible because the gel that has previously polymerized with the myoblast will have compacted into a muscle bundle. That bundle is, at this point, surrounded by culture medium. When the neurospheres are injected within a plain hydrogel and the culture medium is replaced by hydrogel, everything can be done at low temperatures (e.g., on ice) to prevent immediate polymerization. Once the liquid hydrogel has chased all the culture medium within the microfluidic chambers, the gel is allowed to polymerize. The presence of the retaining features 130 (e.g., the pillars) retains the neurosphere(s) in an ideal position with respect with the muscle bundles. Once the gel has polymerized, the culture is supplied with culture medium via the adjacent medium reservoir 140.

In various embodiments, at 435, over the course of the following days, neurites grow out of the neurospheres and eventually reach the muscle bundles, where the neurites initiate contact with the myofibers and potentially form neuromuscular junctions. At 440, the neuronal cells can be stimulated causing muscle contractions if functional neuromuscular junctions are present. At 445, the force of the muscle contractions can be monitored by measuring the deflection of the compliant pillars 120 around which the muscle bundles are wrapped. Non-limiting examples of devices and methods for measuring the force of muscle contractions are described in U.S. Patent Application Publication No. 2014/0220555, published Aug. 7, 2014; and Vandenburgh et al., Proc. Natl. Acad. Sci. U.S.A 2009, 106, 10097, the entire contents of each of which re incorporated herein by reference.

Although a few variations have been described in detail above, other modifications or additions are possible. For example, skeletal myoblasts can be replaced by cardiomyocytes or smooth muscle cells. The hydrogel can be of diverse nature. For example, the hydrogel may comprise, e.g., an alginate or a derivative thereof, gelatin, collagen, agarose, a natural or synthetic polysaccharide, polylactic acid, polyglycolic acid, poly(lysine), a polyanhydride; a poly(lactide-co-glycolide) (PLGA) polymer, a polyamino acid, a poly(alkylene oxide), a poly(ethylene oxide), a poly(allylamine) (PAM), a poly(acrylate), a polyester, polyhydroxybutyrate and poly-epsilon-caprolactone, a polyphosphazine, a poly(vinyl alcohol), a modified styrene polymer, poly(4-aminomethylstyrene), a pluronic polyol, a polyoxamer, a poly (uronic acid), a poly(vinylpyrrolidone), and/or a copolymer comprising one or more of an alginate or a derivative thereof, gelatin, collagen, agarose, a natural or synthetic polysaccharide, polylactic acid, polyglycolic acid, poly(lysine), a polyanhydride; a poly(lactide-co-glycolide) (PLGA) polymer, a polyamino acid, a poly(alkylene oxide), a poly(ethylene oxide), a poly(allylamine)(PAM), a poly(acrylate), a polyester, polyhydroxybutyrate and poly-epsilon-caprolactone, a polyphosphazine, a poly(vinyl alcohol), a modified styrene polymer, poly(4-aminomethylstyrene), a pluronic polyol, a polyoxamer, a poly(uronic acid), and a poly(vinylpyrrolidone).

As used herein, the term "about" in the context of a numerical value or range means±10% of the numerical value or range recited or claimed, unless the context requires a more limited range.

It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to and including 5.0 mg. The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

EXAMPLE

Microfluidic Platform for the Formation of Optically Excitable, Three-dimensional, Compartmentalized Motor Units This example presents a microfluidic platform designed to coculture myoblast-derived muscle strips and motor neurons differentiated from mouse embryonic stem cells (ESC) within a three-dimensional (3D) hydrogel. The device geometry mimics the spinal cord-limb physical separation by compartmentalizing the two cell types, which also facilitates the observation of three-dimensional neurite outgrowth and remote muscle innervation. Moreover, the use of complaint pillars as anchors for the muscle strips provides a quantitative functional readout of force generation. Finally, photosensitizing the ESC provides a pool of source cells that can be differentiated into optically excitable motor neurons, allowing for spatiodynamic, versatile and non-invasive in vitro control of the motor units.

To facilitate motor neuron excitation and provide a means of rapid, spatially-resolved and non-invasive motor neuron activation, the optically excitable cation channels Channelrhodopsin-2 (ChR2) were utilized. ChR2 and other opsins of the same family have proven to be a valuable and versatile tool in neuroscience (G. Nagel, T. Szellas, W. Huhn, S. Kateriya, N. Adeishvili, P. Berthold, D. Ollig, P. Hegemann, E. Bamberg, Proc. Natl. Acad. Sci. 2003, 100, 13940; E. S. Boyden, F. Zhang, E. Bamberg, G. Nagel, K. Deisseroth, Nat. Neurosci. 2005, 8, 1263) and have been widely used in in vivo models to stimulate NMJs (S. R. Pulver, S. L. Pashkovski, N. J. Hornstein, P. A. Garrity, L. C. Griffith, J Neurophysiol 2009, 101, 3075; M. E. Llewellyn, K. R. Thompson, K. Deisseroth, S. L. Delp, Nat. Med. 2010, 16, 1161; V. Caggiano, M. Sur, E. Bizzi, PLoS One 2014, 9, 1; C. Schroll, T. Riemensperger, D. Bucher, J. Ehmer, T. Willer, K. Erbguth, B. Gerber, T. Hendel, G. Nagel, E. Buchner, A. Fiala, Curr. Biol. 2006, 16, 1741).

A mESC line was photosensitized with an optimized ChR2 (ChR2$^{H134R}$) and the cells were subsequently differentiated into motor neurons in order to optically induce action potentials and interrogate the NMJ. This method, recently applied to ESCs overexpressing glia-derived neurotrophic factor (GDNF) for enhanced survival (J. B. Bryson, C. B. Machado, M. Crossley, D. Stevenson, V. Bros-Facer, J. Burrone, L. Greensmith, I. Lieberam, Science (80-.). 2014, 344, 94), foreshadows how any pluripotent cell lines (a fortiori patient-derived iPS cells) can provide consistent optogenetically modified motor neurons. After characterizing the optogenetic targeting of the ESC and the optical excitability of the ChR2$^{H134R}$-ESC-derived motor neurons, their ability to trigger contraction of muscle cells is demonstrated first in a traditional dish assay, as well as in our new three-dimensional compartmentalized microfluidic device.

Figure 11C:
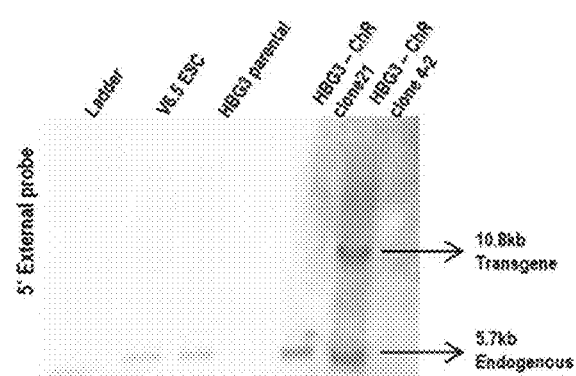
Figure 11D:
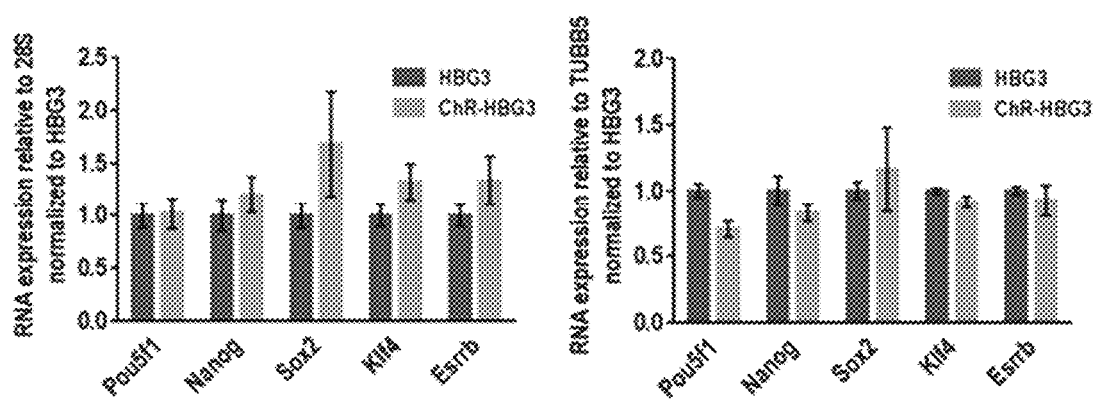

ChR2$^{H134R}$-Expressing mESC Differentiate into Light-activatable Motor Neurons Photosensitization of the mESC line HBG3 (expressing cytosolic GFP under the control of the motor neuron-specific Hb9 promoter) was carried out by knocking in tdTomato-tagged ChR2$^{H134R}$ to the ROSA26 locus via homologous recombination (FIG. 11). One clone, exhibiting a) membrane-bound tdTomato signal, b) ES morphology, and c) single-copy insertion in the ROSA26 locus as evidenced by Southern blotting, was selected (FIG. 5a, FIGS. 11b and c). The transfection process and presence of the transgene had minimal effect on pluripotency of the transgenic ESC line (ChR2$^{H134R}$-HBG3) relative to the parental line (HBG3), as demonstrated by immunostaining of Oct4 (FIG. 5a), and the RNA expression levels of five pluripotency markers (Oct4, Nanog, Sox2, Essrb, Klf4) (FIG. 11d).

Figure 5C:
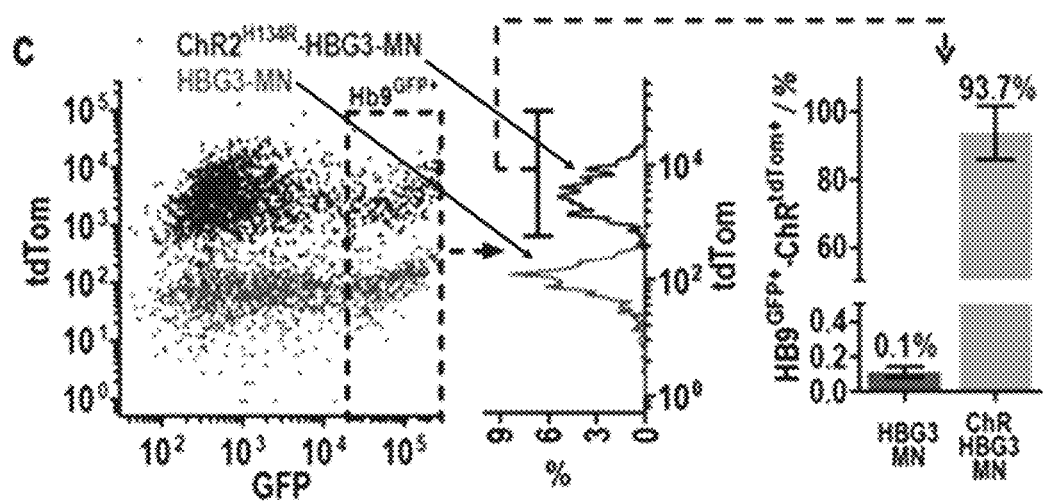

ESC were then differentiated into motor neurons following a published protocol (H. Wichterle, M. Peljto, Curr. Protoc. Stem Cell Biol. 2008, 1) consisting of the formation of embryoid bodies (EB) and exposure to retinoic acid (RA) and smoothened agonist (SAG) (see Methods below). By day 6 of differentiation, motor neurons could be identified by their GFP expression, while retaining a strong expression of tdTomato::ChR2$^{H134R}$ throughout the neurospheres (FIG. 5b). Fluorescence activated cell sorting (FACS) data (green channel for Hb9, red channel for ChR) showed that a large majority of Hb9$^{GFP+}$ neurons still expressed tdTomato::ChR2$^{H134R}$ (93.7±7.9%, n=6) (FIG. 5c), indicating that differentiation does not interfere with transgene expression. Both double positive ChR2$^{H134R}$-HBG3-derived motor neurons (ChR2$^{H134R}$-HBG3-MN) and Hb9$^{GFP+}$ parental HBG3-derived motor neurons (HBG3-MN) extended neurites within minutes following plating and assumed similar neuronal morphologies, suggesting proper development of the ChR2$^{H134R}$-HBG3-MN with respect to their parental line. Most importantly, all ChR2$^{H134R}$-HBG3-MN retained ChR2$^{H134R}$ expression (FIG. 5d) over a period extending beyond 16 days post-plating, indicating no signs of long term silencing of the transgene. As expected, both cytosolic GFP and membrane-bound ChR2$^{H134R}$ were present throughout the entire cell (somata and neurites) (FIG. 5d).

Figure 12A:
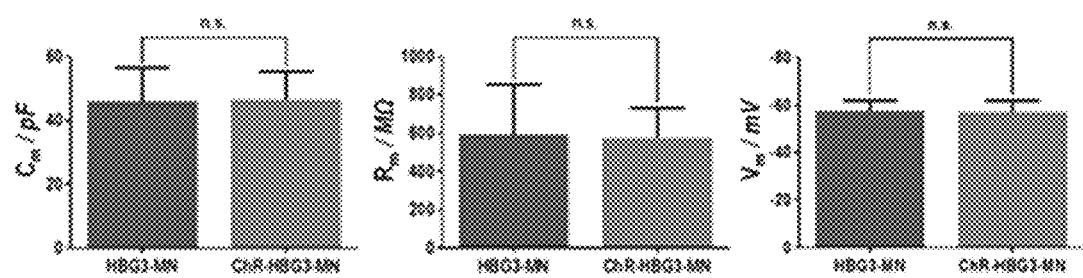
Figure 12B:
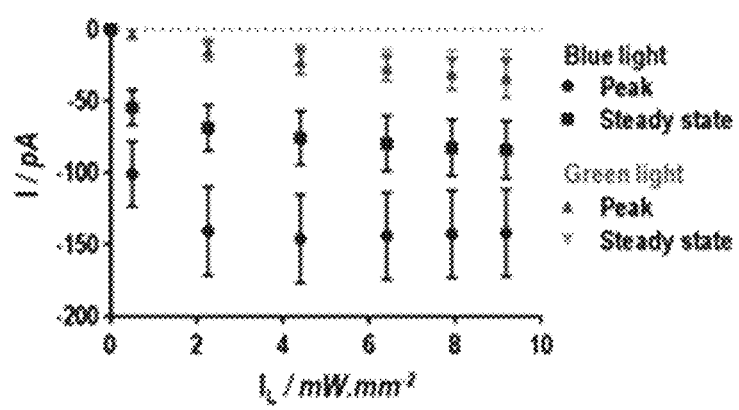
Figure 12C:
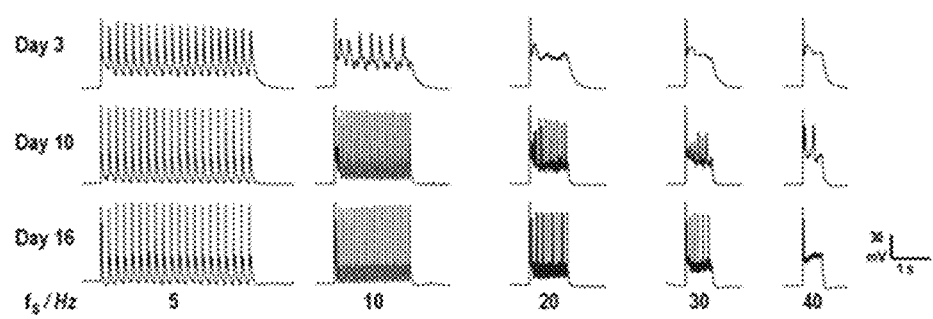
Figure 12D:
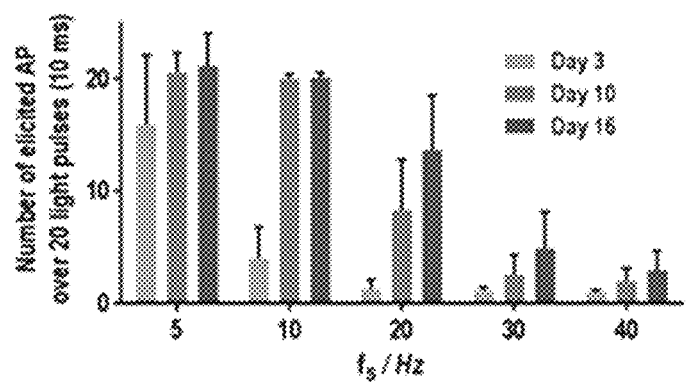
Figure 12E:
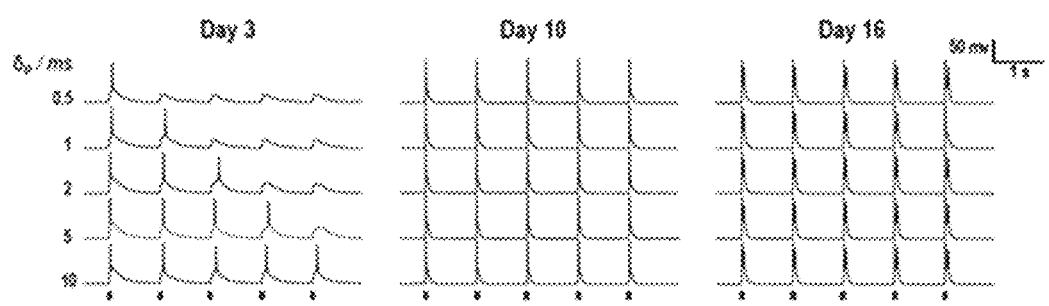
Figure 12F:
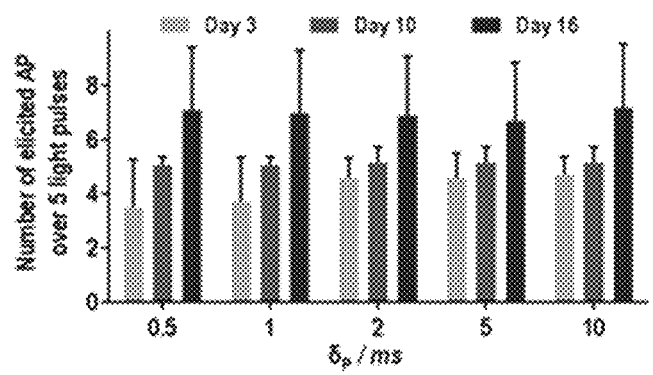

The functionality of channelrhodopsin in ChR2$^{H134R}$-HBG3-MN and its ability to evoke action potentials (AP) was validated by patch clamp. Whole-cell recording was performed on double positive motor neurons on days 3, 10 and 16 post-plating. Resting membrane potential, resistance and capacitance measurements revealed no differences between HBG3-MN and ChR2$^{H134R}$-HBG3-MN (FIG. 12a), suggesting no alteration of the basal electrical properties following ESC targeting, and are consistent with previous reports on HBG3-MN (G. B. Miles, D. C. Yohn, H. Wichterle, T. M. Jessell, V. F. Rafuse, R. M. Brownstone, J. Neurosci. 2004, 24, 7848). Peak ($I_P$) and steady state ($I_{SS}$) photocurrents of the ChR2$^{H134R}$-HBG3-MN during photostimulation were found to be −142±30 pA and −84±20 pA respectively on day 3, reaching −3.8±1.9 nA and −385±71 pA by day 10 and −4.7±1.7 nA and −588±230 pA by day 16 (FIGS. 5e and f), while the ChR-free parental HBG3-MN remained unresponsive to optical stimulation (FIG. 5e). As expected, elicited currents decreased with stimulation light intensity and with a shift of wavelength from blue to green excitation (FIG. 12b). AP could be evoked in all cells from day 3 to day 16 (FIG. 6g). By day 10 and later, trains of AP could be elicited upon sustained illumination, consistent with natural neuronal maturation. Stimulation wavelength, irradiance, pulse frequency and pulse width dependence on inward currents and AP elicitation were also characterized and yielded similar results as previously reported on optogenetically modified primary hippocampal or hES-derived neurons (E. S. Boyden, F. Zhang, E. Bamberg, G. Nagel, K. Deisseroth, Nat. Neurosci. 2005, 8, 1263; J. P. Weick, M. A. Johnson, S. P. Skroch, J. C. Williams, K. Deisseroth, S.-C. Zhang, Stem Cells 2011, 28, 2008) (FIG. 12b-f). These results fully validate the ability to form optically excitable motor neurons from a photosensitized standard mouse embryonic stem cell line.

ChR2$^{H134R}$-HBG3-Derived Motor Neurons can Stimulate Muscle Contraction in Adherent In Vitro Cultures The ability for the ChR2$^{H134R}$-HBG3-MN to form functional NMJs with C2C12-derived skeletal muscles was demonstrated next. This first in vitro demonstration of optically excitable NMJs was conducted using a traditional dish assay, consisting of dissociated MN plated on top of a layer of contractile myotubes, commonly used for MN-muscle cocultures (G. B. Miles, D. C. Yohn, H. Wichterle, T. M. Jessell, V. F. Rafuse, R. M. Brownstone, J. Neurosci. 2004, 24, 7848; J. A. Umbach, K. L. Adams, C. B. Gundersen, B. G. Novitch, PLoS One 2012, 7, e36049). As early as 6 h post-plating, neurite outgrowth could be seen, and by day 1, the first contacts with muscle cells were observed (FIG. 6a). The first muscle contractions could be optically triggered by day 3, consistent with results reported with electrically stimulated NMJ in vitro (J. A. Umbach, K. L. Adams, C. B. Gundersen, B. G. Novitch, PLoS One 2012, 7, e36049). This phenomenon was monitored for another 3 days during which the light-driven muscle contraction persisted (FIGS. 6b and c). This was further confirmed by the inhibition of light-induced muscle contraction in the presence of α-bungarotoxin (αBTX), an acetylcholine receptor (AChR) antagonist (17/17 myocytes showed inhibition) (FIG. 6c). Moreover, the presence of spontaneous twitches after αBTX application was a confirmation that the treatment did not alter the contractility of the myocytes (FIG. 13).

To test the versatility and spatial selectivity of optogenetic stimulation of NMJ, the diameter of the excitation light beam was reduced to ~100 μm, delivering illumination to defined locations in the vicinity of the myotube. When optically exciting one neighboring cluster of motor neurons (FIG. 6ci, region 3), no contraction was observed (FIG. 6cii, trace 2), a result similar to the one obtained by illuminating the muscle cell alone (FIG. 6Ci, region 2, FIG. 6Cii, trace 3), indicating that that particular cluster of neurons did not form functional NMJs with that myotube). However, when illuminating the innervating neuron cluster (FIG. 6Ci, region 4), the muscle exhibited the same contraction pattern as when the whole field of view was uniformly stimulated (FIG. 6dii, traces 1 and 4), illustrating the selectivity of optogenetic stimulation and showing how localized optical excitation can help decipher connectivity patterns.

Design and Assembly of the Microfluidic Platform for Three-dimensional Compartmentalized Neuron-Muscle Coculture.

The new three-dimensional platform developed in this study alleviates the common limitations of 2D NMJ cultures in that it allows for the compartmentalized coculture of motor neurons and myofibers in a mechanically compliant matrix. Neuromuscular tissues were created in a Polydimethylsiloxane (PDMS)-based device consisting of two parts (FIG. 7). The top microfluidic section is patterned with 3 gel regions flanked with two medium channels (FIG. 7a). The left (receiving the neurospheres) and middle gel regions are both 0.5 mm in width while the right 1 mm-wide channel will receive the muscle strip (FIGS. 7a and c). Each channel is separated from its neighbors by a row of posts, which provide confinement during gel and cell seeding while still allowing cell-cell signaling and nutrient supply. The height of the channels is 320 μm throughout the device, allowing for the tissue to experience a full three-dimensional environment. A necking of the gel region allows for the formation of 2 independent and isolated tissues, each ~1 mm long (FIG. 7a), doubling the throughput of the platform. The bottom section of the platform is a thin membrane of PDMS (~100 μm), bonded to a coverslip for rigidity, featuring 2 sets of 2 capped pillars (FIG. 7b). The 15 μm difference between the top of the pillar and the roof of the channel allows for pillar deflection. Following proper sterilization, the platform is assembled by affixing the top section to the bottom one such that the pillars line up in the center of the muscle channels (FIGS. 7a and c) (see Methods). This design is unique in its ability to culture motor neurons and muscle cells in a three-dimensional environment, while keeping them physically separated. This facilitates the monitoring of axonal outgrowth in a functional context, and potentially providing cell-specific factors or drugs.

Neuromuscular Coculture in the Microfluidic Device

Figure 8:
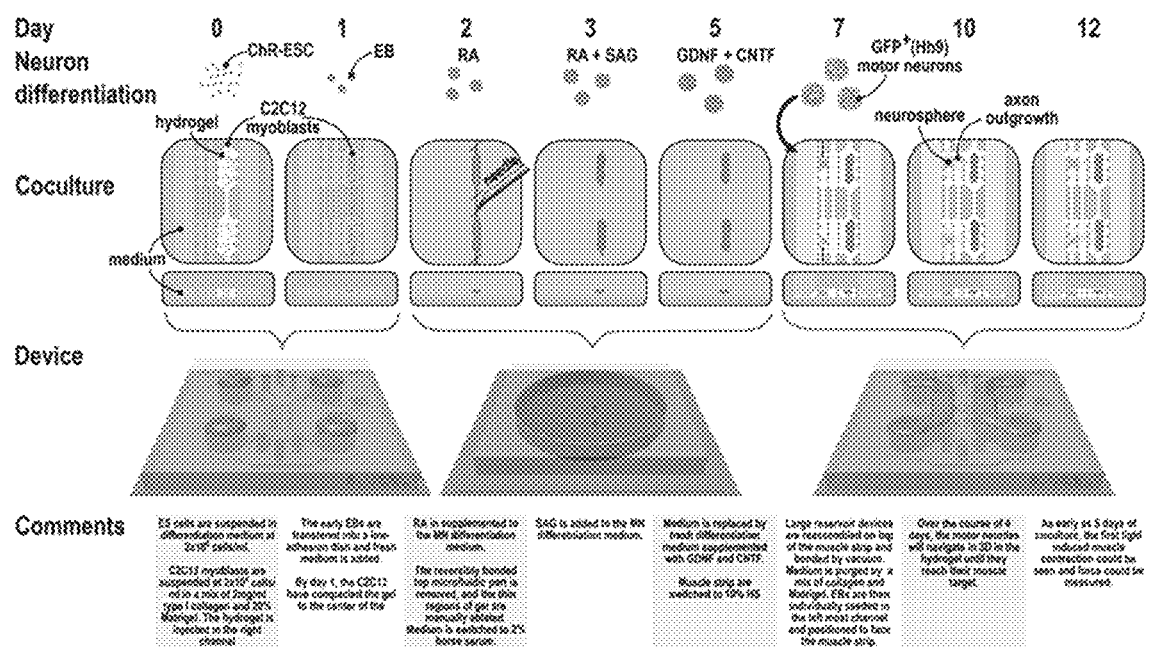
FIG. 8 is a cartoon showing a framework for the microfluidic neuromuscular coculture. (row 1) Schematic of the differentiation process of the ES into motor neurons following a previously published protocol (H. Wichterle, M. Peljto, Curr. Protoc. Stem Cell Biol. 2008, 1). (row 2) Schematics displaying the top and front views of the tissue in the microfluidic platform. (row 3) three-dimensional CAD illustration of the version of the platform used at the corresponding days.

The following stepwise seeding procedure was optimized to account for the highly contractile nature of the myoblasts which prevented simultaneous co-seeding and in situ co-differentiation of both cell types (FIG. 8). First, C2C12 cells, suspended in a collagen-Matrigel solution, were seeded into the rightmost channel of the device containing the pillars (FIG. 7c, 4, day 0). Following gel compaction (FIG. 8, day 1), resulting in gel fiber rearrangement and myoblast alignment (Y. Morimoto, M. Kato-Negishi, H. Onoe, S. Takeuchi, Biomaterials 2013, 34, 9413; M. S. Sakar, D. M. Neal, T. Boudou, M. a Borochin, Y. Li, R. Weiss, R. Kamm, C. S. Chen, H. H. Asada, Lab Chip 2012, DOI 10.1039/c21c40338b), thin pieces of tissue remained, connecting the muscle strips together and to the gel filling ports, preventing them from contracting independently from each other. To allow pillar deflection upon muscle contraction, the separation and mechanical decoupling of the muscle strips was accomplished by a manual ablation. Another technique involving two-photon laser excitation was also developed and is described in more detail in the Methods section below. After removing the reversibly bonded top layer of the device, a needle was used to perform incisions to the muscle strips at a distance of ~500 μm from the pillar (FIG. 8, day 2). The total resorption of the small "tails" left by the ablation was completed over the following day, resulting in well-delineated muscle bundles (FIGS. 14b and c). After ablation, differentiation was induced by switching to a myogenic differentiation medium. Expression of α-actinin and formation of striated sarcomeric structures, indicative of proper differentiation, were visualized by immunostaining and confocal imaging (FIG. 9a). The muscle bundle exhibited an initial 75% compaction following seeding, reaching ~85% on day 6, and its width finally stabilized to 25% of the original dimension (FIG. 9b).

Figure 15A:
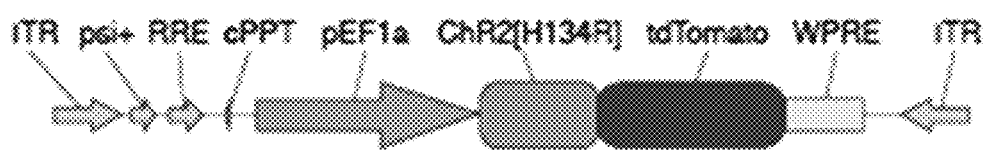
Figure 15B:
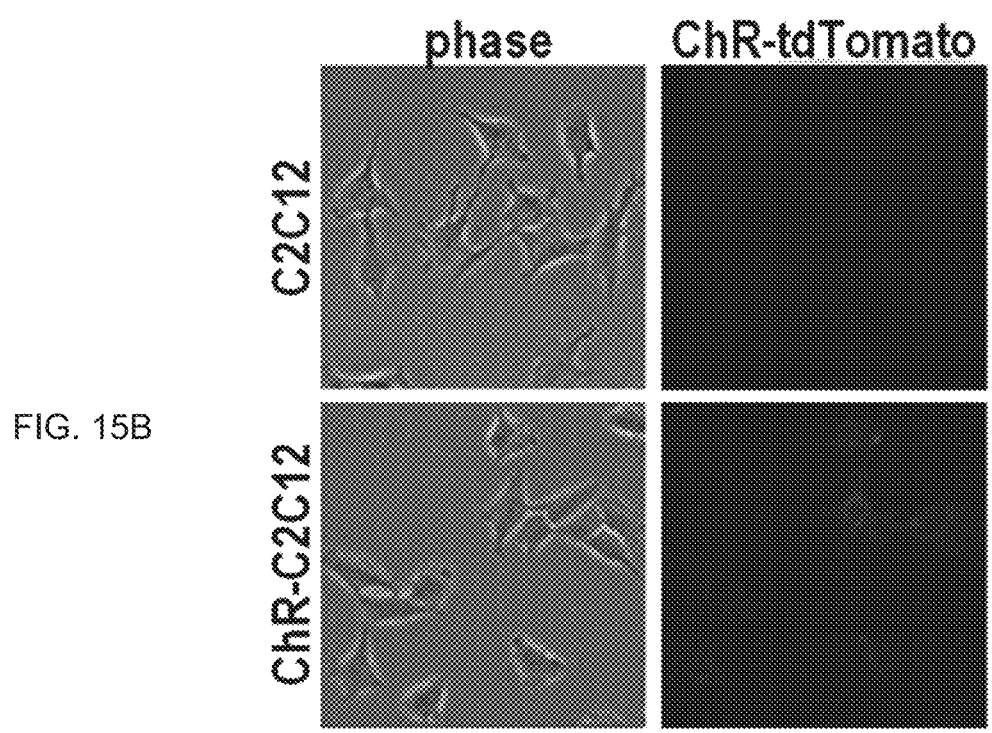
Figure 15C:
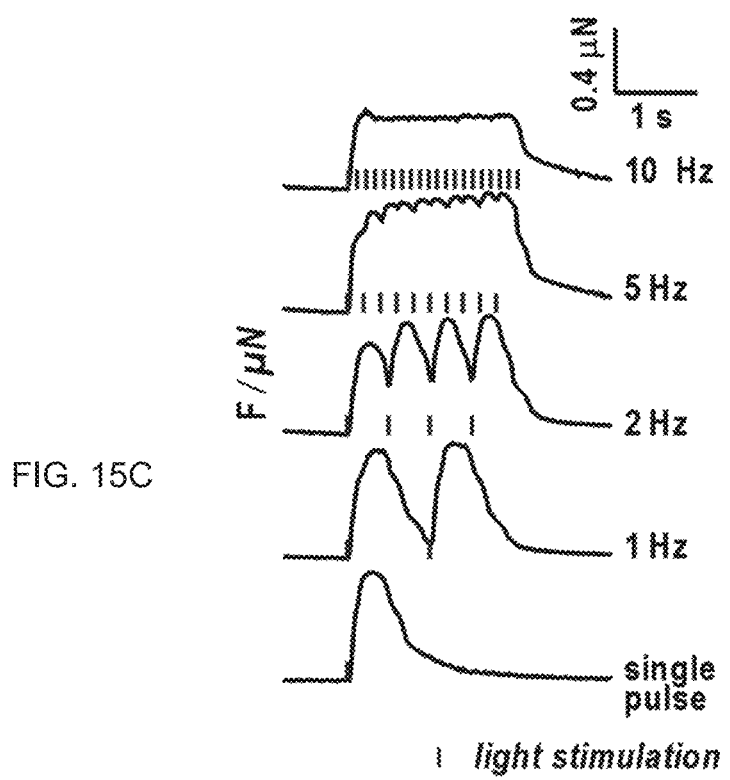
Figure 15D:
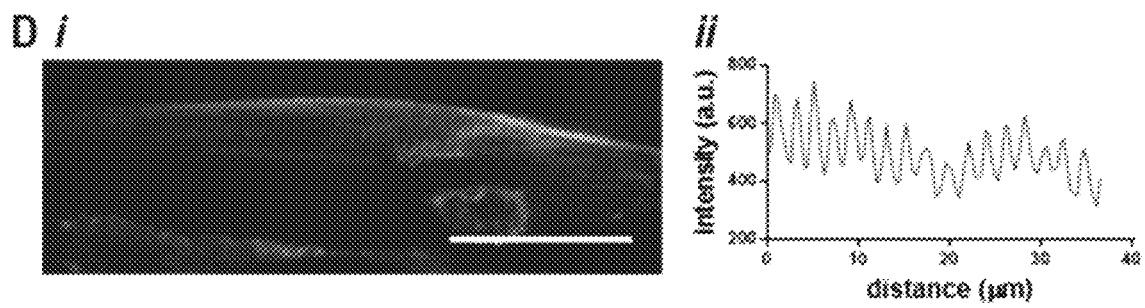

To monitor contractile activity and functionally assess myogenic differentiation, C2C12 cells were optogenetically modified and the muscle strips derived from these cells were optically stimulated (FIG. 15) (the C2C12 photosensitization was performed similarly to previous studies (M. S. Sakar, D. M. Neal, T. Boudou, M. a Borochin, Y. Li, R. Weiss, R. Kamm, C. S. Chen, H. H. Asada, Lab Chip 2012, DOI 10.1039/c21c40338b; T. Asano, T. Ishizua, H. Yawo, Biotechnol. Bioeng. 2012, 109, 199), see Methods). Light-induced contractions were first observed on day 3 post-induction. Throughout the entire process, passive tension ($F_P$) and active contraction ($F_A$) were measured by monitoring pillar deflection (see Methods). Both were comparable to those measured in previous in vitro platforms (M. S. Sakar, D. M. Neal, T. Boudou, M. a Borochin, Y. Li, R. Weiss, R. Kamm, C. S. Chen, H. H. Asada, Lab Chip 2012, DOI 10.1039/c21c40338b; S. Hinds, W. Bian, R. G. Dennis, N. Bursac, Biomaterials 2011, 32, 3575), with passive tension reaching a plateau after day 7 at ~18 µN and tetanus occurring at 10 Hz (FIG. 9c, FIG. 15c). Overall, there was no evidence to suggest that confinement of the myoblasts to a microfluidic chamber altered myogenesis.

Neuron-muscle cocultures in the microfluidic devices were initiated by seeding the $ChR2^{H134R}$-HBG3-derived neurospheres into the device after 7 days of differentiation (FIG. 8, day 7). After reassembling an open-reservoir variant of the microfluidic device onto the muscle strip, the medium contained in all channels was flushed with a collagen-Matrigel mix. Neurospheres ~300 to 400 µm in diameter were manually selected, resuspended with the same collagen-Matrigel mixture as above, and individually pipetted into the leftmost channel (FIG. 9d and FIG. 8) before the devices were placed in the incubator for matrix gelation, after which medium was supplied to both open reservoirs. The diameter of the neurospheres being greater than the inter-post distance ensured their restriction to the assign channel, resulting in a physical separation of ~1 mm between the neurons and the muscles.

Since this platform is the first to create a matrix-embedded muscle strip anchored to compliant pillars, as opposed to the existing stand-alone ones suspended in medium (H. Vandenburgh, J. Shansky, F. Benesch-Lee, V. Barbata, J. Reid, L. Thorrez, R. Valentini, G. Crawford, Muscle Nerve 2008, 37, 438; W. R. Legant, A. Pathak, M. T. Yang, V. S. Deshpande, R. M. McMeeking, C. S. Chen, Proc. Natl. Acad. Sci. U.S.A 2009, 106, 10097), the effect of the presence of the gel on the force exerted by the muscle on the pillars was characterized. This was achieved by measuring the force applied to the pillars before and after gel seeding (based on the assumption that the force generated by the muscle is not altered during the ~20 min polymerization process). Considering the poroelastic properties of hydrogel, its mechanical contribution was anticipated to bias the force measurement (FIG. 16a). However, results revealed no significant changes in the peak or steady-state force, along with the rate of force increase (FIGS. 16b and c), suggesting that the contributions of the viscoelastic/poroelastic properties of the gel were negligible. Therefore, the force generated by the muscle strip can be determined from pillar deflection without correcting for matrix viscoelasticity.

One day after seeding, motor neurites could be seen extending from the neurospheres, as evidenced by the presence of $Hb9^{GFP+}$ processes in the gel (FIG. 9e). All $Hb9^{GFP+}$ neurites were also positive for $ChR2^{H134R}$, confirming once more minimal silencing of the transgene. Some $Hb9^{GFP-}$/$ChR^{tdTom+}$ neurites were also observed (FIG. 17a), indicative of the presence of non-MN cells, most likely interneurons as previously reported in HBG3 ESCs differentiated under similar conditions (H. Wichterle, I. Lieberam, J. a Porter, T. M. Jessell, Cell 2002, 110, 385).[43] Maximum axon outgrowth rate was measured to be 10.4±5.6 µm·h$^{-1}$ over the course of the first 4 days [consistent with axon three-dimensional outgrowth reported in the literature (R. Pittier, F. Sauthier, J. A. Hubbell, H. Hall, Journal of neurobiology 2005, 63, 1; R. K. Willits, S. L. Skornia, J. Biomater. Sci. Polym. Ed. 2004, 15, 1521)], after which all muscle strips were contacted by motor axons (FIGS. 9e and f). Interestingly, the direction and rate of outgrowth were not found to be biased by the presence of the muscle strip (FIG. 17b). Spatial segregation of the two cell types provides a unique opportunity to visualize the three-dimensional axon outgrowth towards the muscle. Confocal imaging was used to assess the distribution of extended neurites within the thickness of the gel at different stages of the coculture (FIG. 9g). Images reveal that no plane was preferred for neurite outgrowth as the extended homogeneously throughout the gel.

$ChR2^{H134R}$-HBG3-Derived Motor Neurons Remotely Innervate Myofibers and Activate Muscle Contraction Upon Illumination in Three-Dimensional Microfluidic Device Glutamate, the natural excitatory neurotransmitter for lower motor neurons and commonly used to demonstrate the presence of functional NMJs, was added to the medium at a concentration of 400 µM and introduced to the leftmost channel of the device, adjacent to the gel region which houses the neurospheres. The first muscle contraction, indicative of the presence of functional NMJs, was recorded 80 s after glutamate administration and the twitching frequency rose during the subsequent 120 s to reach a steady value of ~1.25 Hz (FIG. 10a). The delay in contraction and increase of the twitching frequency is likely due to the diffusion of the glutamate to the motor neurons embedded in the ECM since this lag is absent in adherent 2D cultures (T. Wada, M. Honda, I. Minami, N. Tooi, Y. Amagai, N. Nakatsuji, K. Aiba, PLoS One 2009, 4, DOI 10.1371/journal.pone.0006722) or three-dimensional constructs in suspension (Y. Morimoto, M. Kato-Negishi, H. Onoe, S. Takeuchi, Biomaterials 2013, 34, 9413).

Use of our $ChR2^{H134R}$-HBG3-MN enabled faster and more controllable muscle stimulation. Light-driven muscle contraction could be recorded 5 days following neurosphere seeding (day 12), with no discernable patterns in amplitude or frequency, and persisted until the end of the 16-day experiment period, demonstrating the robust nature of the NMJs in this device (FIG. 10b). Contractile forces measured by the compliant pillars were on the order of ~1.5 µN, comparable to those obtained by glutamate stimulation. Similar to the 2D case, application of αBTX inhibited muscle contraction, confirming the functionality of NMJs in the three-dimensional device (FIG. 10b). Moreover, the distal part of motor axons were observed to colocalize with αBTX-stained AChR, a visual assessment of the presence of NMJs (FIG. 10c). Sustained light illumination was found to generate multiple muscle twitches (FIGS. 10b and d), with frequency increasing as the stimulation light intensity increased (FIGS. 10d and e), consistent with the patterns of trains of AP elicitation under the same stimulation conditions (FIG. 5). However, no muscle tetanus could be generated. The maximum force generated via neuronal stimulation (chemical or optical) was found to yield forces 70% of the maximum force that could be generated via electrical excitation or by optically stimulating $ChR2^{H134R}$-exposing C2C12-derived muscle bundles suggesting an incomplete innervation of the whole muscle strips by the same factor (assuming all myofibers can generate similar levels of contraction).

Microfluidic Platform for the Formation of Optically Excitable 3-D Compartmentalized Motor Units The combination of microfluidic and optogenetic technologies has enabled development of a highly controllable and physiologically relevant in vitro model for motor units with applications ranging from fundamental scientific studies to drug screening assays. Light stimulation of Channelrhodopsin-expressing ES-derived motor neurons provides great versatility over the excitation of the tissue by making it cell specific and more spatiotemporally resolved than chemical stimulation. The PDMS-based microfluidic platform provides the first in vivo-like three-dimensional compartmentalized neuron-muscle coculture with functional force readout.

The microfluidic chambers provide a three-dimensional configuration similar to that of the native tissue, where one channel serves as a surrogate for the spinal cord while the other one models the remotely innervated muscle tissue as found in the body wall or limbs. This culture system confers not only a softer mechanical substrate which 2D systems often lack, but also the ability to investigate the role of the surrounding ECM. Compartmentalization further facilitates visualization of axonal outgrowth and innervation through a relevant matrix or the supply of cell specific chemical cues and would allow for the manipulation of axons without interfering with other cell types. Finally, the integration of force sensors to the design offers a live, non-invasive and quantitative assessment of muscle differentiation and contraction and synapse function.

First, the ability to photosensitize non-altered ESCs and differentiate them into optically excitable motor neurons raises the potential for more versatile ways of investigating disease models such as SMA or ALS by delivering ChR to the commercially available patient-derived iPS cells, already shown to be differentiable into functional motor neurons (A. D. Ebert, J. Yu, F. F. Rose, V. B. Mattis, C. L. Lorson, J. a Thomson, C. N. Svendsen, Nature 2009, 457, 277; J. T. Dimos, K. T. Rodolfa, K. K. Niakan, L. M. Weisenthal, H. Mitsumoto, W. Chung, G. F. Croft, G. Saphier, R. Leibel, R. Goland, H. Wichterle, C. E. Henderson, K. Eggan, Science 2008, 321, 1218). A process that could be combined with recent advances in transcriptional programming that drastically increase the yield and decrease the duration of motor neuron differentiation from human and mouse ESC (E. O. Mazzoni, S. Mahony, M. Closser, C. a Morrison, S. Nedelec, D. J. Williams, D. An, D. K. Gifford, H. Wichterle, Nat. Neurosci. 2013, 16, 1219; M. E. Hester, M. J. Murtha, S. Song, M. Rao, C. J. Miranda, K. Meyer, J. Tian, G. Boulting, D. V Schaffer, M. X. Zhu, S. L. Pfaff, F. H. Gage, B. K. Kaspar, Mol. Ther. 2011, 19, 1905).

This demonstration of optically controlled NMJs in vitro has wide applicability in diverse fields. For instance, much is yet to be understood regarding the process of NMJ maturation and remodeling, specifically how activity or exercise is responsible for plastic synaptic adaptation (P. G. Nelson, R. D. Fields, C. Yu, Y. Liu, J. Neurobiol. 1993, 24, 1517). The ability to selectively excite motor neurons or muscle cells [by selectively expressing ChR in one or the other, or taking advantage of wavelength-specific opsin variants (O. Yizhar, L. E. Fenno, T. J. Davidson, M. Mogri, K. Deisseroth, Neuron 2011, 71, 9)] greatly facilitates identifying the contributions of each synaptic partner in their anterograde and retrograde signaling (A.-S. Arnold, J. Gill, M. Christe, R. Ruiz, S. McGuirk, J. St-Pierre, L. Tabares, C. Handschin, Nat. Commun. 2014, 5, 3569; R. M. Fitzsimonds, M. M. Poo, Physiol. Rev. 1998, 78, 143; R. M. Wyatt, R. J. Balice-Gordon, J. Neurocytol. 2004, 32, 777).

Applications are also useful in the fields of soft robotics or nanorobotics, defined as microfabricated motile substrates actuated by muscle cells recapitulating locomotive tasks (J. C. Nawroth, H. Lee, A. W. Feinberg, C. M. Ripplinger, M. L. McCain, A. Grosberg, J. O. Dabiri, K. K. Parker, Nat. Biotechnol. 2012, 30, 792; C. Cvetkovic, R. Raman, V. Chan, B. J. Williams, M. Tolish, P. Bajaj, M. S. Sakar, H. H. Asada, M. T. a Saif, R. Bashir, Proc. Natl. Acad. Sci. U.S.A 2014, 2; B. J. Williams, S. V Anand, J. Rajagopalan, M. T. a Saif, Nat. Commun. 2014, 5, 3081; V. Chan, K. Park, M. B. Collens, H. Kong, T. a Saif, R. Bashir, Sci. Rep. 2012, 2, 857). The use of optogenetic motor neurons provides a level of spatiotemporal control capable of emulating the fine input command of the motor cortex.

The device and methods described herein overcome many of the drawbacks of earlier systems. Overcoming the challenges of co-culturing motor neurons and skeletal muscle cells in a microfluidic device, featuring a compliant three-dimensional matrix and in a spatially organized and compartmentalized fashion, brought the optogenetic NMJs from a traditional culture system to a more in vivo-like microenvironment. The confinement by a microfluidic chamber did not impair myogenesis, and neither did the presence of the surrounding hydrogel. The spontaneous axonal outgrowth allowed for a remote innervation and emergence of light-excitable NMJs. While the isotropic neurite outgrowth could be the result of too weak a chemotactic gradient generated by the muscle-derived factors, another explanation is that the motor neurons are not mature enough to express the appropriate chemoattractant receptor or that the subtype of motor neurons thus differentiated is irresponsive to the factors secreted by the muscle cell (D. Bonanomi, S. L. Pfaff, Cold Spring Harb. Perspect. Biol. 2010, 2, a001735; S. Nedelec, M. Peljto, P. Shi, M. W. Amoroso, L. C. Kam, H. Wichterle, J. Neurosci. 2012, 32, 1496; a Ebens, K. Brose, E. D. Leonardo, M. G. Hanson, F. Bladt, C. Birchmeier, B. a Barres, M. Tessier-Lavigne, Neuron 1996, 17, 1157). The ability to isolate the motor somata from the muscle cells is crucial for imaging the navigation of axons within a wide extracellular space is useful in further understanding the process of nerve degeneration and repair in a functional context. Moreover, with some further engineering of the muscle consisting of fluorescently tagging the acetylcholine receptors (S. Gensler, A. Sander, A. Korngreen, G. Traina, V. Witzemann, Assembly and clustering of acetylcholine receptors containing GFP-tagged e or g subunits. Eur. J. Biochem. 268, 2209-2217 (2001)) or postsynaptic scaffolding proteins such Rapsyn (O. L. Gervásio, W. D. Phillips, Increased ratio of rapsyn to ACh receptor stabilizes postsynaptic receptors at the mouse neuromuscular synapse. J. Physiol. 562, 673-85 (2005)), one could monitor the time course of synapse remodeling upon motor neuron or muscle stimulation.

This feature is also the first of its kind to allow for providing each cell type with its own medium in such a three-dimensional environment in the form of 2 opposite gradients (as demonstrated with fluorescent tracers (FIG. 18)). This medium segregation enhances neuromuscular tissue survival and NMJ maturation in vitro, which is beneficial for long term NMJ cultures (S. R. Thomson, T. M. Wishart, R. Patani, S. Chandran, T. H. Gillingwater, J. Anat. 2012, 220, 122). Besides, this asymmetry of chemokines supply can be used in a variety of applications, from testing the influence of cytokine gradients in the context of spinal cord development and axon pathfinding to the supply of cell-specific drugs.

While contact between motor neurites and muscle bundles was observed by day 4 of coculture in all tissues, only ~50% of the muscle constructs could be stimulated via neuronal excitation and the resulting force was 40% of the maximum force generated by total myofiber recruitment. This moderate success rate in generating functional light excitable neuromuscular junctions and incomplete innervation is likely attributable to poor accessibility of the myofibers to the incoming growth cone, since some were found within the muscle bundle. A solution to this problem could be to form multiple thinner muscle strips, which would provide more entry points to incoming axons (D. Neal, M. S. Sakar, L.-L. S. Ong, H. Harry Asada, Lab Chip 2014, DOI 10.1039/c41c00023d; V. Chan, D. M. Neal, S. G. M. Uzel, H. Kim, R. Bashir, H. H. Asada, Lab Chip 2015, DOI 10.1039/C5LC00222B). Moreover, the resulting force that was 70% of the maximum force generated by total myofiber recruitment could find an extra explanation in that fact that tetanus could not be observed in muscle bundles stimulated by the motor neurons (while they were via direct electrical excitation). Although consistent with the existing studies conducted on NMJ formed in vitro with either C2C12 or primary myoblasts (M. Das et al., Embryonic motoneuron-skeletal muscle co-culture in a defined system. Neuroscience. 146, 481-8 (2007), E. E. Zahavi et al., A compartmentalized microfluidic neuromuscular co-culture system reveals spatial aspects of GDNF functions. J. Cell Sci. 128, 1241-1252 (2015), Y. Morimoto, M. Kato-Negishi, H. Onoe, S. Takeuchi, Three-dimensional neuron-muscle constructs with neuromuscular junctions. Biomaterials. 34, 9413-9 (2013), A. S. T. Smith, C. J. Long, K. Pirozzi, J. J. Hickman, A functional system for high-content screening of neuromuscular junctions in vitro. Technology. 1, 37-48 (2013)), these systems could benefit from both recent myogenesis protocols from heterogeneous primary muscle cultures resulting in physiologic force generation (M. Juhas, G. C. Engelmayr, a. N. Fontanella, G. M. Palmer, N. Bursac, Biomimetic engineered muscle with capacity for vascular integration and functional maturation in vivo. Proc. Natl. Acad. Sci., 1-6 (2014)), and genetically modified GNDF-expressing ESC-derived motor neurons leading to higher survival and firing rate (J. B. Bryson et al., Optical Control of Muscle Function by Transplantation of Stem Cell-Derived Motor Neurons in Mice. Science (80-.). 344, 94-97 (2014)).

To further increase the physiological relevance of the system, other cells types are added to the culture. This could be done by taking advantage of, or even tuning, the heterogeneity of the differentiated cells within the neurospheres (the non-MN ChR2-expressing cells in FIG. 17A are likely to be interneurons interacting via excitatory or inhibitory signals) or by complementing the surrounding matrix with supporting cells. For instance, Schwann cells, responsible for axon guidance, myelination, nerve repair (Y. J. Son, W. J. Thompson, Neuron 1995, 14, 125) or NMJ formation and function (E. M. Ullian, B. T. Harris, A. Wu, J. R. Chan, B. a Barres, Mol. Cell. Neurosci. 2004, 25, 241; G. Cao, C.-P. Ko, J. Neurosci. 2007, 27, 6712) are added to the surrounding hydrogel. Doing so also provides functional and quantitative insight in the myelination process along with demyelinating neuropathies such as the Guillain-Barre syndrome (R. a C. Hughes, D. R. Cornblath, Lancet 2005, 366, 1653) or Charcot-Marie-Tooth disease (A. S. D. Saporta, S. L. Sottile, L. J. Miller, S. M. E. Feely, C. E. Siskind, M. E. Shy, Ann. Neurol. 2011, 69, 22).

The integration of compliant micropillars as anchoring points for the muscle bundles allows for a rapid, passive and non-invasive assessment of muscle passive tension and active contraction. In a drug screening assay, this contractile functional output provides a means of assessing the downstream and cumulative efficacy of a drug on motor unit recovery, a method employed in the past in muscle bundle cultures and termed High Content Screening (H. Vandenburgh, Tissue Eng. Part B. Rev. 2010, 16, 55). The high throughput or multiplex aspects of the system (e.g., a plurality of co-culture chambers) is useful as an organ-on-a-chip (C. Luni, E. Serena, N. Elvassore, Curr. Opin. Biotechnol. 2014, 25, 45). Such systems are useful to elucidate cell signaling mechanisms as well as for screening tools to identify therapeutic agents as such multichannel 3-D microfluidic cell culture chips simulate the activities, mechanics and physiological responses of entire organs and organ systems.

This example presents an in vitro platform allowing simultaneous three-dimensional and compartmentalized coculture of mouse embryonic stem cells (mESC)-derived motor neurons and skeletal muscle cells, within an extracellular matrix. This example capitalizes on microfluidic designs for three-dimensional cell culture (V. Vickerman, J. Blundo, S. Chung, R. Kamm, Lab Chip 2008, 8, 1468; Y. Shin, S. Han, J. S. Jeon, K. Yamamoto, I. K. Zervantonakis, R. Sudo, R. D. Kamm, S. Chung, Nat. Protoc. 2012, 7, 1247; B. Mosadegh, C. Huango, J. W. Park, H. S. Shin, B. G. Chung, S. K. Hwang, K. H. Lee, H. J. Kim, J. Brody, N. L. Jeon, Langmuir 2007, 23, 10910), and the use of passive force transducers for quantitative measurement of muscle contraction (H. Vandenburgh, J. Shansky, F. Benesch-Lee, V. Barbata, J. Reid, L. Thorrez, R. Valentini, G. Crawford, Muscle Nerve 2008, 37, 438; W. R. Legant, A. Pathak, M. T. Yang, V. S. Deshpande, R. M. McMeeking, C. S. Chen, Proc. Natl. Acad. Sci. U.S.A 2009, 106, 10097) (reviewed in ref. S. G. M. Uzel, A. Pavesi, R. D. Kamm, Prog. Biophys. Mol. Biol. 2014, 1). The system enables the culture of functional differentiated motor neurons and myofibers, the observation of three-dimensional axonal outgrowth with the hydrogel and the formation of functional NMJs.

The following materials and methods were used to generate the data described herein.

Microfluidic Device Fabrication

The mold fabrication followed a process similar to previously reported (V. Vickerman, J. Blundo, S. Chung, R. Kamm, Lab Chip 2008, 8, 1468; Y. Shin, S. Han, J. S. Jeon, K. Yamamoto, I. K. Zervantonakis, R. Sudo, R. D. Kamm, S. Chung, Nat. Protoc. 2012, 7, 1247). Briefly, designs were generated using AutoCAD (Autodesk, CA) and the patterns were transferred to a Mylar transparency mask using high-resolution printing (FineLine Imaging, CO). Silicon wafers were then fabricated by photolithography using SU-8 photoresist (MicroChem, MA). Unlike the top microfluidic part of the device that was casting from a negative mold, the master for the bottom pillar part was a positive version of it. All molds were surface treated overnight prior to any polydimethylsiloxane (PDMS) (Ellsworth Adhesives, MA) casting using (Tridecafluoro-1,1,2,2-Tetrahydrooctyl)-1-Trichlorosilane (United Chemical Technologies, PA). For the top microfluidic part, PDMS, mixed at 10:1 base:curing agent, was poured onto the silicon mold at a height of 5 mm, degassed in a desiccator and cured at 80° C. for at least 4 h. Devices were then cut off the mold, trimmed to the appropriate size, and gel filling ports, vacuum port and medium ports/reservoirs were formed with 1, 2 and 4 mm diameter biopsy punches, respectively. For the bottom pillar part, a negative version of the mold was made with PDMS mixed at a 5:1 base:curing agent. It was then silanized overnight and the same PDMS mixture was spun on top of the negative mold for 10 seconds at 500 rpm and 15 seconds at 1,000 rpm, yielding membranes with thicknesses of ~100 µm. The membrane featuring the pillars was gently peeled off. Each pillar had a slight conical shape, reminiscent of the microfabrication process, with basal and tip diameters of 75 µm and 100 µm, respectively, and a height of 280 µm. Membrane pillar devices were then bonded to a 20×20 mm coverslip by plasma activation (Harrick Plasma, NY) for rigidity purposes. The caps of the pillars consisted of 150×

150 µm squares of 25 µm thin PDMS (obtained by spin coating it on a 10 cm Petri dish for 30 s at 5,000 rpm), manually positioned over the pillar and glued with uncured PDMS, which resulted in a final height of 305 µm. Both top and bottom parts of the device were then cleaned by sonication in a bath of ethanol, followed by a sonicated bath of DI water. They were then sterilized by a cycle of wet autoclaving, followed by dry autoclaving. The parts were aligned and assembled using a stereomicroscope under sterile conditions. After usage, devices were cleaned by sonication in ethanol then DI water and sterilized with wet then dry autoclaving and stored in a sterile container before further use. No devices were used more than 10 times.

Cell Culture and Differentiation

The cell lines used and described herein are art-recognized models for functional cells, tissues, organs in mammals such as human subjects.

Source Cells

Mouse embryonic stem cell line HBG3 (Hb9-GFP) were kept in culture on a feeder layer of mouse embryonic fibroblasts (CF-1 MEF Feeder Cells Applied StemCell) plated on 0.1% gelatin coated dishes in undifferentiated medium consisting of Embryomax ES DMEM (Millipore Chemicon), 15% embryonic stem cell qualified fetal bovine serum (Invitrogen), 1% nucleosides (Millipore Chemicon), 1% non-essential amino acids (Millipore Chemicon), 1% penicillin-streptomycin (Invitrogen), 1% L-glutamine (Invitrogen), 0.1 mM β-mercaptoethanol (Sigma), 0.1% Leukemia inhibitory factor (EMD). Mouse myoblasts C2C12 (D. Yaffe, O. Saxel, Nature 1977, 270, 725) (ATCC) were cultured below 70% confluency in growth medium consisting of high glucose DMEM (ATCC), 10% FBS (Invitrogen), 1% penicillin-streptomycin. All cells were kept in incubators at 37° C. and 5% $CO_2$. None of the cells were used beyond a passage number 20.

Motor Neurons

The motor neuron differentiation protocol was adapted from published literature (H. Wichterle, M. Peljto, Curr. Protoc. Stem Cell Biol. 2008, 1). Briefly, mESC were collected from their feeder layer culture and plated at $2\times10^6$ cells in 10 ml in a 10 cm Nunc culture dish in differentiation medium, consisting of 1:1 Advanced DMEM/F-12 (Invitrogen)/Neurobasal (Invitrogen), 10% Knockout Serum replacement (Invitrogen), 1% penicillin-streptomycin (Invitrogen), 1% L-glutamine (Invitrogen), 0.1 mM β-mercaptoethanol (Sigma). They were allowed to form embryoid bodies (EB) overnight. The next day, EBs in suspension were collected and transferred to low-adhesion culture dishes in 10 ml of differentiation; the cells that had attached to the Nunc dishes were discarded. On day 2, medium was changed and supplemented with 1 µM retinoic acid (Sigma), and on day 3, with 1 µM of smoothened agonist (EMD). The cells remained in this medium for 2 more days. On day 5, medium was replaced by differentiation medium supplemented with 10 ng·ml$^{-1}$ of glia derived neurotrophic factor (GDNF) (R&D systems) and 10 ng·ml$^{-1}$ ciliary neurotrophic factor (CNTF) (R&D systems). EBs were used on day 7, either seeded in the microfluidic devices or dissociated and FACS-sorted to isolate Hb9$^{GFP+}$/ChR$^{tdTom+}$ motor neurons for plating on glial feeder layer or muscles cell in 2D cultures.

Motor Neuron—Glial Cells Coculture for Electrophysiological Recordings

Petri dishes (35 mm, BD science) were coated with a Poly-D-Lysine (Sigma) coating solution at a concentration of 200 µg·ml$^{-1}$ and incubated at 37° C. overnight. After washing the PDL solution with DI water, a laminin coating solution (Invitrogen) at a concentration of 10 µg·ml$^{-1}$ for at least 4 h. Laminin coating solution was rinsed once before glial cells were plated at ~$1\times10^5$ cells/dish and allowed to form a monolayer over at least 5 days in high-glucose DMEM (ATCC) containing 10% horse serum (HS) (Invitrogen) and 1% penicillin-streptomycin (Invitrogen). Dissociated motor neurons were then plated at a $1\times10^5$ cells/dish and medium was switched to motor neuron growth medium supplemented with GDNF at 10 ng·ml$^{-1}$, CNTF at 10 ng·ml$^{-1}$, 3-Isobutyl-1-methylxanthine (IBMX) (Sigma) at 100 µM and forskolin (Sigma) at 10 µM. Half of the medium was replaced every day until the cultures were used for electrophysiological recordings.

Motor Neuron—Muscle Cell Coculture for NMJ in 2D

This procedure is a modified version of a previously published one (J. A. Umbach, K. L. Adams, C. B. Gundersen, B. G. Novitch, PLoS One 2012, 7, e36049). Similar to the glial cell culture, 35 mm Petri dishes were coated with PDL (200 µg·ml$^{-1}$) and laminin (10 µg·ml$^{-1}$). C2C12 were plated at ~$1\times10^4$ cells·cm$^{-2}$ and cultured in growth medium. The next day, medium was switched to high-glucose DMEM supplemented with 2% HS and 1% penicillin-streptomycin. Two days later, medium was supplemented with 1 µg·ml$^{-1}$ of AraC to eliminate the non-fused myoblast and another two days later, early myotubes were trypsinized, replated at a 1:2 ratio on PDL- and LN-coated 35 mm dishes and cultured in medium consisting of 1:1 10% HS myogenic medium and neuronal differentiation medium supplemented with 1 µg·ml$^{-1}$ of AraC. On day 4 post myogenic induction, dissociated and purified Hb9$^{GFP+}$/ChR$^{tdTom+}$ motor neurons (see motor neuron—glial cells coculture) were plated at $2\times10^5$ cells/dish. AraC was withdrawn from the medium and replaced with GDNF (5 ng·ml$^{-1}$), CNTF (5 ng·ml$^{-1}$), forskolin (5 µM) and IBMX (50 µM). The subsequent days, half of the medium was replaced.

Cell Seeding and Differentiation in the Microfluidic Device

Cell Seeding in the Microfluidic Device

All three-dimensional cell cultures in the microfluidic devices were carried out in a collagen:Matrigel hydrogel in a 4:1 ratio. Rat tail type I collagen (Corning) was mixed on ice with 10×PBS with phenol red (serving as pH indicator), 0.5 N NaOH and water for cell culture in order to yield a collagen concentration of 2 mg·ml$^{-1}$ at a pH of 7.4. Matrigel without growth factors (BD science) was thoroughly mixed to the collagen at 20% of the final gel mixture volume. The gel was then used within a few minutes following its preparation in order to avoid pre-polymerization.

C2C12 were trypsinized, counted and centrifuged for 5 min at 200 rcf. The pellet was then resuspended in the hydrogel at a final density of $2\times10^6$ cells·ml$^{-1}$. Shortly after resuspension, the hydrogel was injected into the right most channel of the microfluidic device that had been filled with medium prior to cell seeding. This later facilitated gel compaction as it allowed for the formation of a thin layer of medium that isolated the gel and the cells from the PDMS walls and reduced adhesion. The device was then placed in a humidified box and incubated at 37° C. To prevent cells from settling at the bottom of the device and ensuring a homogeneous distribution throughout the thickness of the channels, the devices were first placed upside down for 4 min and then rotated back to complete polymerization for a remaining 11 min. Growth medium was then supplied to the adjacent medium channel by forming a seal between a large-orifice pipet tip and the medium filling port and by pushing medium into the channel. The followings days, medium would seep through the dry channels to the left of the muscle chamber and fully wet all channels. Medium was replaced by removing approximately 50 µL of old medium and replacing it with the same amount of fresh one. To prevent cross-flow that could wash off the gel, medium was aspirated and supplied with a multichannel pipettor. Medium was changed every 24 h.

Muscle Differentiation

After tissue ablation, the muscle bundles were supplied with myogenic medium, consisting of 2% HS DMEM (FIG. 8). Three days after induction, medium was replaced by a 10% HS myogenic medium (more adequate for the metabolically active muscle strips) until device reassembly and motor neuron seeding.

Plasmid Design and Delivery

DNA constructs were created using standard molecular biology techniques. Briefly, a ChR2[H134R]-tdTomato expression cassette was cloned into the Ai9 ROSA26 targeting vector and linearized for mESC knockin (FIG. 11a). Ai9 has been assigned Addgene plasmid #22799. For lentiviral infection of C2C12 cells ChR2[H134R]-tdTomato was cloned downstream of an EF1α promoter in a lentiviral plasmid (FIG. 15a).

mESC: The linearized ChR2[H134R]-tdTomato Rosa26 targeting vector (0.4 µg) was delivered to the mESC by nucleofection (Amaxa Nucelafector) for homologous recombination at the ROSA26 locus. Three days after plasmid delivery, a total of 9 colonies were manually selected, based on their ES-like morphologies and tdTomato expression, expanded, and tested for specific integration by Southern blotting. One clone displaying specific integration at the ROSA26 locus was selected for the rest of the study (FIG. 11).

C2C12: For lentivirus production, HEK293FT cells were seeded into a T225 flask at 40% confluency 24 h before transfection. Cells were transfected with 10 µg of EF1α-ChR2[H134R]-tdTomato, 10 µg pMD2.G, 15 µg psPAX2, 100 µl Lipofectamine 2000 (Life Technologies), and 200 µl Plus Reagent (Life Technologies). 6 h after transfection, fresh medium was applied. 3 days after transfection, virus supernatant was harvested, filtered through a 0.45 µm PVDF filter (Millipore), aliquoted, and stored at −80° C. Lentiviral packaging plasmids (psPAX2 and pMD2.G) have been assigned Addgene plasmids #12260 and 12259. C2C12 cells were incubated with viral supernatant for 24 h. The cells were cultured for 3 days, then expanded for another 3 days and sorted by FACS. 50% of the brightest cells were collected out of the 12% of positive cells to tdTomato.

RNA Extraction and RT-qPCR for Gene Expression Analyses

RNA was extracted using Izol (5PRIME, 2302700) according to manufacturer instructions. 5 µg of the extracted RNA was reverse transcribed using M-MLV Reverse Transcriptase (Life Technologies 28025-013) and random hexamers according to manufacturer protocols. Quantitative PCR reactions were performed with SYBR Green Master Mix (Roche). Relative mRNA levels were determined in triplicate for each transcript using the manufacturer's software (Advanced Relative Quantification with Roche Lightcycler 480 Software Version 1.5) using Tubb5 transcript levels for normalization. The primers used for gene expression analyses are listed below.

| No. | Transcript name | Forward (5'-3') | Reverse (5'-3') |
|---|---|---|---|
| 1. | Pou5f1 | GCTCACCCTG GGCGTTCTC (SEQ ID NO: 1) | GGCCGCAGCTT ACACATGTTC (SEQ ID NO: 2) |
| 2. | Klf4 | CAGGCTGTGG CAAAACCTAT (SEQ ID NO: 3) | CGTCCCAGTCA CAGTGGTAA (SEQ ID NO: 4) |
| 3. | Nanog | AAGTACCTCA GCCTCCAGCA (SEQ ID NO: 5) | GTGCTGAGCCC TTCTGAATC (SEQ ID NO: 6) |
| 4. | Sox2 | AGGGCTGGGA GAAAGAAGAG (SEQ ID NO: 7) | ATCTGGCGGAG AATAGTTGG (SEQ ID NO: 8) |
| 5. | Esrrb | GAACACTCTC GCCTGGTAGG (SEQ ID NO: 9) | CGCCTCCAGGT TCTCAATGT (SEQ ID NO: 10) |

Southern Blot Analyses

Genomic DNA was isolated from desired clones and digested with BamH1-HF overnight. The digested DNA was run on a 1% agarose gel and transferred using capillary transfer method. The clones were analyzed for targeting using an internal probe against channelrhodopsin. This 809 bp probe was amplified by PCR from the targeting vector using the PCR primers-Fwd 5' tcctggtccctgaggatcaa 3' (SEQ ID NO: 11 )and Rev 5'gcggaacggagatcgaggtc 3' (SEQ ID NO: 12 ). To check correct targeting of the 5' end, an 865 bp external probe was generated by digesting a vector containing the Rosa26 promoter (pROSA26-promoter, Addgene #21710) with SacI and Kpn1.

Immunostaining

Cells were fixed with 4% paraformaldehyde for 20 min, then solubilized with 0.1% Triton-X. After serum blocking, the cells were incubated at 4° C. overnight with the primary antibody. The following day, secondary antibody was administered for 2 h at room temperature. Primary antibodies included anti-Oct4 (Abcam, 1:200) and anti-sarcomeric α-actinin antibody (Abcam, 1:400). Secondary antibodies, used at 1:200 dilutions, were goat-anti-rabbit Texas Red (Invitrogen) and goat-anti-mouse AlexaFluo488 (Invitrogen). Neuromuscular junctions were inhibited and stained in live or fixed culture with AlexaFluo647 conjugated alpha-Bungarotoxin (Invitrogen) for 20 min in medium at a concentration of 5 µg·ml$^{-1}$. Counterstaining was performed with DAPI (Invitrogen, 1:1000).

Electrophysiological Assay

For the patch-clamp recordings, the FACS-sorted Hb9$^{GFP+}$/ChR$^{tdTom+}$ motor neurons were plated on primary mouse cortical glial cells (SI text). The glial were plated at a density of 1×10$^4$ cells·cm$^{-2}$ on PDL-coated 35-mm Petri dishes and allowed to reach confluency. Recordings were conducted on days 3, 10 and 16 post plating. The Hb9$^{GFP+}$/ChR$^{tdTom+}$ motor neurons were identified under a conventional inverted epifluorescent microscope (Axio Observer.A1, Zeiss) with a 20× objective lens (Plan-Neofluar, NA=0.4, Zeiss). The formulation of the recording solutions were taken from past literature (E. O. Mazzoni, S. Mahony, M. Closser, C. a Morrison, S. Nedelec, D. J. Williams, D. An, D. K. Gifford, H. Wichterle, Nat. Neurosci. 2013, 16, 1219). The bath solution consisted of (in mM): 145 NaCl, 5 KCl, 10 HEPES, 2 CaCl$_2$, 10 glucose and 2 MgCl$_2$ (pH 7.3 adjusted with NaOH, 325 mOsm adjusted with sucrose). The patch pipet solution contained (in mM): 130 CH$_3$KO$_3$S, 10

CH$_3$NaO$_3$S, 1 CaCl$_2$, 10 EGTA, 10 HEPES, 5 Mg-ATP, 0.5 Na$_2$-GTP (pH 7.3, 315 mOsm). The resistance of the electrodes was 4-8 MΩ. Patch-clamp experiments were performed using a Multiclamp 700B amplifier (Axon, Union City, Calif., USA) and signals were digitized at 10 kHz with an Axon Digidata 1440A interface. Data were acquired with pClamp 10 software (Axon) and processed with Mathlab (Mathworks, Natick, Mass.). For all voltage clamp experiments, the cells were held at a membrane potential of −60 mV. Action potentials were recorded while holding the neurons to approximately −60 mV by injecting current with amplitudes no less than −300 pA. All recordings were conducted at room temperature.

Optical and Electrical Stimulation

All optical stimulations were performed using a SOLA light engine (Lumencor, Beaverton, Oreg.) excitation unit, with emission peaks of interest located at 470 nm and 540-550 nm. Blue and green lights were supplied through Zeiss filter sets #38 (BP 470/40) and #20 (BP 546/12), respectively. For the electrophysiological recordings, light was controlled by the Clampex software and applied through the 20× objective, yielding a maximum irradiance of 9 mW·mm$^{-2}$ as measured by a power meter (Newport) at the sample plane. The optical stimulations of the myofibers and motor neurons in adherent and microfluidic cultures were conducted through a 10× objective, yielding an irradiance of 7.6 mW·mm$^{-2}$ and controlled via an Arduino circuit board.

Electrical stimulation was delivered via platinum electrodes positioned 3 mm away from each other across the neuromuscular tissue and controlled by an Arduino circuit delivering 9V square inputs.

Image Acquisition and Analysis

Epifluorescence and confocal images were acquired on a Nikon eclipse TiE inverted microscope and an Olympus FV-1000 confocal microscope, respectively. three-dimensional reconstruction and analysis of confocal images was performed with the software Imaris (Bitplane, Zurich, Switzerland). Automated tracking of the local deformation of the skeletal muscle cells and deflection of the pillars upon light excitation was carried out using the tracking software Tracker (physlets.org/tracker). The synchronization of deformation tracking and optical stimulation was carried out but plotting the average pixel intensity for every image over time and comparing the increase of intensity to the muscle or pillar deformation curve (FIG. 13A). The blue bars correspond to periods of time when the light was on.

Image analysis for muscle width and axon outgrowth was conducted in ImageJ (http://imagej.nih.gov/). Maximum neurite growth rate was defined as the speed of extension of the longest neurite with respect to the border of the EB on seeding day. Electrophysiology and FACS data were processed in Matlab (Mathworks, MA).

Statistical Analysis

Statistical analysis was conducted in Graphpad Prism (Graphpad Software, Inc, San Diego, Calif.). Statistical significance analysis was done via a two-way ANOVA and all tests resulting in a p-value less than 0.05 were considered statistically significant.

Glial Feeder Layer Cultures

CD1 Mouse cortical glial cultures were provided by Dr. L. B. Wood, Beth Israel Deaconess Medical Center. Cultures were received in minimum essential medium (Sigma) with 10% horse serum (Sigma), 0.3% Anhydrous Dextrose (Fisher), 1x antibiotic antimycotic solution (Sigma).

Post Deflection Characterization

The measurement device was previously described (D. Neal, M. S. Sakar, L.-L. S. Ong, H. Harry Asada, Lab Chip 2014, DOI 10.1039/c41c00023d). Briefly, copper wire (Remington Industries, Johnsburg, Ill.) at 40 AWG size (87 µm diameter), was cut approximately 2 cm in length and mounted on a 3-axis translation stage assembled from one MT1 (X-axis) and two DT12 dovetail (Y- and Z-axes) series manual translators (Thorlabs, Newton, N.J.). The copper probe was calibrated by hanging known wire weights against gravity on the probe tip. The measurements were used to generate a load vs. displacement curve, which was then fit using linear regression. The stiffness of the copper probe was determined to be 0.155 µN·µm$^{-1}$.

The posts were immersed in cell culture medium. The probe tip was gently positioned and in contact with the top-center of the posts. The probe tip was directed to translate at 10 µm intervals with return from 0 µm (origin) to 200 µm (20% post deflection) in the X-axis using the linear translator. A laser-optical sensor (optoNCDT 1401-1, Micro-Epsilon Optronic, Ortenburg, Germany) was used to measure position and displacement of the probe base. Software from the manufacturer (ILD1401 Tool v2.09, Micro-Epsilon Optronic, Ortenburg, Germany) was used to measure and record output values. Image sequences of the probe tip's position and displacement were captured on the microscope stage (IX81, Olympus, Center Valley, Pa. 18034) by video capture software (Debut Video Capture, NCH Software, Greenwood Village Colo.) from a live acquisition software feed (MetaMorph, Molecular Devices, Sunnyvale, Calif.) using a digital CCD camera (ORCA-R2C10600-10B, Hamamatsu Photonics, Bridgewater, N.J.).

The deflection of the post using the copper probe of known stiffness was used to determine the post stiffness. The post stiffness was measured to be 0.36±0.08 µN·µm$^{-1}$ (n=14), within the range of values reported in previous studies (W. R. Legant, A. Pathak, M. T. Yang, V. S. Deshpande, R. M. McMeeking, C. S. Chen, Proc. Natl. Acad. Sci. U.S.A 2009, 106, 10097; T. Boudou, W. R. Legant, A. Mu, M. A. Borochin, N. Thavandiran, M. Radisic, P. W. Zandstra, J. A. Epstein, K. B. Margulies, C. S. Chen, Tissue Eng. Part A 2012, 18, 910). For such a bending stiffness, the Young's modulus determined as a fitting parameter to the analytical solutions and computational simulations was found to be 1.26 and 1.11 MPa respectively, consistent with the 1 MPa measurement reported in the literature for a 5:1 mixing ratio (J. Y. Park, S. J. Yoo, E.-J. Lee, D. H. Lee, J. Y. Kim, S.-H. Lee, BioChip J. 2010, 4, 230).

Muscle Bundle Ablation

Manual Ablation: After 2 days in the microfluidic device, the reversibly bonded top layer of the device was gently peeled off and the tissue strips reminiscent of the gel filling channels and connector channel were ablated with a gauge 26 needle under a stereomicroscope. Medium was gently aspirated around the 2 muscle strips and a PDMS annulus was positioned on top of the bottom membrane in order to form a large medium reservoir (FIG. 8).

2P-Ablation: Beside imaging (M. Oheim, D. J. Michael, M. Geisbauer, D. Madsen, R. H. Chow, Adv. Drug Deliv. Rev. 2006, 58, 788) or local photoactivation of light-sensitive channels (B. K. Andrasfalvy, B. V Zemelman, J. Tang, A. Vaziri, Proc. Natl. Acad. Sci. U.S.A 2010, 107, 11981; D. Oron, E. Papagiakoumou, F. Anselmi, V. Emiliani, Two-Photon Optogenetics, Elsevier B.V., 2012) or three-dimensional resolved photodynamic therapy (C. J. Rowlands, J. Wu, S. G. M. Uzel, O. Klein, C. L. Evans, P. T. C. So, Laser Phys. Lett. 2014, 11, 115605), two-photon excitation has been used to generate microtrack by collagen ablation (O. Ilina, G.-J. Bakker, A. Vasaturo, R. M. Hoffman, P. Friedl, Phys. Biol. 2011, 8, 029501). A similar principle was used to ablate muscle tissue. Two-photon ablation was performed on a custom-built ablation setup. The beam from an ultrafast laser (Spectra Physics, Mai Tai HP) of a 750 nm wavelength was expanded by a factor of 2 using two lenses in a 4f configuration (Newport, KPX094AR.16 and KPX106AR.16), then through a half waveplate (Newport, 10RP02-46) and Glan Thompson polarizer (Newport, 10GT04AR.16) for power control, before passing through a shutter (Oriel, 76992). The beam was further expanded by a factor of 3 using a beam expander (Thorlabs, BE03M-B) so as to fill the back aperture of the microscope objective. The resulting beam was then coupled into the back (fluorescence) port of a microscope body (Zeiss, Axiovert 40 CFL), where it reflected off the dichroic mirror (Semrock, FF750-SDi02-25×36) and passed into a 20×0.5 numerical aperture air immersion objective (Zeiss, 440340-9904-000). The sample was simultaneously illuminated using brightfield illumination in order to image the ablation process; a camera (Thorlabs, DCC1545M) was used to capture the image. The sample was mounted on an automated microscope stage (Prior Scientific, HK01SKOP) however the stage was controlled manually. In order to perform tissue ablation, the microscope was first calibrated using a sample consisting of polymer nanospheres on a glass coverslip, in order to determine the location of the beam focus. The sample was then placed on the microscope and brought into focus, and the ablation turned on using the shutter. The beam was manually rastered across the sample in order to fully cut the tissue at the desired location (FIGS. 14a and b). Care was taken so as to avoid ablating the PDMS and destroying the sample.

This technique has the advantage of performing ablation non-invasively in a closed environment and should be considered as the best alternative when opening the device is not an option. It could also be automated to carry out computer-aided multiple ablations.

Both manual and 2P technique yielded comparable results in terms of tissue tail resorption (FIG. 14c), and muscle differentiation.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims. The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A microfluidic device for coculture of a muscle cell and a neuronal cell for innervating a muscle bundle, the microfluidic device comprising:
 a coculture chamber or a plurality of coculture chambers, each of said chamber comprising:
  a first culture compartment including one or more retaining features, the first culture compartment having a width of at least 100 μm;
  a second culture compartment including one or more compliant pillars, the second culture compartment having a width of at least 100 μm; and
  a buffer compartment separating the first compartment and the second compartment by a distance of at least about 200 μm;
 wherein the compliant pillars are deflectable to measure force generated by the muscle bundle and the one or more compliant pillars have a height of at least 50 μm.

2. The microfluidic device of claim 1, wherein the height is about 50 μm, 100 μm, 150 μm, 250 μm, 260 μm, 270 μm, 280 μm, 290 μm, 300 μm, 310 μm, 320 μm, 330 μm, 340 μm, 350 μm, 1 mm, or 1.5 mm; and the width of the first culture compartment is about 100 μm, 500 μm, 1.25 mm, 1.5 mm, 1.75 mm, 2 mm, 2.5 mm, 3 mm, 4 mm, or 5 mm.

3. The microfluidic device of claim 1, wherein the first culture compartment, the second culture compartment, or the buffer compartment includes a volume of at least 650 μm³; or wherein the first culture compartment, the second culture compartment, or the buffer compartment includes a volume of about 650 μm³, 700 μm³, 750 μm³, 800 μm³, 850 μm³, 900 μm³, 950 μm³, 1600 μm³, or 2100 μm³.

4. The microfluidic device of claim 1, wherein innervating a muscle bundle comprises one or more of
 (a) growth of neurites into contact with the external surface of the muscle bundle;
 (b) growth of neurites past the external surface and into the muscle bundle; and
 (c) formation of a neuromuscular junction between an axon and a muscle cell of the muscle bundle.

5. The microfluidic device of claim 1, wherein the one or more retaining features comprise a rigid substantially concave barrier, wherein the barrier comprises
 (a) about 1, 2, 3, 4, 5, 6, 7, 8, 9, 10 or more are pillars or plates positioned in a substantially concave arrangement; or
 (b) a substantially concave wall with slits, holes, or openings too small for a neuron or neurosphere to pass through but large enough for an axon to pass through.

6. The microfluidic device of claim 1, wherein the first culture compartment contains a neuronal cell, the second culture compartment contains a muscle cell, and the buffer compartment contains a hydrogel.

7. The microfluidic device of claim 1, wherein the first culture compartment, the second culture compartment, and the buffer compartment contain a hydrogel.

8. The microfluidic device of claim 7, wherein the hydrogel in the first culture compartment, the second culture compartment, and/or the buffer compartment contains a cell other than the neuronal cell or the muscle cell;
 wherein the cell comprises a Schwann cell, an endothelial cell, a satellite cell, or a glial cell;
 the neuronal cell comprises a photosensitized cell; or
 the neuronal cell comprises a patient-derived neuronal cell from a patient who has been diagnosed with amyotrophic lateral sclerosis (ALS) or spinal muscular atrophy (SMA).

9. The microfluidic device of claim 1, wherein the neuronal cell
 (a) is within a neurosphere;
 (b) comprises a neural stem cell;
 (c) comprises a neuron;
 (d) comprises an interneuron;
 (e) comprises a sensory neuron;
 (f) comprises a motor neuron;
 (g) comprises about 1 to 1000, 100,000 to 10,000,000, 1000 to 1,000,000, or more than 1,000,000 neurons;
 (h) comprises a dimension of about 50-2000 microns at its widest diameter;
 (i) comprises embryonic neural stem cells;

(j) comprises induced pluripotent neural stem cells; or (k) comprises a neuron, an astrocyte, and/or an oligodendrocyte; and wherein the muscle cell (a) is within a muscle bundle;

(b) comprises a myoblast;

(c) comprises a cardiac, skeletal, or smooth muscle cell;

(d) comprises about 1 to 1000, 1000 to 10,000, 1 to 20,000, or at least about 1000, 5000, or 10,000 muscle cells;

(e) is about 0.5, 1, 2, 3, 4, 5, 2 to 3 or 0.05-5 mm long; or (f) comprises a cardiac, skeletal, and/or smooth muscle cell.

10. The microfluidic device of claim 1, wherein an axon extends from the first culture compartment through the buffer compartment to the second culture compartment and forms a three-dimensional neuromuscular junction with the muscle cells.

11. The microfluidic device of claim 1, further comprising:

one or more neuronal inlet injection ports for seeding the first culture compartment with neuronal cells;

one or more muscle inlet injection ports for seeding the second culture compartment with muscle cells;

a first medium reservoir adjacent the first culture compartment; and a second medium reservoir adjacent the second culture compartment, the first and second medium reservoirs enabling generation of gradients of growth factors.

12. The microfluidic device of claim 1, wherein the first culture compartment, the second culture compartment, and/or the buffer compartment comprises a hydrogel.

13. The microfluidic device of claim 12, wherein the hydrogel comprises an alginate or a derivative thereof, gelatin, collagen, agarose, a natural or synthetic polysaccharide, polylactic acid, polyglycolic acid, poly(lysine), a polyanhydride; a poly(lactide-co-glycolide) (PLGA) polymer, a polyamino acid, a poly(alkylene oxide), a poly(ethylene oxide), a poly(allylamine)(PAM), a poly(acrylate), a polyester, polyhydroxybutyrate and poly-epsilon-caprolactone, a polyphosphazine, a poly(vinyl alcohol), a modified styrene polymer, poly(4-aminomethylstyrene), a pluronic polyol, a polyoxamer, a poly(uronic acid), a poly(vinylpyrrolidone), and/or a copolymer comprising one or more of an alginate or a derivative thereof, gelatin, collagen, agarose, a natural or synthetic polysaccharide, polylactic acid, polyglycolic acid, poly(lysine), a polyanhydride; a poly(lactide-co-glycolide) (PLGA) polymer, a polyamino acid, a poly(alkylene oxide), a poly(ethylene oxide), a poly(allylamine)(PAM), a poly(acrylate), a polyester, polyhydroxybutyrate and poly-epsilon-caprolactone, a polyphosphazine, a poly(vinyl alcohol), a modified styrene polymer, poly(4-aminomethylstyrene), a pluronic polyol, a polyoxamer, a poly(uronic acid), and a poly(vinylpyrrolidone).

14. The microfluidic device of claim 1, wherein the hydrogel has been crosslinked or may be crosslinked by temperature-induced crosslinking, photocrosslinking, or enzymatic crosslinking.

15. The microfluidic device of claim 1, wherein the muscle bundle is attached to each of the one or more compliant pillars and a portion of the muscle bundle is wrapped around each of the one or more compliant pillars.

16. A method comprising:

seeding a second culture compartment with muscle cells to enable growth of a muscle bundle, the muscle bundle wrapping around compliant pillars, the second culture compartment forming part of a microfluidic device; and seeding a first culture compartment with neuronal cells to enable growth of an axon to extend from the first culture compartment through a buffer compartment to the second culture compartment and form a three-dimensional neuromuscular junction with the muscle bundle;

wherein the microfluidic device is for coculture of the muscle cell and the neuronal cells for innervating the muscle bundle, the microfluidic device comprising:

a coculture chamber or a plurality of coculture chambers, each of said chamber comprising:

the first culture compartment including one or more retaining features, the first culture compartment having a width of at least 100 µm;

the second culture compartment including the one or more compliant pillars, the second culture compartment having a width of at least 100 µm; and the buffer compartment separating the first compartment and the second compartment by a distance of at least about 200 µm;

wherein the compliant pillars are deflectable to measure force generated by the muscle bundle and the one or more compliant pillars have a height of at least 50 µm.

17. The method of claim 16, further comprising:

stimulating the neuronal cells; and measure deflection of the compliant pillars that result from contraction of the muscle bundle, the contraction caused by the stimulation of the neuronal cells.

18. The method of claim 16, wherein microfluidic device further comprises a test compound, wherein the test compound comprises a drug candidate; or the test compound is an organic compound having a molecular weight less than 1000 or 2000 daltons, an RNA interference molecule, a protein, a peptide, an antibody, an antibody fragment, or an aptamer.

19. The method of claim 16, further comprising:

adding a medium having a first concentration to a first medium reservoir adjacent the first culture compartment to generate a gradient medium within the coculture chamber;

adding a second medium having a second concentration to a second medium reservoir adjacent the second culture compartment.

20. The method of claim 16, wherein the second compartment includes hydrogel and the three-dimensional neuromuscular junction forms in the hydrogel.

* * * * *